(12) United States Patent
Gupta

(10) Patent No.: US 9,023,876 B2
(45) Date of Patent: *May 5, 2015

(54) COMPOUNDS AND METHODS FOR REGULATING INTEGRINS

(75) Inventor: Vineet Gupta, Pinecrest, FL (US)

(73) Assignee: Adhaere Pharmaceuticals, Inc., Miami, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 12/904,273

(22) Filed: Oct. 14, 2010

(65) Prior Publication Data

US 2012/0010255 A1 Jan. 12, 2012

Related U.S. Application Data

(60) Provisional application No. 61/362,363, filed on Jul. 8, 2010.

(51) Int. Cl.
| | | |
|---|---|---|
| C07D 277/34 | (2006.01) | |
| C07D 277/36 | (2006.01) | |
| A61K 31/425 | (2006.01) | |
| C07D 417/06 | (2006.01) | |

(52) U.S. Cl.
CPC .................................. *C07D 417/06* (2013.01)

(58) Field of Classification Search
None
See application file for complete search history.

(56) References Cited

U.S. PATENT DOCUMENTS

| | | | |
|---|---|---|---|
| 7,718,680 B2 * | 5/2010 | Pellecchia et al. ............ | 514/369 |
| 2002/0052396 A1 | 5/2002 | Bailey et al. | |
| 2004/0002526 A1 * | 1/2004 | Klein et al. .................... | 514/369 |
| 2005/0042213 A1 | 2/2005 | Gelder et al. | |
| 2005/0282840 A1 * | 12/2005 | Ross et al. ..................... | 514/269 |
| 2006/0224234 A1 | 10/2006 | Jayaraman et al. | |
| 2007/0048216 A1 | 3/2007 | Norenberg et al. | |
| 2008/0033025 A1 * | 2/2008 | Pellecchia et al. ............ | 514/369 |
| 2009/0069288 A1 | 3/2009 | Breinlinger et al. | |
| 2009/0130098 A1 | 5/2009 | Goodman et al. | |
| 2010/0056503 A1 * | 3/2010 | Gupta et al. ............... | 514/225.2 |
| 2010/0331315 A1 * | 12/2010 | Haddach et al. ............. | 514/218 |

FOREIGN PATENT DOCUMENTS

| | | | |
|---|---|---|---|
| FR | 2858324 A1 | 2/2005 | |
| WO | 00/10573 A1 | 3/2000 | |
| WO | 2004/093803 A2 | 11/2004 | |
| WO | 2005/016227 A2 | 2/2005 | |
| WO | 2005/020990 A1 | 3/2005 | |
| WO | WO 2005041951 A2 * | 5/2005 | |
| WO | WO 2005076695 A2 * | 8/2005 | |
| WO | 2006/024699 A1 | 3/2006 | |
| WO | 2008/082537 | 7/2008 | |

OTHER PUBLICATIONS

Verma et al. Molecular Pharmaceuticals (2008) 5(5):745-759.*
Forino et al PNAS (2005) 102(27):9499-9504.*
Tautz et al. J. Biological Chemistry (2005) 280(10):9400-9408.*
Gill et al JOC 2005 70(26):10726-10731.*
Carter et al. PNAS (2001), 98(21), 11879-11884.*
Bjorklund et al., "Stabilization of the Activated $\alpha_M\beta_2$ Integrin by a Small Molecule Inhibits Leukocyte Migration and Recruitment," Biochemistry, 2006, vol. 45, pp. 2862-2871.
Celik et al., "Agonist Leukadherin-1 Increases CD11b/CD18-Dependent Adhesion Via Membran Tethers," Biophysical Journal, 2013, vol. 105, pp. 2517-2527.
Faridi et al., "Identification of novel agonists of the integrin CD11b/CD18," Bioorganic & Medicinal Chemistry Letters, 2009, vol. 19, pp. 6902-6906, DOI: 10.1016/j.bmcl.2009.10.077.
Faridi et al., "Small molecule agonists of integrin CD11b/CD18 do not induce global conformational changes and are significantly better than activating antibodies in reducing vascular injury," Biochimica et Biophysica Acta 1830 (2013) pp. 3696-3710.
Maiguel et al., "Small Molecule-Mediated Activation of the Integrin CD11b/CD18 Reduces Inflammatory Diseases," Science Signaling, 2011, vol. 4(189), ra57, DOI: 10.1126/scisignal.2001811.
Nathan et al., "Tumor necrosis factor and CE11/CD18 (beta2) integrins act syngeristically to lower cAMP in human neutrophils," J Cell Biology, 1990, vol. 111, pp. 2171-2181.
Park et al., "A Simple, No-Wash Cell Adhesion-Based High-Throughput Assay for the Discovery of Small-Molecule Regulators of the Integrin CD11b/CD18," Journal of Biomolecular Screening, 2007, vol. 12, pp. 406, DOI: 10.1177/1087057106299162.
Reed et al., "Complement Receptor 3 Influences Toll-like Receptor 7/8-Dependent Inflammation," Journal of Biological Chemistry, 2013, vol. 288(13), pp. 9077-9083.
Shah, "Inflammation, Neointimal Hyperplasia, and Restenosis: As the Leukocytes Roll, the Arteries Thicken," Circulation, 2003, vol. 107(17), pp. 2175-2177, DOI: 10.1161/01.cir.0000069943.41206.bd.
Chemical Abstracts RN 344897-95-6; entered STN Jul. 8, 2001, 1 page.
ChemBridge Catalog # 5679982 4-{5-[(Z)-(3-Benzyl-4-oxo-2-thioxo-1,3-thiazolidin-5-ylidene)methyl]-2-furyl}benzoic acid, http//:www.hit2lead.com/result.asp?search=14662037, retrieved on Jan. 7, 2014.
ChemBridge Catalog # 5578913 4-{5-[(Z)-(2,4-Dioxo-3-phenyl-1,3-thiazolidin-5-ylidene)methyl]-2-furyl}benzoic acid, http//:www.hit2lead.com/result.asp?search=82461052, retrieved on Jan. 7, 2014.
ChemBridge Catalog # 6789780 Ethyl [(5Z)-5-{[5-(2,4-dichlorophenyl)-2-furyl]methylene}-2,4-dioxo-1,3-thiazolidin-3-yl]acetate, http//:www.hit2lead.com/result.asp?search=13199976, retrieved on Jan. 8, 2014.

(Continued)

*Primary Examiner* — Nyeemah A Grazier
(74) *Attorney, Agent, or Firm* — Kilpatrick Townsend & Stockton LLP

(57) ABSTRACT

The application describes small molecules capable of modulating activity of beta2 family of integrins, such as integrin CD11b/CD18 (also known as Mac-1, CR3 and αMβ2). Such compounds may be used in certain embodiments for treating a disease or condition, such as inflammation, immune-related disorders, cancer, ischemia-reperfusion injury, stroke, neointimal thickening associated with vascular injury, wound-healing, organ transplantation and cardiovascular disease, among others.

11 Claims, 13 Drawing Sheets

(56) References Cited

OTHER PUBLICATIONS

ChemBridge Catalog # 6528335 2-Chloro-5-(5-{(Z)-[(4-fluorobenzyl)-2,4-dioxo-1,3-thiazolidin-5-ylidene]methyl}-2-furyl)benzoic acid, http//:www.hit2lead.com/result.asp?search=30881677, retrieved on Jan. 8, 2014.

ChemBridge Catalog # 6725132 Ethyl [(5Z)-2,4-dioxo-5-[(5-phenyl-2-furyl)methylene]-1,3-thiazolidin-3-yl}acetate, http//:www.hit2lead.com/result.asp?search=85021953, retrieved on Jan. 8, 2014.

ChemBridge Catalog #: 7476685 (5Z)-3-(2-Furylmethyl)-5-[(5-phenyl-2-furyl)Omethylene]-2-thioxo-1,3-thiazolidin-4-one, http//:www.hit2lead.com/result.asp?search=17650479, retrieved on Jan. 8, 2014.

EP Application No. 11 80 3961, Supplementary European Search Report, Date of completion Oct. 16, 2013, 1 page.

PCT Application No. PCT/US2011/034753, International Search Report, Date of mailing Oct. 3, 2011, 3 pages.

Lee et al., Crystal Structure of the A domain from the alpha subunit of Integrin CR3 (CD11B/CD18), Cell, Feb. 1995; vol. 80, pp. 631-633.

* cited by examiner

Figure 5:
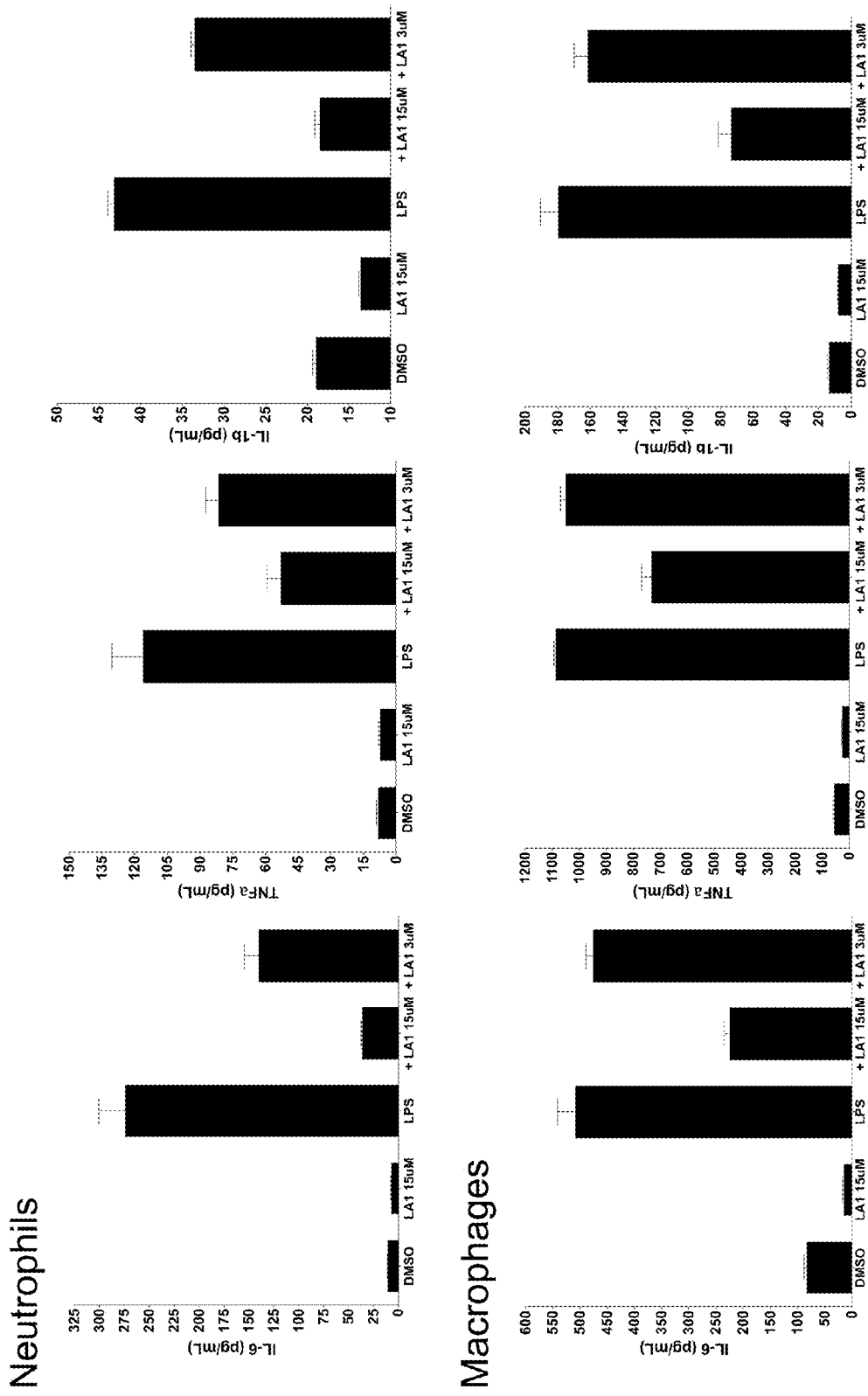

Figure 5. Leukadherins Reduce Secretion of Pro-inflammatory Cytokines

Figure 13

Table S1. White blood cell count in mouse whole blood samples (n=3-5 animals)

|  | Saline | LA1 | LA2 | LA3 |
|---|---|---|---|---|
| WBC count | $3.6 \pm 1.1 \times 10^3/\mu L$ | $3.4 \pm 0.7 \times 10^3/\mu L$ | $3.8 \pm 1.3 \times 10^3/\mu L$ | $3.8 \pm 0.7 \times 10^3/\mu L$ |
| p-value | ns | ns | ns | ns |

COMPOUNDS AND METHODS FOR REGULATING INTEGRINS

CROSS-REFERENCE TO RELATED APPLICATIONS

This patent application claims the benefit of U.S. Provisional Application No. 61/362,363 filed on Jul. 8, 2010. The specification of this application is incorporated herein by reference in its entirety.

FIELD OF INVENTION

This invention relates to compounds that modulate function of beta2 family of integrins. It is generally in the field of Chemistry and Pharmaceuticals.

BACKGROUND OF THE INVENTION

Integrins are non-covalently linked $\alpha/\beta$ heterodimeric receptors that mediate cell adhesion, migration and signaling. Together with their ligands, integrins play central roles in many processes including development, hemostasis, inflammation and immunity, and in pathologic conditions such as cancer invasion and cardiovascular disease. Leukocyte migration and recruitment is essential for their normal immune response to injury and infection and in various inflammatory and autoimmune disorders [1]. For example, in response to injury or infection leukocytes are recruited into the tissues where they participate in immune clearance [2]. The $\beta2$ integrins, a sub-family of $\alpha/\beta$ heterodimeric integrin receptors that have a common $\beta$-subunit ($\beta2$, CD18) but distinct $\alpha$-subunits (CD11a, CD11b, CD11c and CD11d [3]), are leukocyte specific receptors [4]. $\beta2$ integrins, including highly expressed integrin CD11b/CD18 (also known as Mac-1, CR3 and $\alpha M\beta2$), modulate leukocyte functions, including cell adhesion, migration, recruitment and activation [2]. CD11b/CD18 recognizes the complement fragment iC3b, Fibrinogen, and ICAM-1 as ligands, among various others. CD11b/CD18 has been implicated in many inflammatory and autoimmune diseases, such as ischemia-reperfusion injury (including acute renal failure and atherosclerosis), tissue damage, stroke, neointimal thickening in response to vascular injury and the resolution of inflammatory processes [5-9]. Leukocytic $\beta2$ integrins also modulate tumor infiltration. For example, tumors also secrete inflammatory cytokines to recruit CD11b-expressing myeloid cells to facilitate neovascularization [10]. During cancer treatments, irradiated tumors recruit large numbers of specific leukocytes, bone marrow-derived CD11b-expressing myeloid cells expressing matrix metalloproteinase-9 (MMP-9), that restore tumor vasculature and allow tumor re-growth and recurrence [11]. Recent studies have shown that treatment with CD11b antagonists (anti-CD11b antibody) reduces CD11b-expressing myeloid cell infiltration and an enhancement of tumor response to radiation in mice [11]. Additionally, inflammatory leukocytes potentiate anti-GBM nephritis. Experimental anti-GBM nephritis in mice is a model of rapidly progressive glomerulonephritis, is characterized by proteinuria, leukocyte infiltration and glomerular crescent formation [12, 13]. Leukocytes play a critical role in the pathogenesis of anti-GBM nephritis, and their number correlates with the percentage of crescentic glomeruli. CD11b$^{-/-}$ animals show no proteinurea and strong protection of renal function [14], suggesting that agents targeting this integrin have a potential to treat this disease.

In addition to increasing cell adhesion and modulating migration, the beta2 integrins, including CD11b/CD18, mediate a number of intracellular signaling events, including production of reactive oxygen species and modulation of a number of pro- and anti-inflammatory genes in inflammatory cells [15-20]. Integrin activation and ligand binding leads to its clustering on the cell surface and initiates outside-in signaling, including the activation of PI3-K/Akt and MAPK/ERK1/2 pathways [16, 21], thereby mimicking the anchorage-dependent pro-survival signals in most cells. Ligation and clustering of integrins also synergistically potentiates intracellular signaling by other receptors (such as, Toll-like receptors (TLRs) and cytokine receptors interleukin-1 receptor (IL-1R) and TNFR) and both induce transcription factor (such as, NF-κB) dependent expression of pro-inflammatory cytokines (e.g.; IL1β, IL6, TNFα) as well as release of other factors (e.g.; Tissue Factor).

Thus, there is a considerable potential for agents that modulate the function of CD11b/CD18 and other beta2 integrin as therapeutic agents for the treatment of various diseases and conditions, including inflammatory conditions. Indeed, blocking beta2 integrins, including CD11b/CD18, and their ligands with antibodies and ligand mimics (anti-adhesion therapy) [22-24] and genetic ablation of CD11a, CD11b, CD11c or CD18 decreases the severity of inflammatory response in vivo in many experimental models [25-27]. However, such blocking agents have had little success in treating inflammatory/autoimmune diseases in humans [26, 28], perhaps because complete blockage of integrins with antibodies is difficult due to availability of a large mobilizable intracellular pool of such integrins (for example, CD11b/CD18) [29, 30] or because suppressing leukocyte recruitment with blocking agents requires occupancy of >90% of active integrin receptors [31]. Anti-integrin $\beta2$ antibodies have also shown unexpected side effects [32].

The above suggests that what is needed are small molecules that selectively regulate the ligand binding and function of beta2 integrins, including integrins CD11a/CD18 and integrin CD11b/CD18. Additionally, agents that do not compete with ligand binding (by targeting allosteric regulatory sites, such as the hydrophobic site-for-isoleucine (SILEN) pocket in CD11b/CD18) are especially desired. Moreover, compounds and methods to enhance or promote integrin-mediated cell-adhesion are highly desired. Furthermore, compounds that regulate cellular functions (such as cell activation and signaling) of inflammatory cells are highly desirable. Integrin activation has been proposed as an alternative to blockade (anti-adhesion) for modulating cell function and treating a number of diseases, including inflammatory diseases [33, 34]. It is based on the initial finding by Harlan and co-workers over 15 years ago that freezing of integrin $\alpha4\beta1$ in high avidity state using an activating antibody increases cell adhesion and decreases eosinophil migration [35]. Recent research with knock-in animals that express activating mutants of integrins $\alpha L\beta2$ [36, 37] and $\alpha4\beta7$ [38] provides in vivo support for this hypothesis.

However, compounds that enhance integrin activity are highly desired but no integrin-specific compounds and methods have been previously described. Additionally, whether transient activation of a fraction of native receptors in vivo, as is expected from small molecule treatment, will have biological effect also remains an open question. Moreover, an important requirement of useful compounds and compositions that regulate beta2 integrins, including CD11b/CD18, is that they not negatively impact the cell, tissue and animal viability. Some have suggested that integrin agonists might induce killing of target cells (Yang et al., *J Biol Chem* 281, 37904

(2006)), which is not desirable. Also, there is some prior art on the thiazolidine-one family of compounds, including U.S. Pat. No. 5,225,426, U.S. Pat. No. 7,566,732, U.S. Pat. No. 7,348,348, US 2006/0281798, US 2006/0183782, US 2006/0106077, US 2008/0108677, US 2010/0056503, WO 2009026346, WO/1995/029243. However, no compounds or methods with above described desirable properties have so far been described in the literature. It is an object of the invention to describe such compounds and methods. In addition, the present invention provides other related advantages.

SUMMARY OF THE INVENTION

The invention describes novel compounds, compositions and methods that are useful in targeting beta2 integrins, including CD11b/CD18. The invention also describes compositions and methods that are useful in detecting, diagnosing or treating various mammalian diseases and conditions, including, but not limited to, inflammatory diseases and conditions, autoimmune diseases and conditions and transplantation. The invention describes compositions and methods that are useful in improving the health of a patient.

The compounds and methods described in this invention are useful in activating beta2 integrins (such as CD11b/CD18), thereby modulating biological function of cells that express this protein. Such cells include leukocytes. Such biological functions include signaling pathways and gene expression. The compounds and methods described in this invention can also be used, via activation of beta2 integrin, to regulate levels of secreted factors in vitro and in vivo. In vitro or in vivo modulation of the levels of such soluble factors, which include factors such as cytokines, chemokines, microparticles, small molecules and other proteins and peptides, is also useful in treating a number of diseases and conditions in patients, including inflammatory and auto-immune disease and conditions.

This invention also describes our novel strategy, as an alternative to the anti-adhesion strategy that is currently practiced in literature, for regulating the biological function of integrins and integrin-expressing cells. Our strategy involves integrin activation, rather than its blockade, as a way to modulate the function or activity of beta2 intergins, including CD11b/CD18, and the function or activity of cells that express beta2 integrins, such as of leukocytes. The compounds of this invention are easily delivered in vitro, ex vivo and in vivo and can be readily derivatized or optimized for use in patients. Additionally, this invention shows that transient activation of a fraction of native receptors in vitro and in vivo (via administration of the compounds of this invention) affects the function of biological cells. Integrin activation is a novel, useful, pharmacologically targetable methodology to treat, without limitation, a variety of inflammatory and autoimmune diseases and conditions.

BRIEF DESCRIPTION OF THE FIGURES AND TABLES

Figure 1:
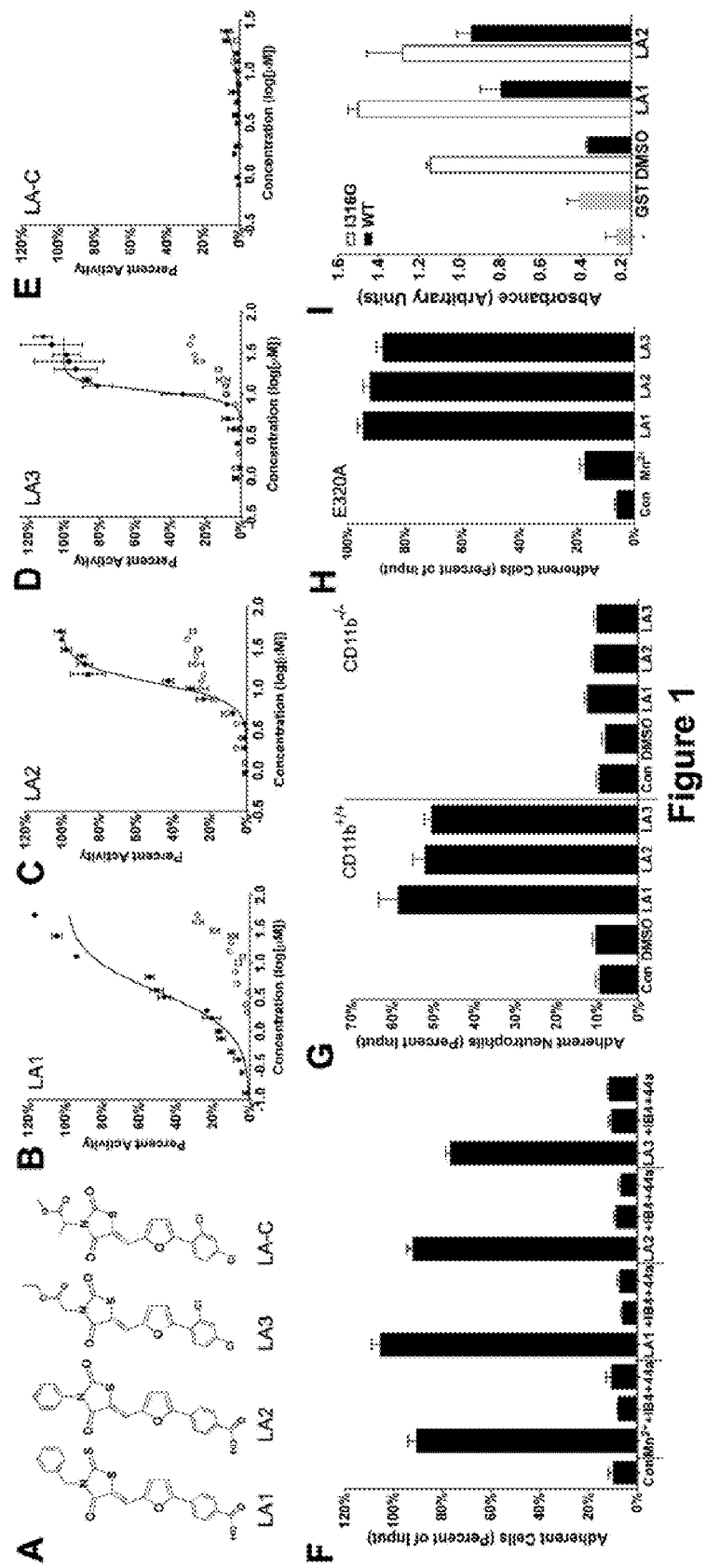

FIG. 1. Leukadherins increase CD11b/CD18 dependent cell adhesion. A. The chemical structures of LA1, LA2, LA3 and LA-C. B-E. Dose-response curves showing percentage of input K562 CD11b/CD18 (filled circles) and K562 (open circles) cells adhering to immobilized Fg in the presence of increasing amounts of LA1, LA2, LA3 and LA-C. F. Histograms showing LA1-3 induced adhesion of K562 CD11b/CD18 to Fg in the absence or presence of blocking antibodies IB4 and 44a. Also shown is the reference level of adhesion in the presence of physiologic $Ca^{2+}$ and $Mg^{2+}$ ions (Con) and with known agonist $Mn^{2+}$. Data shown are mean±SEM. G. Histograms showing adhesion of WT ($CD11b^{+/+}$) and $CD11b^{-/-}$ neutrophils to immobilized Fg in the absence (DMSO) or the presence of LA1-3 as compared to basal levels of adhesion (Con). Data shown are mean±SEM. H. Histograms showing LA1-3 induced binding of K562 E320A cells to immobilized Fg in the absence or presence of blocking antibodies (IB4, 44a). Also shown is the reference level of K562 E320A adhesion with $Ca^{2+}$ and $Mg^{2+}$ ions (Con) and $Mn^{2+}$. Data shown are mean±SEM. I. Histograms showing binding of recombinant GST-αA-domain constructs to the immobilized Fg in the absence (DMSO) or presence of LA1 and LA2. Also shown is the background signal obtained in the absence of any protein (-) or with the GST construct alone (GST). Data shown are mean±SEM.

Figure 2:
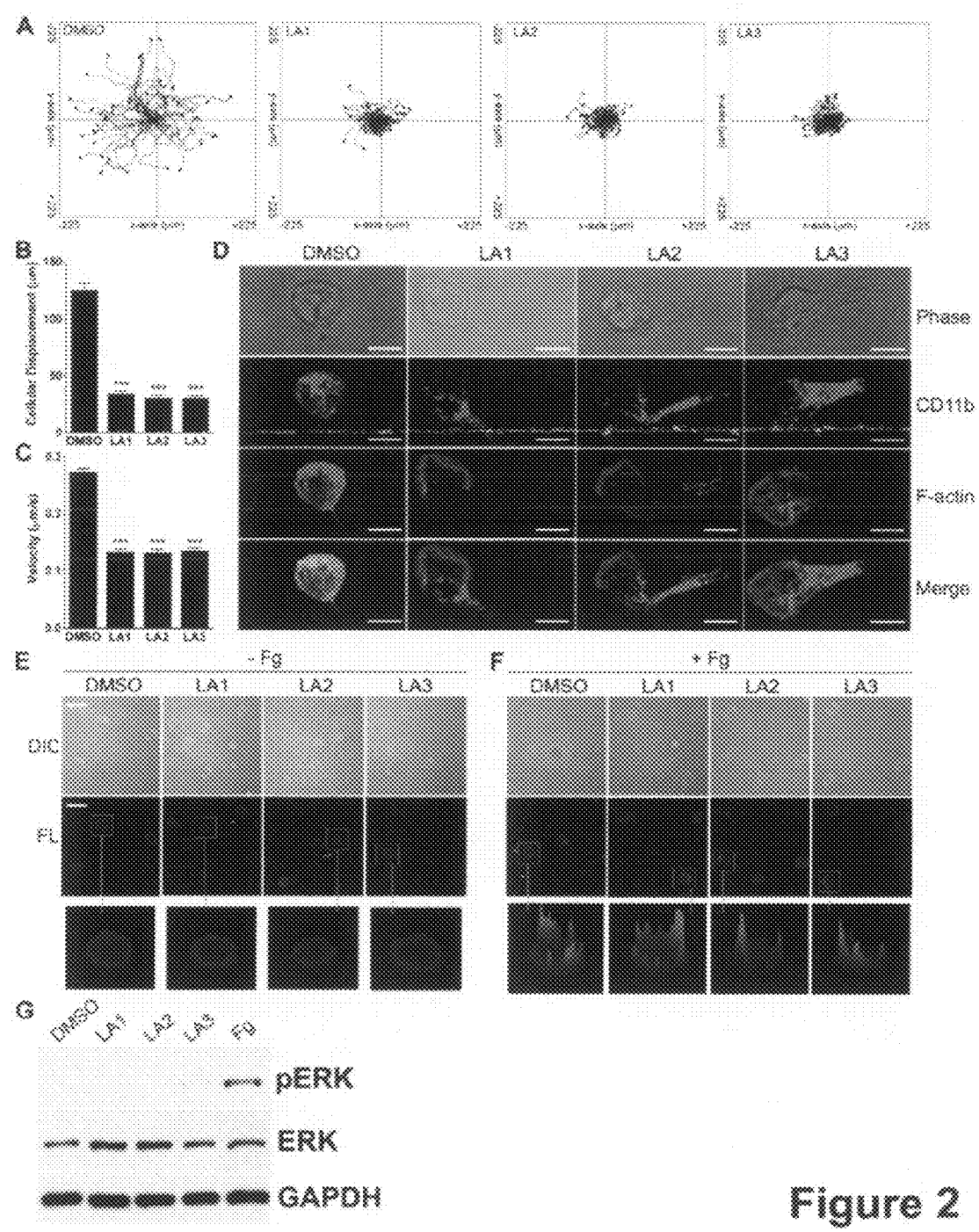

FIG. 2. Leukadherins affect cell migration, but do not mimic integrin ligands. A. Track plots showing analysis of migrating WT neutrophils in Zigmond chambers in response to an fMLP gradient and in the absence (DMSO) or presence of compounds LA1, LA2 and LA3. Time-lapse video microscopy images were taken every 30 seconds over a period of 30 min. >50 cells from at least four independent experiments were analyzed for each condition. B-C. Histograms showing total cellular displacement (B) and the cell migration velocity (C) of WT neutrophils chemotaxing as in A. Data shown are mean±SEM. ***P<0.001. D. Fluorescence images of CD11b localization in chemotaxing WT neutrophils in response to fMLP and in the absence (DMSO) or presence of LA1, LA2 and LA3. Representative confocal and phase contrast images of migrating neutrophils stained for CD11b (green) and F-actin (red) are shown. Scale bar represents 5 µm. E-F. Fluorescence images of CD11b clustering on K562 CD11b/CD18 cell surface. Cell suspensions were incubated with DMSO, LA1, LA2 or LA3 in the absence or presence of ligand Fg. Representative deconvolution and DIC images for cells stained for CD11b (Green) are shown. Also shown is a 3D representation of CD11b fluorescence intensity for selected cells, analyzed in ImageJ. Scale bar represents 20 µm. G. Analysis of CD11b/CD18 mediated outside-in signaling. K562 CD11b/CD18 cells were incubated with DMSO (control), LA1, LA2, LA3 or ligand Fg and the cell lysates were subsequently analyzed by 1D SDS-PAGE followed by western blot for phosphorylated ERK1/2 (pERK), total ERK1/2 and GAPDH.

Figure 3:
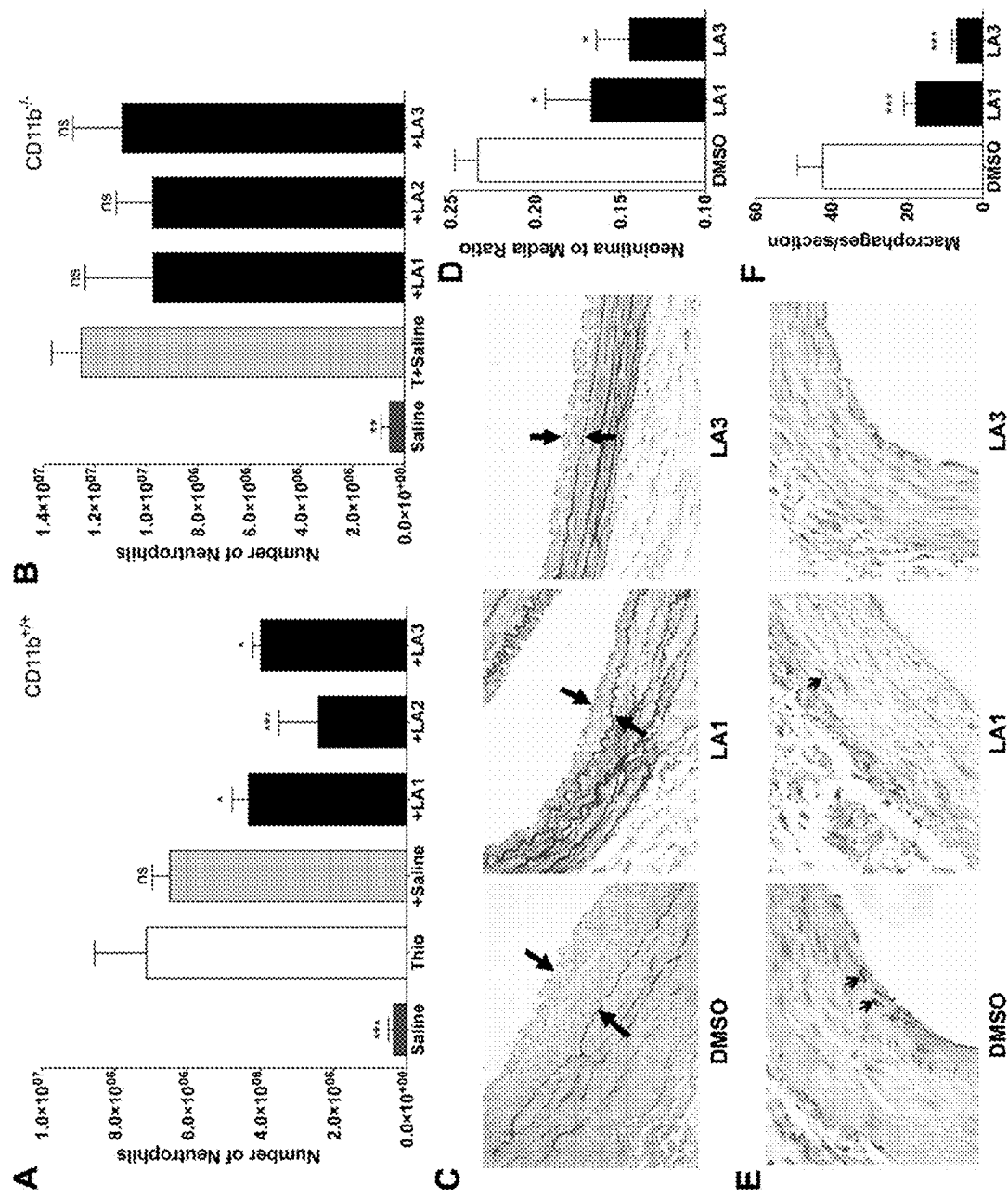

FIG. 3. Leukadherins decrease inflammatory recruitment of leukocytes in vivo. A-B. Bar graphs showing the total number of neutrophils in the peritoneal fluid of WT (A) or $CD11b^{-/-}$ (B) mice 4 h after intraperitoneal injection of thioglycollate from various treatment groups (thioglycollate alone or thioglycollate injection subsequent to administration of vehicle (saline), LA1, LA2 and LA3). Saline injection was used as a control (n=4-9 animals per group). Data shown are mean±SEM. *p<0.05, p<0.001, *p<0.0001, ns=not significant (one-way ANOVA). C. Representative photomicrographs of rat arteries 21 days after balloon injury from animals treated with vehicle (DMSO), LA1 or LA3. Arrows point to the neoinitmal thickening in each tissue. D. A bar graph showing the neointima to media ratio determined by morphometric analysis of the injured rat arteries from DMSO, LA1 and LA3 treated animals (n=7-9 animals per group). Data shown are mean±SEM. *p<0.05 (one-way ANOVA). E. Photomicrographs of representative rat arteries 3 days after balloon injury from animals treated with DMSO, LA1 and LA3. Arrows point to macrophage-specific CD68 immunostaining F. Bar graphs showing quantitation of macrophage infiltrates in injured at arteries (3 days post injury)

from animals treated with DMSO, LA1 and LA3 (n=12 animals per group). Data shown are mean±SEM. ***p<0.0001 (one-way ANOVA).

Figure 4:
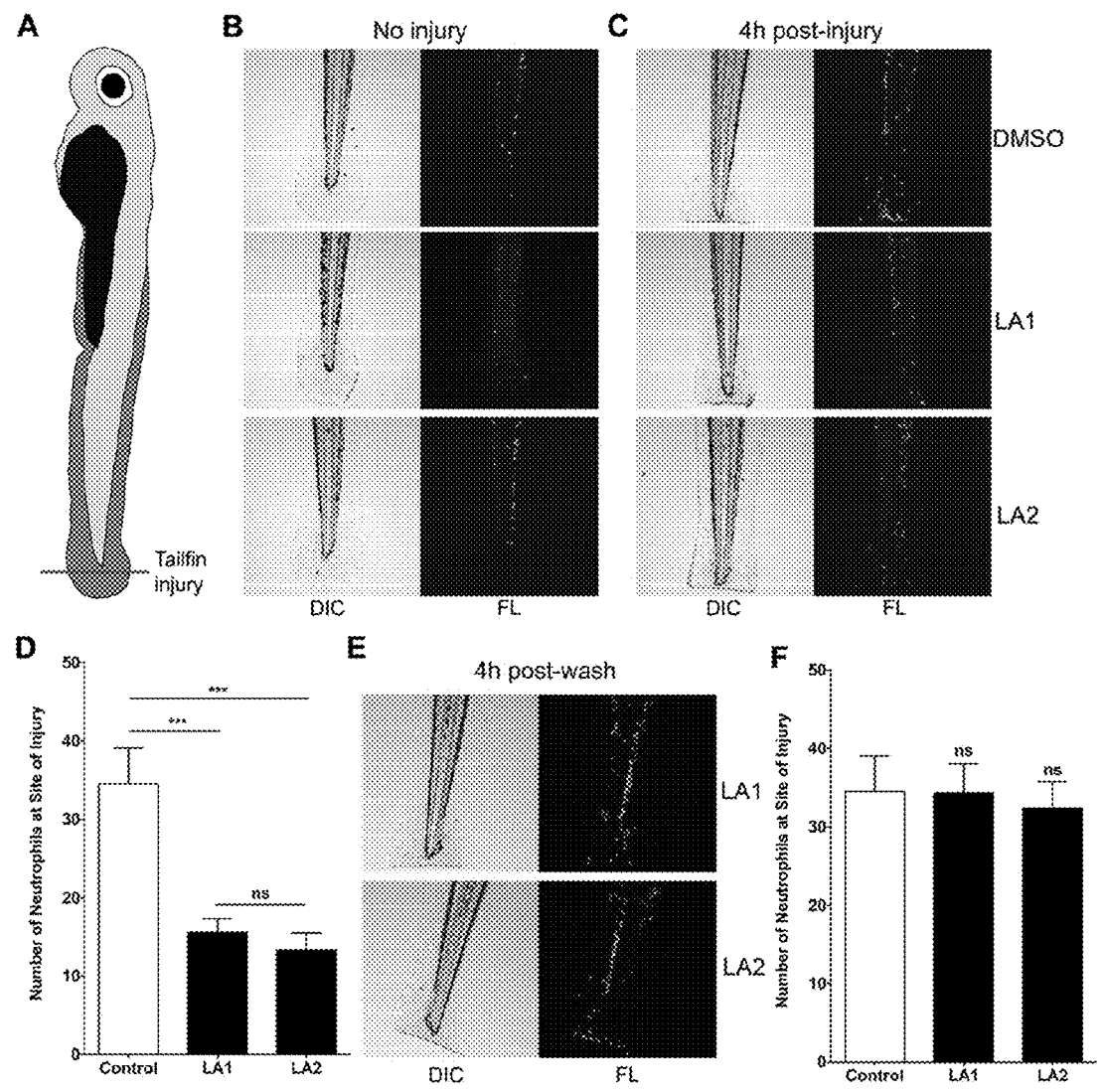

FIG. 4. Blockade of inflammatory neutrophil recruitment can be reversed by removal of leukadherins. A. Zebrafish tailfin injury model. B-C. Photomicrograph (left) and fluorescence images (right) of the 3dpf larvae tail without (B) and with injury (C). Representative images from zebrafish treated with vehicle (DMSO), LA1 and LA2 show neutrophil (green) accumulation in the tail. D. Bar graph showing quantitation of the number of neutrophils near the site of tailfin injury in zebrafish larvae treated with vehicle (Control), LA1 and LA2 (n=12-16 zebrafish larvae per group). Data shown are mean±SEM. ***p<0.0001 (one-way ANOVA). E. Representative photomicrograph (left) and fluorescence images (right) of the larvae tail showing neutrophil (green) accumulation in the tail 4 h after removal of compounds LA1 and LA2. F. Bar graph showing quantitation of the number of neutrophils near the site of tailfin injury 4 h after removal of LA1 and LA2 (n=8-12 larvae per group). Data shown are mean±SEM. ns=not significant (one-way ANOVA).

FIG. 5 shows that leukadherins reduce secretion of pro-inflammatory cytokines.

Figure 6:
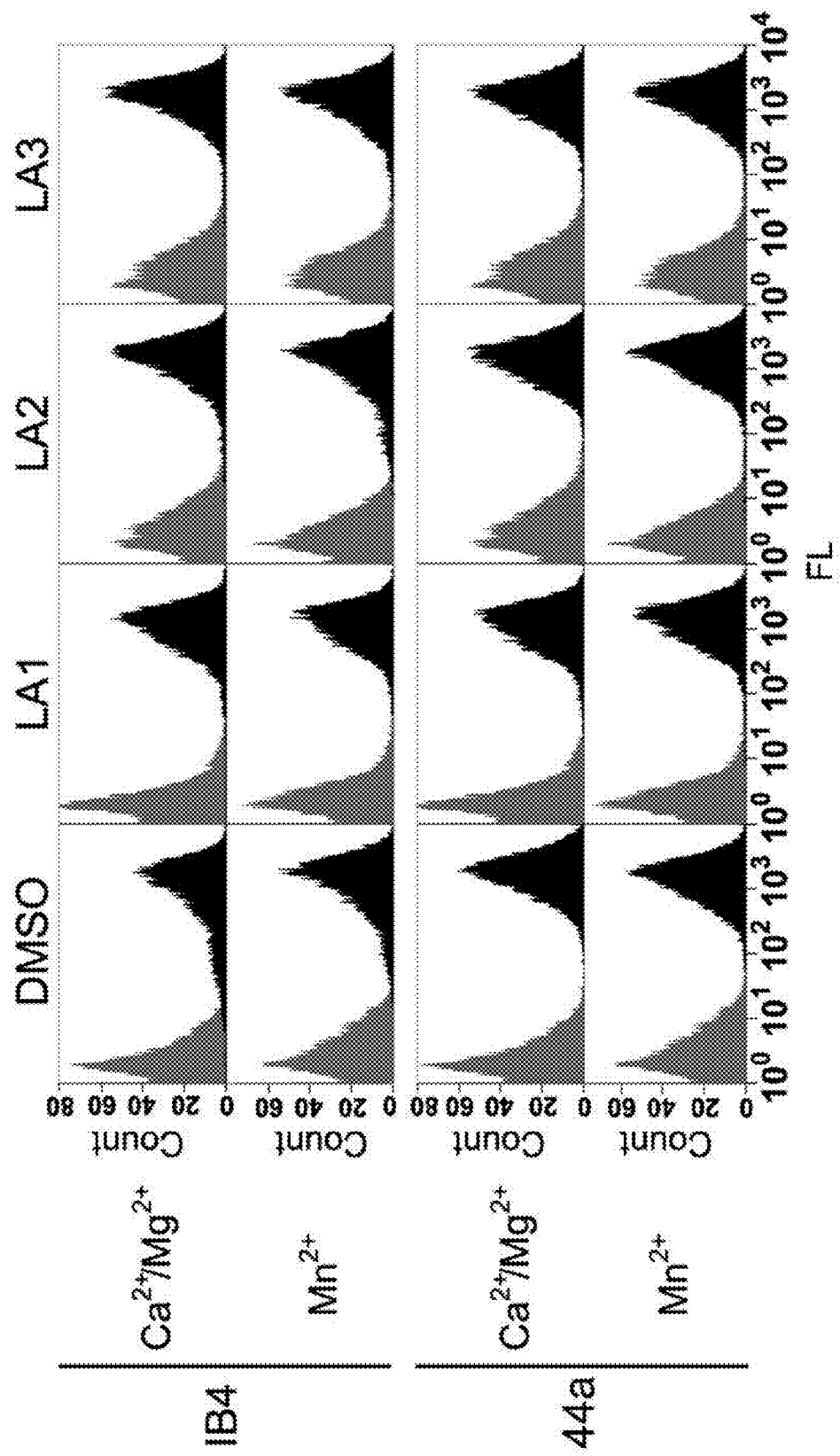

FIG. 6. Leukadherins do not affect surface CD11b/CD18 expression. FACS analysis showing level of CD11b/CD18 expression on the surface of live K562 CD11b/CD18 using mAbs IB4 and 44a (black) and isotype IgG2a control mAb (gray). Data shown are representative of at least three independent experiments.

Figure 7:
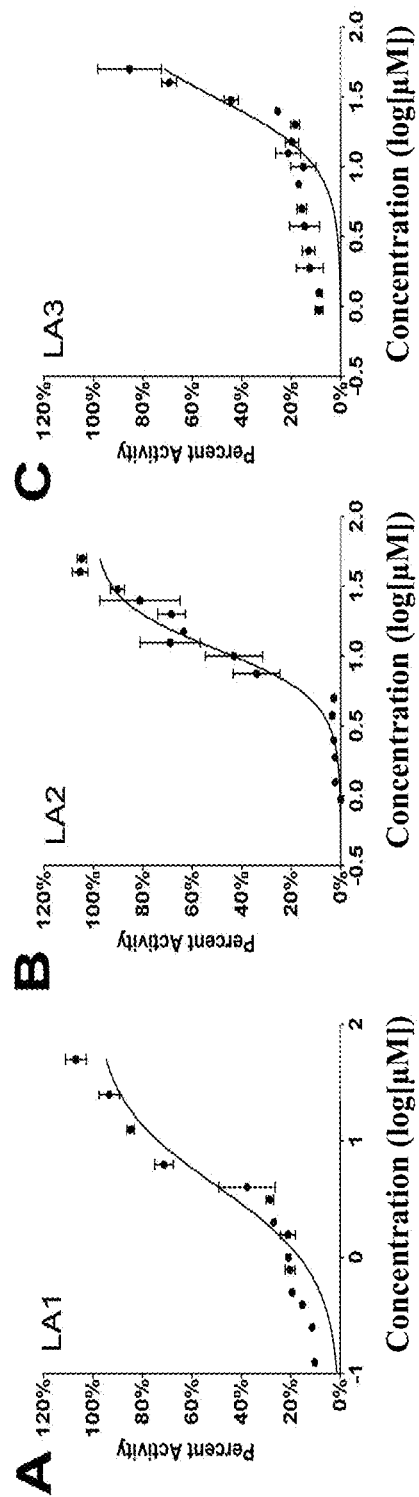

FIG. 7. Leukadherins increase binding of CD11b/CD18 to iC3b in a dose-dependent fashion. A-C. Dose-response curves showing percentage of input K562 CD11b/CD18 cells adhering to immobilized iC3b in the presence of increasing amounts of LA1 (A), LA2 (B) and LA3 (C). Data shown are mean±SEM from six independent wells and is representative of at least three independent experiments.

Figure 8:
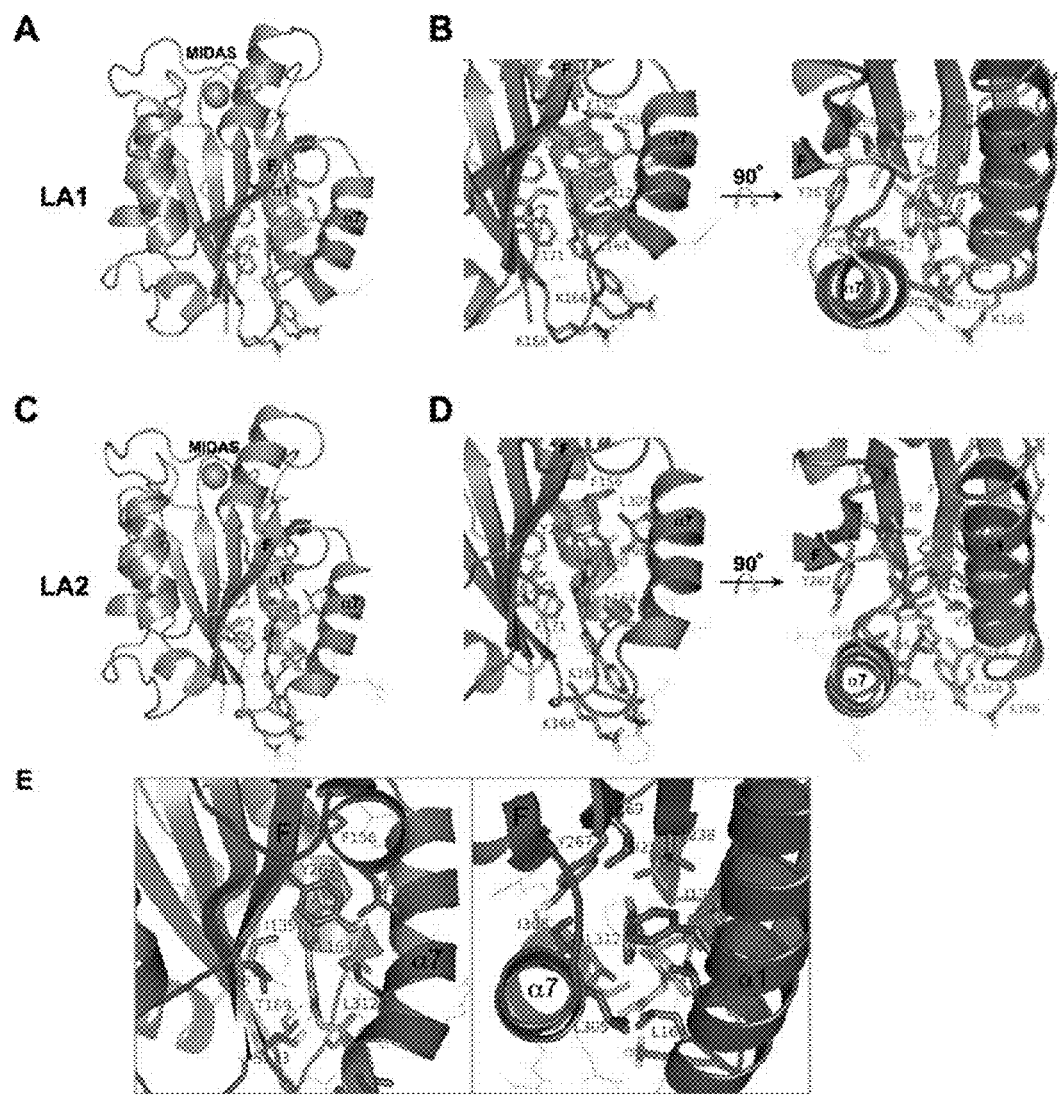

FIG. 8. Cartoon diagrams showing computational models for the binding of LA1-3 in an activation-sensitive region of the CD11b A-domain. A, C. A model of the αA-domain in its open conformation (copper ribbon) showing the docking of LA1 (green stick model) and LA2 (blue stick model) in the activation-sensitive F-α7 region. A metal ion at the MIDAS site is shown as a gray sphere. In agreement with studies with LA3 like compounds (E) [39], the leukadherins LA1 and LA2 were found to be oriented such that their most hydrophobic moieties interact with the hydrophobic pocket between helices α7 and α1 and the F-strand. Hydrophobic residues forming the binding pocket (highlighted) include α7 Leu305, Ile308 and Leu312, α1 Phe156, V160, Leu164, F-strand Tyr267, Ile269, as well as other hydrophobic pocket residues including Ile236, Val238, Ile135, Phe137, Phe171. The hydrophilic carboxylic acid moiety of the leukadherin compounds is oriented away from the hydrophobic pocket potentially forming ionic interactions with Lys166 and/or Lys168. B. Zoomed-in views of the activation-sensitive F-α7 region of the αA-domain (copper ribbon) from the docked structure (A). The two views are rotated by 90° with respect to each other. Interacting residues from the activation-sensitive hydrophobic region are shown as copper sticks and are labeled. Dashed lines highlight potential hydrogen bond interactions between LA1 and the αA-domain. D. Zoomed-in views of the activation-sensitive F-α7 region of the αA-domain (copper ribbon) from the docked structure (B). The two views are rotated by 90° with respect to each other. Interacting residues from the activation-sensitive hydrophobic region are shown as copper sticks and are labeled. Dashed lines highlight potential hydrogen bond interactions between LA2 and the αA-domain.

Figure 9:
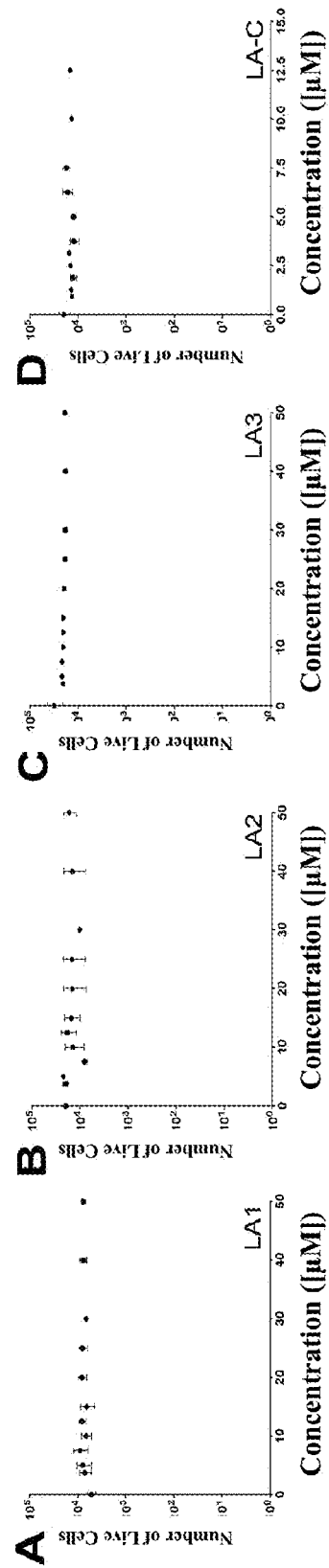

FIG. 9. Leukadherins show no cytotoxicity in vitro. K562 CD11b/CD18 cells were incubated at 37° C. in the presence of increasing amounts of LA1 (A), LA2 (B), LA3 (C) and LA-C (D) and the number of live cells were determined after 24 h. Data shown are mean±SEM from an assay done in triplicate and is representative of at least two independent experiments.

Figure 10:
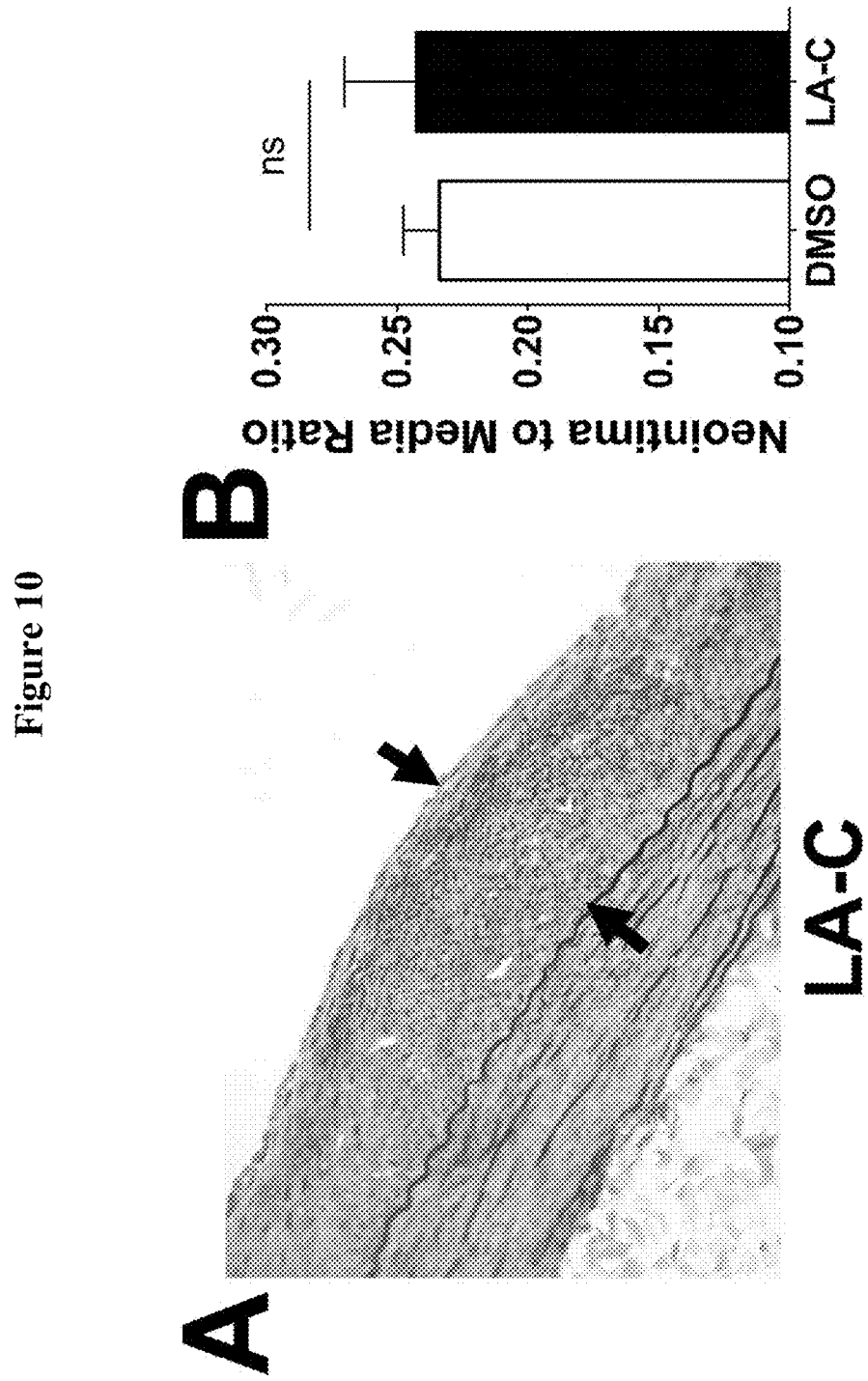

FIG. 10. Control compound (LA-C) has no effect on neointimal thickening upon balloon injury in WT rats. A. A representative photomicrograph of rat arteries 21 days after balloon injury from animals treated with control compound LA-C. Arrows point to the neoinitmal thickening in the artery. B. A bar graph showing the neointima to media ratio determined by morphometric analysis of the injured rat arteries from DMSO and LA-C treated animals (n=7-9 animals per group). Data shown are mean±SEM. ns=not significant (one-way ANOVA).

Figure 11:
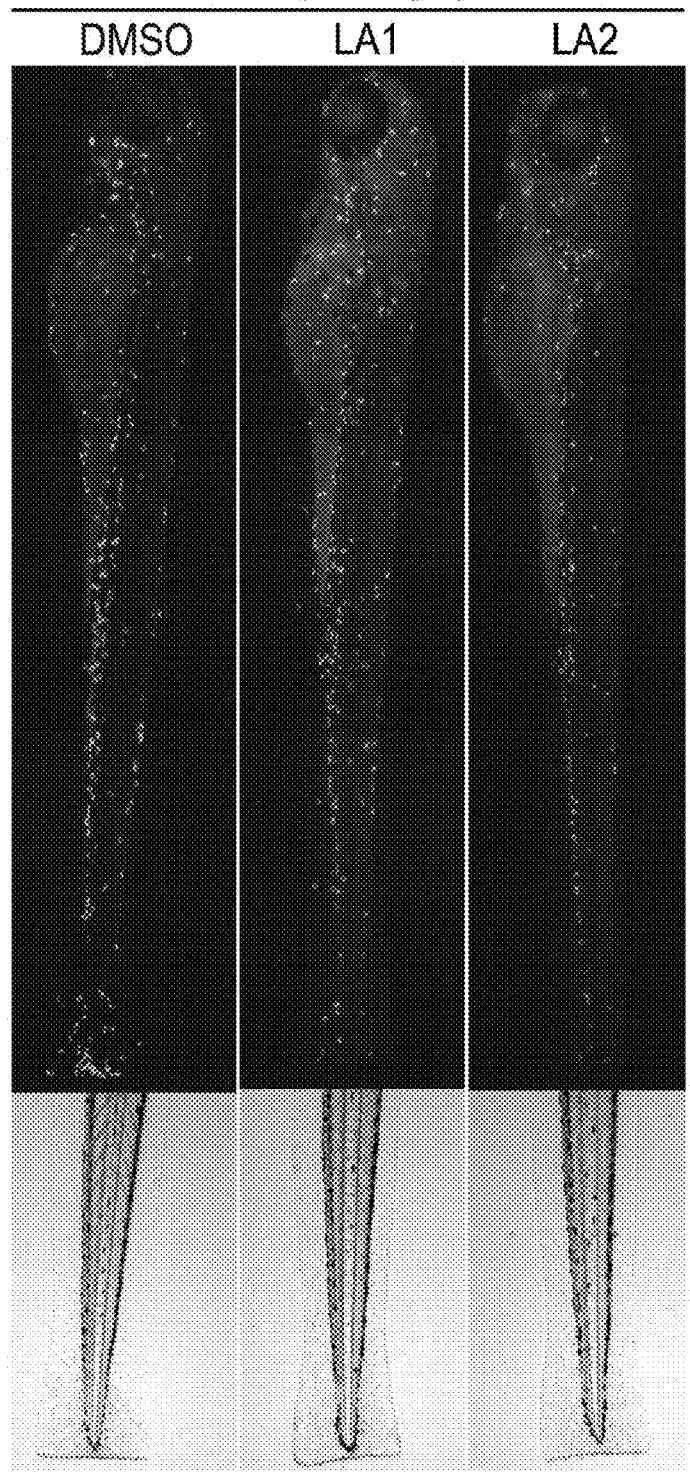

FIG. 11. Leukadherin treatment does not lead to loss of neutrophil cell number in zebrafish larvae. Representative fluorescence images of the whole 3 dpf zebrafish larvae (top) and photomicrographs of the tail (bottom) from injured fish show neutrophils (green) in each zebrafish larva. (n=12-16 zebrafish larvae per group). LA1 and LA2 treated zebrafish show slightly higher green background in the fluorescence image due to compound autofluorescence.

Figure 12:
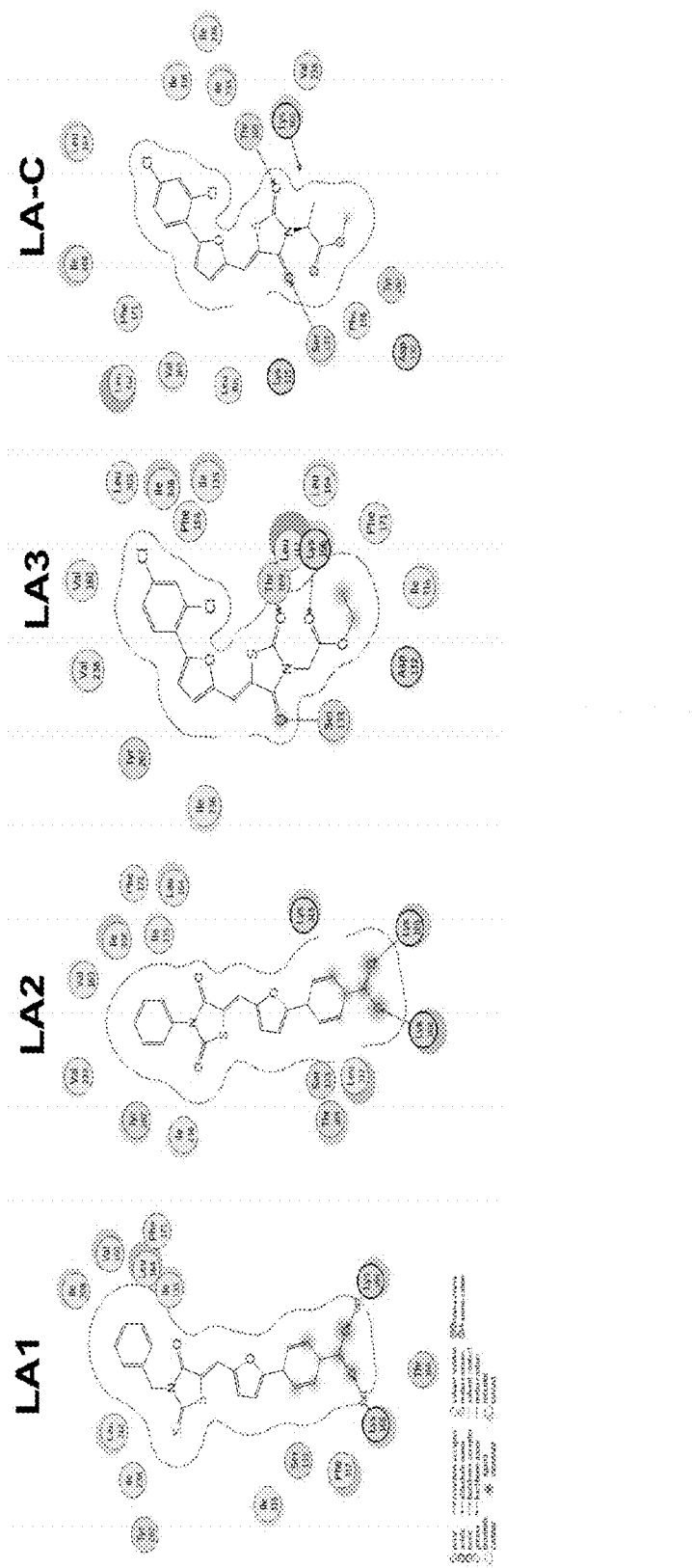

FIG. 12. Cartoon diagrams showing 2D projections from computational models for the binding of various leukadherins in an activation-sensitive region of the CD11b A-domain. The hydrophilic carboxylic acid moiety of the leukadherin compounds is oriented away from the hydrophobic pocket potentially forming ionic interactions with Lys166 and/or Lys168.

FIG. 13 shows Table S1. White blood cell count in mouse whole blood samples (n=2-5 animals), ns=not significant.

DETAILED DESCRIPTION OF THE INVENTION

One aspect of the invention relates to a compound of Formula (I)

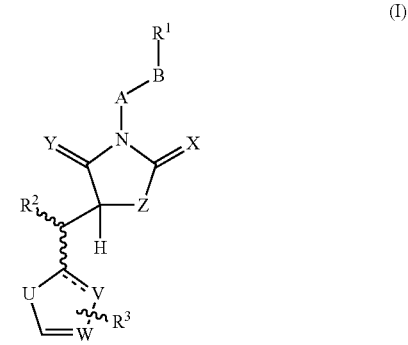

wherein
A is absent or is selected from alkyl and alkenyl;
B is absent or is selected from alkyl, alkenyl, O, S and $NR^4$;
N is nitrogen;
X and Y are independently selected from O and S;
Z is selected from $CR^4$, O, S and $NR^4$;
U, V and W are independently selected from $CR^4$, O, S and $NR^4$;

R$^1$ and R$^3$ are independently selected from acyl, alkyl, alkenyl, alkynyl, hydroxyalkyl, aminoalkyl, thioalkyl, aryl, aralkyl, carboxyaryl, alkoxyalkyl, alkoxyaryl, alcoxycarbonylaryl, aminoaryl, amidoaryl, haloaryl, heteroaryl, heteroaralkyl, carbocyclyl, heterocyclyl, heterocyclylalkyl, alkoxycarbonyl, alkylaminocarbonyl, alkylthiocarbonyl, sulfonate, alkylsulfonate, arylsulfonate, sulfone, alkylsulfone, arylsulfone, sulfoxide, alkylsulfoxide, arylsulfoxide, alkylsulfonamide, arylsulfonamide, and sulfonamide, piperidinyl, morpholinyl, pyrrolidinyl, phenyl, pyridyl, pyrimidinyl, furyl, thienyl, pyrrolyl, imidazolyl, triazolyl, pyrazolyl, thiazolyl, isoxazolyl, oxazolyl, oxadiazolyl, indolyl, naphthyl, quinolinyl, isoquinolinyl, quinoxalinyl, benzyl, benzofuryl, dibenzofuryl, benzthienyl, benzoxazolyl, benzothiazolyl, benzimidazolyl, pyridoimidazolyl, pyrimidoimidazolyl, pyridopyrazolyl, pyrazolopyrimidinyl, and any of which is optionally substituted with 1-6 independent substituents;

R$^2$ selected from hydrogen, alkyl, hydroxyalkyl, aminoalkyl, thioalkyl, alkoxyalkyl, aryl, aralkyl, heteroaryl, heteroaralkyl, carbocyclyl, carbocyclylalkyl, heterocyclyl, and heterocyclylalkyl; and R$^4$ is absent or is selected from hydrogen and alkyl.

In certain embodiments, Z is S.

In certain embodiments, X and Y are O. In certain other embodiments, X and Y are S. In certain other embodiments, X is S and Y is O. In certain other embodiments, X and Y are O and Z is S. In certain other embodiments, X, Y and Z are S. In certain other embodiments, X and Z are S and Y is O.

In certain embodiments, U is O and V and W are CR$^4$. In certain such embodiments, R$^4$ is hydrogen. In certain other embodiments, U is S and V and W are CR$^4$. In certain such embodiments, R$^4$ is hydrogen. In certain other embodiments, U is CR$^4$, V is N and W is O. In certain such embodiments, R$^4$ is hydrogen. In certain other embodiments, U is CR$^4$, V is O and W is N. In certain such embodiments, R$^4$ is hydrogen.

In certain embodiments, B is alkyl and A is absent. In certain such embodiments, R$^1$ is selected from alkoxycarbonyl, aryl, heteroaryl, carbocyclyl, heterocyclyl and alkoxycarbonyl. In certain embodiments, B is methylene and A is absent. In certain such embodiments, R$^1$ is selected from alkoxycarbonyl, aryl, heteroaryl, carbocyclyl, heterocyclyl and alkoxycarbonyl. In certain such embodiments, B is methylene and A is absent.

In certain embodiments, where A is alkyl and B is absent, R$^1$ is alkoxycarbonyl.

In certain embodiments, A and B are both absent. In certain such embodiments, R$^1$ is selected from alkoxycarbonyl, aryl, heteroaryl, carbocyclyl, heterocyclyl and alkoxycarbonyl.

In certain embodiments, R$^1$ substituent is further substituted with 1-6 independent substituents.

In certain embodiments, R$^1$ is selected from furan, phenyl, benzyl, tetrahydrofuran, tetrahydrothiophene, pyrrolidine, tetrahydropyran, tetrahydrothiopyran, piperidine, piperazine, and morpholine. In certain embodiments R$^1$ is selected from tetrahydrofuran, tetrahydrothiophene, and pyrrolidine, preferably tetrahydrofuran.

In certain embodiments, R$^1$ is phenyl, preferably substituted phenyl. In certain such embodiments, R$^1$ is phenyl substituted one to five, preferably one to three, more preferably one or two times. In certain such embodiments, R$^1$ is phenyl substituted with one or two, preferably one substituent independently selected from halogen, nitro, cyano, hydroxyl, thiol, amino, alkoxy, alkylamino, alkylthio, hydroxyalkyl, alkoxyalkyl, aminoalkyl, thioalkyl, and alkyl, more preferably from alkyl and halogen, e.g., from methyl, fluoro and chloro.

In certain embodiments, R$^2$ is selected from hydrogen, alkyl, hydroxyalkyl, aminoalkyl, thioalkyl, alkoxyalkyl, aryl, aralkyl, heteroaryl, heteroaralkyl, carbocyclyl, carbocyclylalkyl, heterocyclyl, and heterocyclylalkyl.

In certain embodiments, R$^3$ is selected from alkyl, hydroxyalkyl, aminoalkyl, thioalkyl, alkoxyalkyl, aryl, aralkyl, heteroaryl, heteroaralkyl, carbocyclyl, carbocyclylalkyl, heterocyclyl, and heterocyclylalkyl. In certain embodiments, R$^2$ is hydrogen and R$^3$ is selected from aryl, aralkyl, heteroaryl, heteroaralkyl, carbocyclyl, carbocyclylalkyl, heterocyclyl, and heterocyclylalkyl, preferably aryl, heteroaryl, carbocyclyl, and heterocyclyl.

In certain embodiments, R$^3$ is heteroaryl selected from pyrrole, furan, pyrimidine, oxazole, isooxazole and thiophene, preferably furan. In certain embodiments, R$^3$ is furan substituted one to three, preferably one to two times, more preferably once. In certain such embodiments, R$^3$ is furan substituted once with a substituent selected from aryl, aralkyl, heteroaryl, heteroaralkyl, carbocyclyl, carbocyclylalkyl, heterocyclyl and heterocyclylalkyl, preferably aryl, heteroaryl, carbocyclyl, and heterocyclyl. In certain embodiments, R$^3$ is furan substituted once with an aryl group, which itself is optionally substituted, preferably one to two times with alkyl, carboxyl, alkoxycarbonyl and halogen, e.g., chlorophenyl, dichlorophenyl, carboxyphenyl.

In certain embodiments, R$^3$ is aryl, preferably phenyl. In certain such embodiments, R$^3$ is phenyl substituted with one or two, preferably two substituents independently selected from halogen, nitro, cyano, hydroxyl, thiol, amino, alkoxy, alkylamino, alkylthio, hydroxyalkyl, alkoxyalkyl, aminoalkyl, thioalkyl, and alkyl. In certain such embodiments, R$^3$ is phenyl substituted once with a halogen, preferably bromo.

One aspect of the invention relates to a compound of Formula (II)

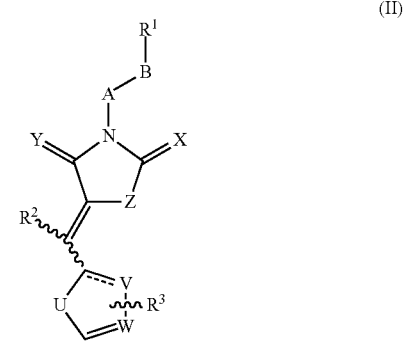

(II)

wherein

A is absent or is selected from alkyl and alkenyl;

B is absent or is selected from alkyl, alkenyl, O, S and NR$^4$;

N is nitrogen;

X and Y are independently selected from O and S;

Z is selected from CR$^4$, O, S and NR$^4$;

U, V and W are independently selected from CR$^4$, O, S and NR$^4$;

R$^1$ and R$^3$ are independently selected from acyl, alkyl, alkenyl, alkynyl, hydroxyalkyl, aminoalkyl, thioalkyl, aryl, aralkyl, carboxyaryl, alkoxyalkyl, alkoxyaryl, alcoxycarbonylaryl, aminoaryl, amidoaryl, haloaryl, heteroaryl, heteroaralkyl, carbocyclyl, heterocyclyl, heterocyclylalkyl, alkoxycarbonyl, alkylaminocarbonyl, alkylthiocarbonyl, sulfonate, alkylsulfonate, arylsulfonate, sulfone, alkylsulfone, arylsulfone, sulfoxide, alkylsulfoxide, arylsulfoxide, alkylsulfonamide, arylsulfonamide, and sulfonamide, piperidinyl, morpholinyl, pyrrolidinyl, phenyl, pyridyl, pyrimidinyl, furyl, thienyl, pyrrolyl, imidazolyl, triazolyl, pyrazolyl, thiazolyl, isoxazolyl, oxazolyl, oxadiazolyl, indolyl, naphthyl, quinolinyl, isoquinolinyl, quinoxalinyl, benzyl, benzofuryl, dibenzofuryl, benzthienyl, benzoxazolyl, benzothiazolyl, benzimidazolyl, pyridoimidazolyl, pyrimidoimidazolyl, pyridopyrazolyl, pyrazolopyrimidinyl, and any of which is optionally substituted with 1-6 independent substituents;

$R^2$ selected from hydrogen, alkyl, hydroxyalkyl, aminoalkyl, thioalkyl, alkoxyalkyl, aryl, aralkyl, heteroaryl, heteroaralkyl, carbocyclyl, carbocyclylalkyl, heterocyclyl, and heterocyclylalkyl; and $R^4$ is absent or is selected from hydrogen and alkyl.

In certain embodiments, Z is S.

In certain embodiments, X and Y are O. In certain other embodiments, X and Y are S. In certain other embodiments, X is S and Y is O. In certain other embodiments, X and Y are O and Z is S. In certain other embodiments, X, Y and Z are S. In certain other embodiments, X and Z are S and Y is O.

In certain embodiments, U is O and V and W are $CR^4$. In certain such embodiments, $R^4$ is hydrogen. In certain other embodiments, U is S and V and W are $CR^4$. In certain such embodiments, $R^4$ is hydrogen. In certain other embodiments, U is $CR^4$, V is N and W is O. In certain such embodiments, $R^4$ is hydrogen. In certain other embodiments, U is $CR^4$, V is O and W is N. In certain such embodiments, $R^4$ is hydrogen.

In certain embodiments, B is alkyl and A is absent. In certain such embodiments, $R^1$ is selected from alkoxycarbonyl, aryl, heteroaryl, carbocyclyl, heterocyclyl and alkoxycarbonyl. In certain embodiments, B is methylene and A is absent. In certain such embodiments, $R^1$ is selected from alkoxycarbonyl, aryl, heteroaryl, carbocyclyl, heterocyclyl and alkoxycarbonyl. In certain such embodiments, B is methylene and A is absent.

In certain embodiments, where A is alkyl and B is absent, $R^1$ is alkoxycarbonyl.

In certain embodiments, A and B are both absent. In certain such embodiments, $R^1$ is selected from alkoxycarbonyl, aryl, heteroaryl, carbocyclyl, heterocyclyl and alkoxycarbonyl.

In certain embodiments, $R^1$ substituent is further substituted with 1-6 independent substituents.

In certain embodiments, $R^1$ is selected from furan, phenyl, benzyl, tetrahydrofuran, tetrahydrothiophene, pyrrolidine, tetrahydropyran, tetrahydrothiopyran, piperidine, piperazine, and morpholine. In certain embodiments $R^1$ is selected from tetrahydrofuran, tetrahydrothiophene, and pyrrolidine, preferably tetrahydrofuran.

In certain embodiments, $R^1$ is phenyl, preferably substituted phenyl. In certain such embodiments, $R^1$ is phenyl substituted one to five, preferably one to three, more preferably one or two times. In certain such embodiments, $R^1$ is phenyl substituted with one or two, preferably one substituent independently selected from halogen, nitro, cyano, hydroxyl, thiol, amino, alkoxy, alkylamino, alkylthio, hydroxyalkyl, alkoxyalkyl, aminoalkyl, thioalkyl, and alkyl, more preferably from alkyl and halogen, e.g., from methyl, fluoro and chloro.

In certain embodiments, $R^2$ is selected from hydrogen, alkyl, hydroxyalkyl, aminoalkyl, thioalkyl, alkoxyalkyl, aryl, aralkyl, heteroaryl, heteroaralkyl, carbocyclyl, carbocyclylalkyl, heterocyclyl, and heterocyclylalkyl.

In certain embodiments, $R^3$ is selected from alkyl, hydroxyalkyl, aminoalkyl, thioalkyl, alkoxyalkyl, aryl, aralkyl, heteroaryl, heteroaralkyl, carbocyclyl, carbocyclylalkyl, heterocyclyl, and heterocyclylalkyl. In certain embodiments, $R^2$ is hydrogen and $R^3$ is selected from aryl, aralkyl, heteroaryl, heteroaralkyl, carbocyclyl, carbocyclylalkyl, heterocyclyl, and heterocyclylalkyl, preferably aryl, heteroaryl, carbocyclyl, and heterocyclyl.

In certain embodiments, $R^3$ is heteroaryl selected from pyrrole, furan, pyrimidine, oxazole, isooxazole and thiophene, preferably furan. In certain embodiments, $R^3$ is furan substituted one to three, preferably one to two times, more preferably once. In certain such embodiments, $R^3$ is furan substituted once with a substituent selected from aryl, aralkyl, heteroaryl, heteroaralkyl, carbocyclyl, carbocyclylalkyl, heterocyclyl and heterocyclylalkyl, preferably aryl, heteroaryl, carbocyclyl, and heterocyclyl. In certain embodiments, $R^3$ is furan substituted once with an aryl group, which itself is optionally substituted, preferably one to two times with alkyl, carboxyl, alkoxycarbonyl and halogen, e.g., chlorophenyl, dichlorophenyl, carboxyphenyl.

In certain embodiments, $R^3$ is aryl, preferably phenyl. In certain such embodiments, $R^3$ is phenyl substituted with one or two, preferably two substituents independently selected from halogen, nitro, cyano, hydroxyl, thiol, amino, alkoxy, alkylamino, alkylthio, hydroxyalkyl, alkoxyalkyl, aminoalkyl, thioalkyl, and alkyl. In certain such embodiments, $R^3$ is phenyl substituted once with a halogen, preferably bromo.

In certain embodiments, a compound of Formula II is selected from

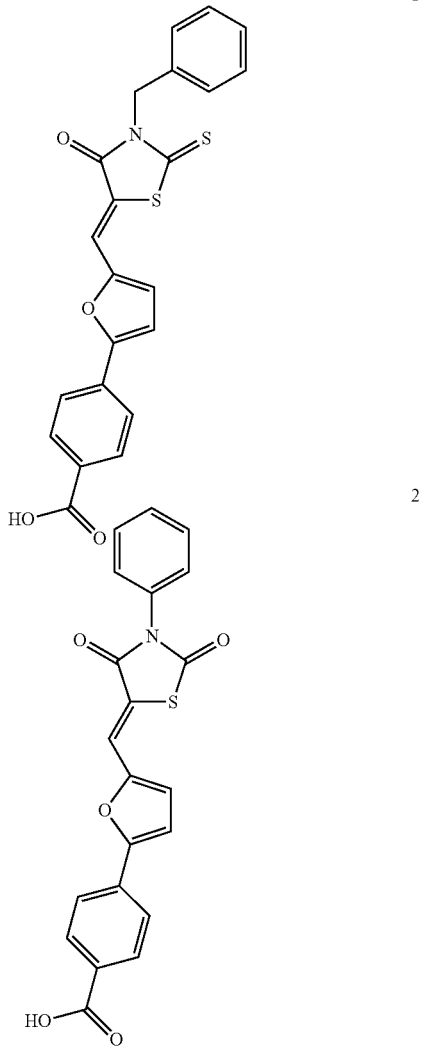

-continued
3
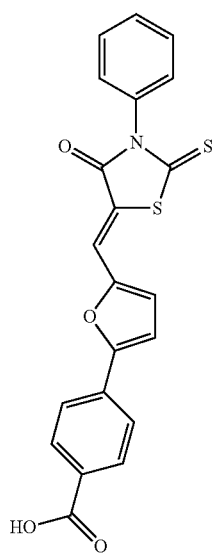
4
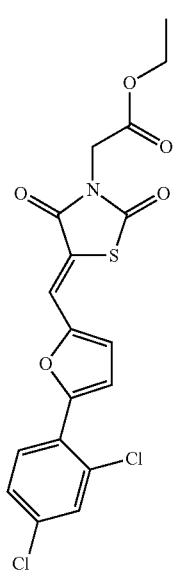
5
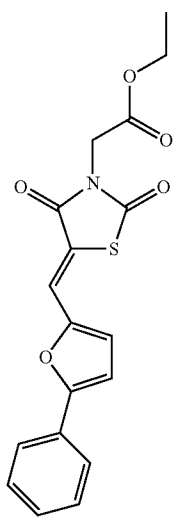
-continued
6
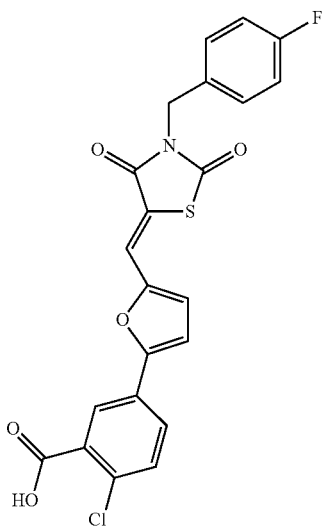
7
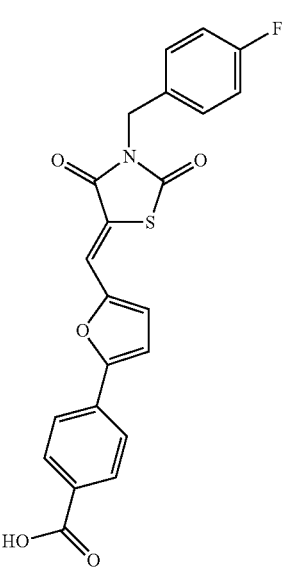
8
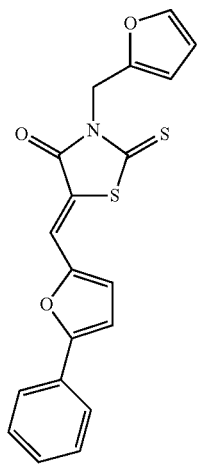

9
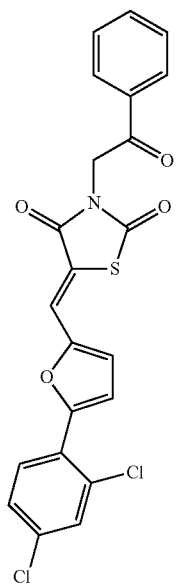
10
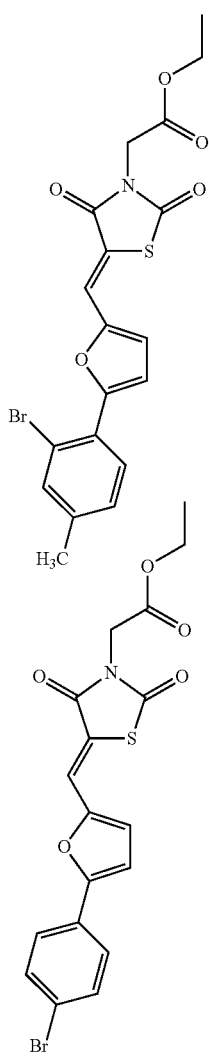
12
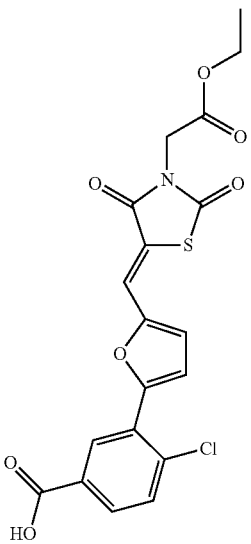
13
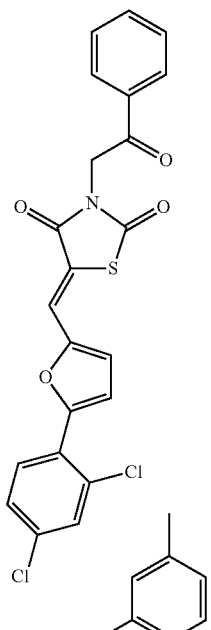
14
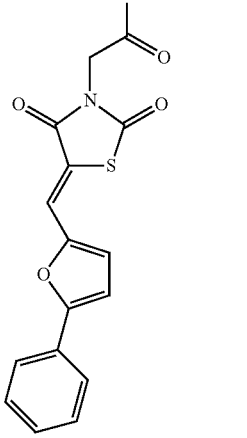
In certain embodiments, a compound of Formula II selected from the following compounds is less preferred 15
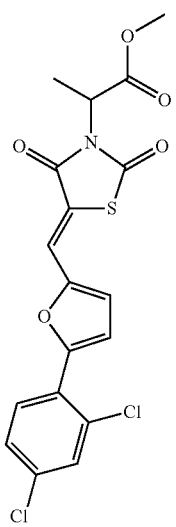
16
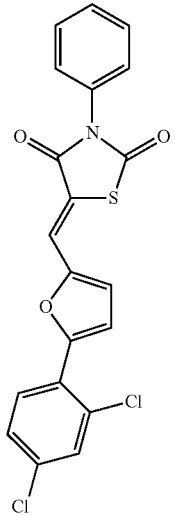
18
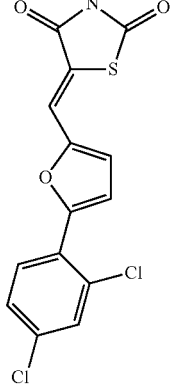
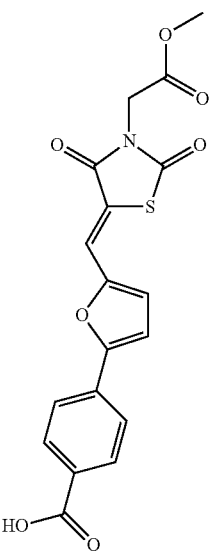
19
17
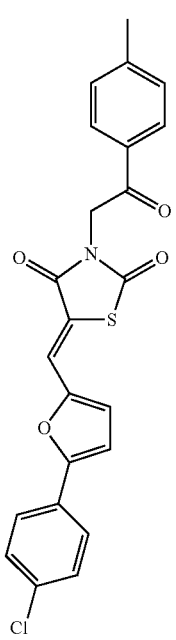
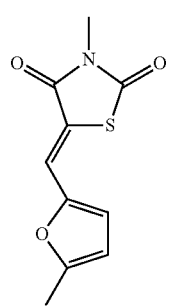
20

17
-continued
21
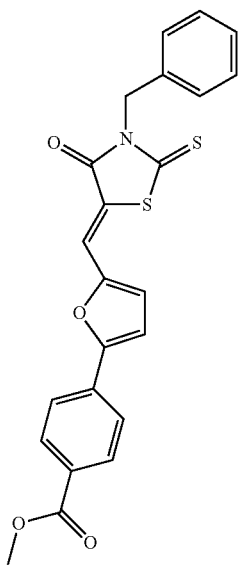
22
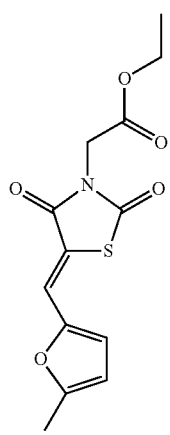
23
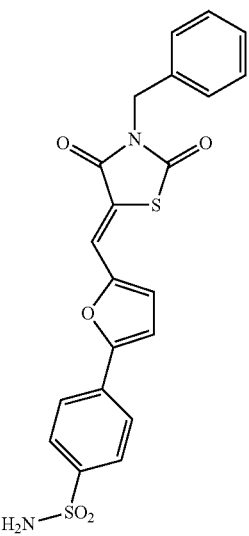
18
-continued
24
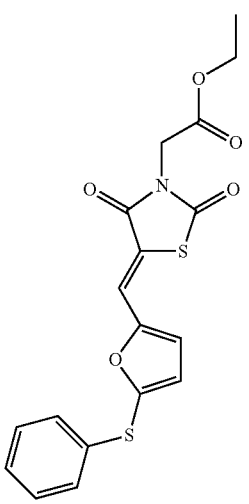
25
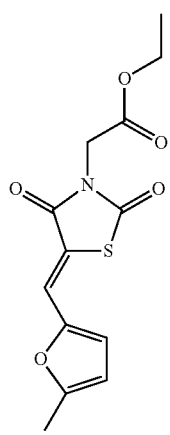
26
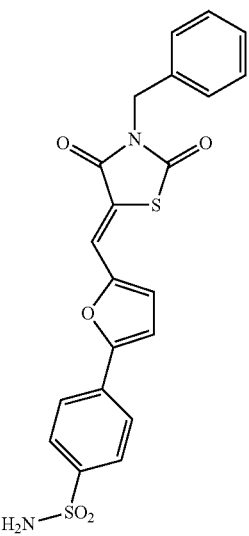

27 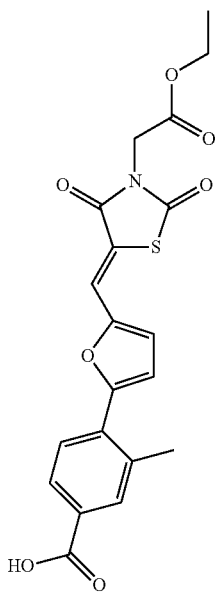

28 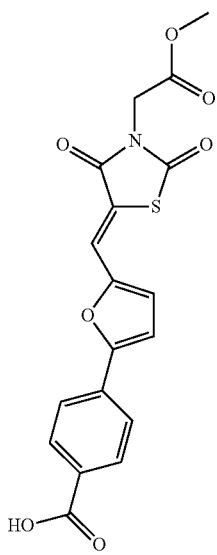

29 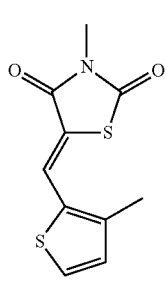

30 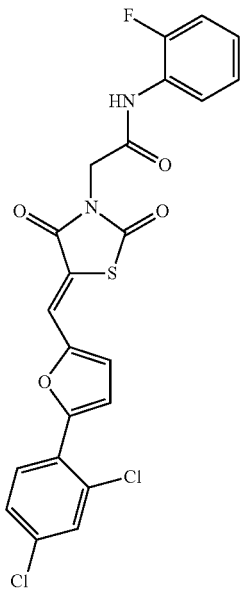

One aspect of the invention relates to a compound of Formula (III)

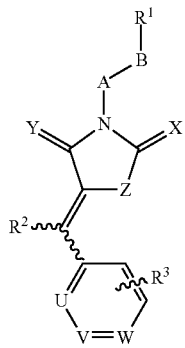

(III)

wherein
A is absent or is selected from alkyl and alkenyl;
B is absent or is selected from alkyl, alkenyl, O, S and $NR^4$;
N is nitrogen;
X and Y are independently selected from O and S;
Z is selected from $CR^4$, O, S and $NR^4$;
U, V and W are independently selected from $CR^4$, O, S and $NR^4$;
$R^3$ is 1-6 independent substituents present at position(s) 1-6 of the aryl ring;
$R^1$ and $R^3$ are independently selected from acyl, alkyl, alkenyl, alkynyl, hydroxyalkyl, aminoalkyl, thioalkyl, aryl, aralkyl, carboxyaryl, alkoxyalkyl, alkoxyaryl, alcoxycarbonylaryl, aminoaryl, amidoaryl, haloaryl, heteroaryl, heteroaralkyl, carbocyclyl, heterocyclyl, heterocyclylalkyl, alkoxycarbonyl, alkylaminocarbonyl, alkylthiocarbonyl, sulfonate, alkylsulfonate, arylsulfonate, sulfone, alkylsulfone, arylsulfone, sulfoxide, alkylsulfoxide, arylsulfoxide, alkylsulfonamide, arylsulfonamide, and sulfonamide, piperidinyl, morpholinyl, pyrrolidinyl, phenyl, pyridyl, pyrimidinyl, furyl, thienyl, pyrrolyl, imidazolyl, triazolyl, pyrazolyl, thiazolyl, isoxazolyl, oxazolyl, oxadiazolyl, indolyl, naphthyl, quinolinyl, isoquinolinyl, quinoxalinyl, benzyl, benzofuryl, dibenzofuryl, benzthienyl, benzoxazolyl, benzothiazolyl, benzimidazolyl, pyridoimidazolyl, pyrimidoimidazolyl, pyridopyrazolyl, pyrazolopyrimidinyl, and any of which is optionally substituted with 1-6 independent substituents;

$R^2$ selected from hydrogen, alkyl, hydroxyalkyl, aminoalkyl, thioalkyl, alkoxyalkyl, aryl, aralkyl, heteroaryl, heteroaralkyl, carbocyclyl, carbocyclylalkyl, heterocyclyl, and heterocyclylalkyl; and $R^4$ is absent or is selected from hydrogen and alkyl.

In certain embodiments, Z is S.

In certain embodiments, X and Y are O. In certain other embodiments, X and Y are S. In certain other embodiments, X is S and Y is O. In certain other embodiments, X and Y are O and Z is S. In certain other embodiments, X, Y and Z are S. In certain other embodiments, X and Z are S and Y is O.

In certain embodiments, U is N and V and W are $CR^4$. In certain such embodiments, $R^4$ is hydrogen. In certain other embodiments, V is N and U and W are $CR^4$. In certain such embodiments, $R^4$ is hydrogen. In certain other embodiments, W is N and V and V are $CR^4$. In certain such embodiments, $R^4$ is hydrogen.

In certain embodiments, B is alkyl and A is absent. In certain such embodiments, $R^1$ is selected from alkoxycarbonyl, aryl, heteroaryl, carbocyclyl, heterocyclyl and alkoxycarbonyl. In certain embodiments, B is methylene and A is absent. In certain such embodiments, $R^1$ is selected from alkoxycarbonyl, aryl, heteroaryl, carbocyclyl, heterocyclyl and alkoxycarbonyl. In certain such embodiments, B is methylene and A is absent.

In certain embodiments, where A is alkyl and B is absent, $R^1$ is alkoxycarbonyl.

In certain embodiments, A and B are both absent. In certain such embodiments, $R^1$ is selected from alkoxycarbonyl, aryl, heteroaryl, carbocyclyl, heterocyclyl and alkoxycarbonyl.

In certain embodiments, $R^1$ substituent is further substituted with 1-6 independent substituents.

In certain embodiments, $R^1$ is selected from furan, phenyl, benzyl, tetrahydrofuran, tetrahydrothiophene, pyrrolidine, tetrahydropyran, tetrahydrothiopyran, piperidine, piperazine, and morpholine. In certain embodiments $R^1$ is selected from tetrahydrofuran, tetrahydrothiophene, and pyrrolidine, preferably tetrahydrofuran.

In certain embodiments, $R^1$ is phenyl, preferably substituted phenyl. In certain such embodiments, $R^1$ is phenyl substituted one to five, preferably one to three, more preferably one or two times. In certain such embodiments, $R^1$ is phenyl substituted with one or two, preferably one substituent independently selected from halogen, nitro, cyano, hydroxyl, thiol, amino, alkoxy, alkylamino, alkylthio, hydroxyalkyl, alkoxyalkyl, aminoalkyl, thioalkyl, and alkyl, more preferably from alkyl and halogen, e.g., from methyl, fluoro and chloro.

In certain embodiments, $R^2$ is selected from hydrogen, alkyl, hydroxyalkyl, aminoalkyl, thioalkyl, alkoxyalkyl, aryl, aralkyl, heteroaryl, heteroaralkyl, carbocyclyl, carbocyclylalkyl, heterocyclyl, and heterocyclylalkyl.

In certain embodiments, $R^3$ is selected from alkyl, hydroxyalkyl, aminoalkyl, thioalkyl, alkoxyalkyl, aryl, aralkyl, heteroaryl, heteroaralkyl, carbocyclyl, carbocyclylalkyl, heterocyclyl, and heterocyclylalkyl. In certain embodiments, $R^2$ is hydrogen and $R^3$ is selected from aryl, aralkyl, heteroaryl, heteroaralkyl, carbocyclyl, carbocyclylalkyl, heterocyclyl, and heterocyclylalkyl, preferably aryl, heteroaryl, carbocyclyl, and heterocyclyl.

In certain embodiments, $R^3$ is heteroaryl selected from pyrrole, furan, pyrimidine, oxazole, isooxazole and thiophene, preferably furan. In certain embodiments, $R^3$ is furan substituted one to three, preferably one to two times, more preferably once. In certain such embodiments, $R^3$ is furan substituted once with a substituent selected from aryl, aralkyl, heteroaryl, heteroaralkyl, carbocyclyl, carbocyclylalkyl, heterocyclyl and heterocyclylalkyl, preferably aryl, heteroaryl, carbocyclyl, and heterocyclyl. In certain embodiments, $R^3$ is furan substituted once with an aryl group, which itself is optionally substituted, preferably one to two times with alkyl, carboxyl, alkoxycarbonyl and halogen, e.g., chlorophenyl, dichlorophenyl, carboxyphenyl.

In certain embodiments, $R^3$ is aryl, preferably phenyl. In certain such embodiments, $R^3$ is phenyl substituted with one or two, preferably two substituents independently selected from halogen, nitro, cyano, hydroxyl, thiol, amino, alkoxy, alkylamino, alkylthio, hydroxyalkyl, alkoxyalkyl, aminoalkyl, thioalkyl, and alkyl. In certain such embodiments, $R^3$ is phenyl substituted once with a halogen, preferably bromo.

One aspect of the invention relates to compounds described in this invention, their derivatives, pharmaceutically-acceptable salts or hydrates thereof.

One aspect of the invention relates to compounds 1-30, their derivatives or pharmaceutically-acceptable salts thereof.

In certain embodiments, the invention relates to a pharmaceutical composition comprising a compound of the invention or a pharmaceutically acceptable salt thereof and a pharmaceutically acceptable diluent, carrier, excipient or adjuvant.

In certain embodiments, the invention relates to a pharmaceutical composition comprising a compound of the invention or a pharmaceutically acceptable salt thereof in combination with another compound or agent to modulate or treat a condition and a pharmaceutically acceptable diluent, carrier, excipient or adjuvant.

Beta2 family of integrins, such as CD11b/CD18, are known targets in a number of mammalian diseases and conditions and there is considerable potential for agents that modulate the function of these integrins as therapeutic agents for the treatment of various mammalian diseases and conditions, including inflammatory conditions. Indeed, many agents that block binding of these integrins to their ligands (antagonists) have been previously described in the literature. However, such blocking agents have had little success in treating inflammatory/autoimmune diseases in humans [26, 28], and some have also shown unexpected side effects [32].

In certain aspects, the compounds of this invention, and their derivatives, are useful in promoting the function or activity of beta2 integrins, including CD11b/CD18. In certain aspects, the mechanism of action of the described compounds includes a direct binding of the compounds to the ligand binding αA- (or αI-) domain of beta2 integrins in a high-affinity conformation. In certain aspects, binding by the compounds of this invention to the αA-domain of beta2 integrins leads to a conversion of the αA-domain from an inactive to an active, ligand-competent conformation. In certain aspects, the binding by the compounds of this invention to the αA-domain of beta2 integrins leads to stabilization of the αA-domain into an active, ligand-competent conformation. In certain other aspects, the compounds of this invention bind very weakly to the αA-domain of beta2 integrins, when the αA-domain is in an inactive conformation. In certain aspects, binding by the compounds of this invention to beta2 integrins leads to a conversion of the integrin molecule from an inactive to an active, ligand-competent conformation. In certain aspects, the compounds do not compete with ligands for binding to their target beta2 integrins, bind in an allosteric pocket of the protein and allosterically regulate the protein function. Furthermore, in certain aspects, the compounds of this invention are not ligand mimics.

In one aspect of this invention, the compounds bind, with varying binding affinities, to all members of the beta2 integrin family, including CD11a/CD18, CD11b/CD18, CD11c/CD18 and CD11d/CD18. Thus, these compounds are useful in targeting all beta2 integrins and that the utility of these compounds and methods is not limited to a single type of integrin.

In certain aspects, integrin activation by the described compounds increases adhesion of integrin-expressing cells to extra-cellular matrix, ligands or other targets. In certain aspects, increased cell adhesivity reduces the lateral motility of cells (including cellular chemotaxis). In certain aspects, increased cell adhesivity reduces the transendothelial migration (TEM) of cells. In certain aspects, the compositions and methods described herein affect leukocyte recruitment. They can achieve this, for example, by increasing leukocyte slow rolling and adhesivity to the inflamed endothelium, which could be reversed with a blocking antibody. In certain aspects, the compositions and methods described herein reduce the levels of secreted factors. Such factors include, without limitation, inflammatory factors, for example TNFalpha, IL1beta, IL-6, IFNgamma, soluble uPAR, microparticles among others. In a related aspect, the compositions and methods described herein reduce the levels of secreted factors by integrin-expressing cells. In another aspect, the compositions and methods described herein reduce the levels of secreted factors by cells that interact with beta2 integrin expressing cells. In certain aspects, the compositions and methods described herein increase the level of secreted factors. Such factors include anti-inflammatory factors, for example IL-10 among others. In certain aspects, the compositions and methods described herein modify the signaling pathways in cells. In certain aspects, the compositions and methods described herein modify intracellular signaling pathways in beta2 integrin-expressing cells (including leukocytes, among others). Such pathways include, without limitation, the NF-kB pathway, AKT pathway, MAPK pathway, Toll-like receptor signaling pathway, cytokine receptor signaling pathways, among others. In certain aspects, the compounds and methods of this invention activate beta2 integrins, which induces intracellular signaling that synergizes or opposes other signaling pathways in the cells. In certain aspects, the compositions and methods described herein modify the signaling pathways in cells that interact with the beta2-integrin expressing cells. Such cells include other leukocyte subsets, lymphocytes, endothelial cells, among others. In certain other aspects, the compositions and methods described herein modify the signaling pathways in cells that interact with factors secreted by the beta2-integrin expressing cells (such as leukocytes, lymphocytes, endothelial cells, among others).

In certain embodiments, the compounds of the invention regulate the function of beta2 integrins, especially integrin CD11b/CD18.

In certain embodiments, the compounds of the invention regulate conformation of beta2 integrins, especially integrin CD11b/CD18.

In certain embodiments, the compounds of the invention regulate the organization of beta2 integrins in a cell, especially integrin CD11b/CD18. In certain such embodiments, the organization of beta2 integrins includes its dimerization or multimurization with itself or other proteins and substances.

In certain embodiments, the compounds of the invention regulate the organization of beta2 integrins on a cell membrane, especially integrin CD11b/CD18. In certain such embodiments, the organization of beta2 integrins includes its dimerization or multimurization with itself or other proteins and substances.

In certain embodiments, the compounds of the invention increase the binding of beta2 integrins, especially integrin CD11b/CD18, to its ligands.

In certain embodiments, the compounds of the invention increase the binding of beta2 integrins, especially integrin CD11b/CD18, to its ligands, wherein the ligand is independently selected from ICAM-1, ICAM-2, ICAM-3, iC3b, fibrinogen, Factor X, fibrin, uPAR and GP Ibalpha.

In certain embodiments, the compounds of the invention increase the binding of beta2 integrins, especially integrin CD11b/CD18, to its ligands, wherein binding of the compound with the protein modulates at least one function normally associated with binding of a natural ligand of the protein. In certain embodiments, the function is independently selected from the group consisting of rolling of leukocytes with vascular endothelium, binding of leukocytes with vascular endothelium, crawling of leukocytes with vascular endothelium, translocation of leukocytes through vascular endothelium, infiltration of leukocytes into intimal tissue, release of one or more soluble factors from leukocytes, release of a chemotactic factor from leukocytes, release of a growth factor from leukocytes, leukocyte-binding-associated release of a chemotactic factor from a tissue, leukocyte-binding-associated release of a growth factor from a tissue, leukocyte-binding-associated release of one or more soluble factors from a tissue, change in the level of one or more soluble factors in circulation and change in the level of one or more insoluble factors.

In certain embodiments, the compounds of the invention modulate function of cells in vitro or in vivo. In certain such embodiments, the function is independently selected from the group consisting of rolling of leukocytes with vascular endothelium, binding of leukocytes with vascular endothelium, crawling of leukocytes with vascular endothelium, translocation of leukocytes through vascular endothelium and infiltration of leukocytes into intimal tissue. In certain other embodiments, the function is independently selected from the group consisting of release of one or more secreted factors from leukocytes, release of a chemotactic factor from leukocytes, release of a growth factor from leukocytes, leukocyte-binding-associated release of a chemotactic factor from a tissue, leukocyte-binding-associated release of a growth factor from a tissue, leukocyte-binding-associated release of one or more soluble factors from a tissue, change in the level of one or more soluble factors in circulation and change in the level of one or more insoluble factors. In certain such embodiments, the secreted factors include cytokines. In certain such embodiments, the cytokines include pro-inflammatory cytokines. In certain other embodiments, the cytokines include anti-inflammatory cytokines. In certain other embodiments, the cytokines include, but not limited to, IL-1beta, IL-6 and IL-10. In certain other embodiments, the soluble factors include, but not limited to, TNFalpha and interferon gamma.

In certain embodiments, the compounds of the invention modulate biological function in vitro or in vivo. In certain such embodiments, the biological function is independently selected from the group consisting of gene expression, epigenetic profile, protein expression, protein levels, protein modifications, post-translational modifications and signaling. In certain such embodiments, the compounds of the invention modulate biological function in leukocytes. In certain other embodiments, the compounds of the invention modulate biological function in other cells. In certain other embodiments, the compounds of the invention modulate biological function in tissues.

In certain embodiments, the invention relates to methods for the regulation of the function of beta2 integrins, especially integrin CD11b/CD18, comprising administering a compound of the invention.

In certain embodiments, the invention relates to methods for the regulation of the conformation of beta2 integrins, especially integrin CD11b/CD18, comprising administering a compound of the invention.

In certain embodiments, the invention relates to methods for the regulation of the organization of beta2 integrins in a cell, especially integrin CD11b/CD18, comprising administering a compound of the invention. In certain such embodiments, the organization of beta2 integrins includes is dimerization or multimurization with itself or other proteins and substances.

In certain embodiments, the invention relates to methods for the regulation of the organization of beta2 integrins on a cell membrane, especially integrin CD11b/CD18, comprising administering a compound of the invention. In certain such embodiments, the organization of beta2 integrins includes is dimerization or multimurization with itself or other proteins and substances.

In certain embodiments, the invention relates to methods for increasing the binding of beta2 integrins, especially integrin CD11b/CD18, to its ligands comprising administering a compound of the invention.

In certain embodiments, the invention relates to methods for increasing the binding of beta2 integrins, especially integrin CD11b/CD18, to its ligands comprising administering a compound of the invention, wherein the ligand is independently selected from ICAM-1, ICAM-2, ICAM-3, iC3b, fibrinogen, Factor X, fibrin, uPAR and GP Ibalpha.

In certain embodiments, the invention relates to methods for increasing the binding of beta2 integrins, especially integrin CD11b/CD18, to its ligands comprising administering a compound of the invention, wherein binding of the compound with the protein modulates at least one function normally associated with binding of a natural ligand of the protein. In certain embodiments, the function is independently selected from the group consisting of rolling of leukocytes with vascular endothelium, binding of leukocytes with vascular endothelium, crawling of leukocytes with vascular endothelium, translocation of leukocytes through vascular endothelium, infiltration of leukocytes into intimal tissue, release of one or more soluble factors from leukocytes, release of a chemotactic factor from leukocytes, release of a growth factor from leukocytes, leukocyte-binding-associated release of a chemotactic factor from a tissue, leukocyte-binding-associated release of a growth factor from a tissue, leukocyte-binding-associated release of one or more soluble factors from a tissue, change in the level of one or more soluble factors in circulation and change in the level of one or more insoluble factors.

In certain embodiments, the invention relates to methods for modulating function of cells in vitro or in vivo comprising of administering a compound of the invention. In certain such embodiments, the function is independently selected from the group consisting of rolling of leukocytes with vascular endothelium, binding of leukocytes with vascular endothelium, crawling of leukocytes with vascular endothelium, translocation of leukocytes through vascular endothelium and infiltration of leukocytes into intimal tissue. In certain other embodiments, the function is independently selected from the group consisting of release of one or more soluble factors from leukocytes, release of a chemotactic factor from leukocytes, release of a growth factor from leukocytes, leukocyte-binding-associated release of a chemotactic factor from a tissue, leukocyte-binding-associated release of a growth factor from a tissue, leukocyte-binding-associated release of one or more secreted factors from a tissue, change in the level of one or more soluble factors in circulation and change in the level of one or more insoluble factors. In certain such embodiments, the soluble factors include cytokines. In certain such embodiments, the cytokines include pro-inflammatory cytokines. In certain other embodiments, the cytokines include anti-inflammatory cytokines. In certain other embodiments, the cytokines include, but not limited to, IL-1beta, IL-6 and IL-10. In certain other embodiments, the soluble factors include, but not limited to, TNFalpha and interferon gamma.

In certain embodiments, the invention relates to methods for modulating biological function in vitro or in vivo comprising of administering a compound of the invention. In certain such embodiments, the biological function is independently selected from the group consisting of gene expression, epigenetic profile, protein expression, protein levels, protein modifications, post-translational modifications and signaling. In certain such embodiments, the compounds of the invention modulate biological function in leukocytes. In certain other embodiments, the methods of the invention modulate biological function in other cells. In certain other embodiments, the methods of the invention modulate biological function in tissues.

In certain aspects, the invention includes compositions and methods to optimize the in vivo half life of the compounds of this invention, or their derivatives.

In certain embodiments, the invention relates to a composition for use on an article, such as a catheter or a stent, comprising administering an effective amount of any compound of the invention, or a derivative thereof, to the article. In certain embodiments, the invention relates to a composition for use on an article for a patient, comprising administering an effective amount of any compound of the invention, or a derivative thereof, to the article.

In certain embodiments, the invention relates to a drug-eluting stent media; wherein said drug-eluting stent media comprises a pharmaceutical composition; wherein said pharmaceutical composition comprises a compound of the invention or a pharmaceutically acceptable salt thereof and optionally a pharmaceutically acceptable diluent, carrier, excipient or adjuvant.

In certain embodiments, the invention relates to a composition comprising a drug-eluting stent media; wherein said drug-eluting stent media comprises a pharmaceutical composition; wherein said pharmaceutical composition comprises a compound of the invention or a pharmaceutically acceptable salt thereof and optionally a pharmaceutically acceptable diluent, carrier, excipient or adjuvant.

In certain embodiments, the invention relates to a method of improving health of a patient, comprising administering an article comprising an effective amount of any compound of the invention, or a derivative thereof, to the patient.

In certain embodiments, the invention relates to a compound or method of improving health of a patient, comprising administering an article comprising an effective amount of any compound of the invention, or a derivative thereof, to a cell, tissue or organ of the patient, wherein the administration is performed in vivo or ex vivo.

In certain embodiments, the compounds and methods of this invention have no systemic vascular toxicity and do not induce injury or apoptosis in vascular cells.

In certain embodiments, the invention relates to a pharmaceutical composition useful in treating a disease or condition associated with the activity of beta2 integrins. In certain embodiments, such a disease or condition is selected from inflammation (including, but not limited to, acute and chronic inflammation), inflammatory skin diseases, immune-related disorders, autoimmune diseases, burn, immune deficiency, acquired immune deficiency syndrome (AIDS), myeloperoxidase deficiency, Wiskott-Aldrich syndrome, chronic kidney disease, chronic granulomatous disease, hyper-IgM syndromes, leukocyte adhesion deficiency, iron deficiency, Chediak-Higashi syndrome, severe combined immunodeficiency, diabetes, obesity, hypertension, HIV, wound-healing, remodeling, scarring, fibrosis, stem cell therapies, cachexia, encephalomyelitis, multiple schlerosis, psoriasis, lupus, rheumatoid arthritis, immune-related disorders, radiation injury, transplantation, cell transplantation, cell transfusion, organ transplantation, organ preservation, cell preservation, asthma, irritable bowel disease, irritable bowel syndrome, ulcerative colitis, colitis, bowel disease, cancer, leukemia, ischemia-reperfusion injury, stroke, neointimal thickening associated with vascular injury, bullous pemphigoid, neonatal obstructive nephropathy, familial hypercholesterolemia, atherosclerosis, dyslipidemia, aortic aneurisms, arteritis, vascular occlusion, including cerebral artery occlusion, complications of coronary by-pass surgery, myocarditis, including chronic autoimmune myocarditis and viral myocarditis, heart failure, including chronic heart failure (CHF), cachexia of heart failure, myocardial infarction, stenosis, restenosis after heart surgery, silent myocardial ischemia, post-implantation complications of left ventricular assist devices, thrombophlebitis, vasculitis, including Kawasaki's vasculitis, giant cell arteritis, Wegener's granulomatosis, traumatic head injury, post-ischemic-reperfusion injury, post-ischemic cerebral inflammation, ischemia-reperfusion injury following myocardial infarction and cardiovascular disease, and wherein the pharmaceutical composition comprises a pharmaceutically acceptable carrier, diluent or excipient and a compound of the invention. In certain such embodiments, the invention relates to a pharmaceutical composition useful in treating a disease or condition associated with the activity of beta2 integrins such as inflammatory kidney disease, a condition that affects millions of people in the world and leads to renal failure, and restenosis, a common problem in people who have undergone angioplasty, one of the most common procedures in interventional cardiology. In certain such embodiments, the beta2 integrin is CD11b/CD18.

In one aspect, the compounds and methods of this invention are useful in treating cancer or reducing tumors in patients. In one related aspect, the compounds and methods of this invention modulate tumor infiltration of leukocytes. For example, tumors also secrete inflammatory cytokines to recruit cells expressing beta2 integrins, such as CD11b/CD18, to facilitate neovascularization [10]. During cancer treatments, including via chemotherapy and irradiation, tumors recruit large numbers of specific leukocytes or bone marrow-derived cells that restore tumor vasculature and allow tumor re-growth and recurrence [11]. In one aspect, the compounds and methods of this invention are useful in reducing activity, such as infiltration, of such cells. In another aspect, the compounds and methods of this invention are useful in enhancing the response of other cancer treatments, such as chemotherapy, antibody therapy and irradiation [11].

In certain embodiments, the invention relates to methods for treating a disease or condition selected from inflammation (including, but not limited to, acute and chronic inflammation), inflammatory skin diseases, immune-related disorders, autoimmune diseases, burn, immune deficiency, acquired immune deficiency syndrome (AIDS), myeloperoxidase deficiency, Wiskott-Aldrich syndrome, chronic kidney disease, chronic granulomatous disease, hyper-IgM syndromes, leukocyte adhesion deficiency, iron deficiency, Chediak-Higashi syndrome, severe combined immunodeficiency, diabetes, obesity, hypertension, HIV, wound-healing, remodeling, scarring, fibrosis, stem cell therapies, cachexia, encephalomyelitis, multiple schlerosis, psoriasis, lupus, rheumatoid arthritis, immune-related disorders, radiation injury, transplantation, cell transplantation, cell transfusion, organ transplantation, organ preservation, cell preservation, asthma, irritable bowel disease, irritable bowel syndrome, ulcerative colitis, colitis, bowel disease, cancer, leukemia, ischemia-reperfusion injury, stroke, neointimal thickening associated with vascular injury, bullous pemphigoid, neonatal obstructive nephropathy, familial hypercholesterolemia, atherosclerosis, dyslipidemia, aortic aneurisms, arteritis, vascular occlusion, including cerebral artery occlusion, complications of coronary by-pass surgery, myocarditis, including chronic autoimmune myocarditis and viral myocarditis, heart failure, including chronic heart failure (CHF), cachexia of heart failure, myocardial infarction, stenosis, restenosis after heart surgery, silent myocardial ischemia, post-implantation complications of left ventricular assist devices, thrombophlebitis, vasculitis, including Kawasaki's vasculitis, giant cell arteritis, Wegener's granulomatosis, traumatic head injury, post-ischemic-reperfusion injury, post-ischemic cerebral inflammation, ischemia-reperfusion injury following myocardial infarction and cardiovascular disease, comprising administering a compound of the invention.

Leukocyte recruitment precedes neointima formation and restenosis following percutaneous transluminal coronary angioplasty (PTCA) [5]. Denudation of the endothelial cell lining at the site of mechanical vascular injury leads to the deposition of fibrin and platelets, where selective binding between the platelet cell surface receptor GP Ibα and CD11b/CD18 expressed on the surface of leukocytes mediates the recruitment of leukocytes [40]. In certain aspects, the compositions and methods described herein decrease leukocyte recruitment upon injury, inflammation or other disease and condition in mammals. In certain aspects, the compositions and methods described herein reduce organ injury, including neointimal hyperplasia upon arterial injury. In certain other aspects, the compositions and methods described herein preserved organ function upon acute organ injury, such as ischemia-reperfusion injury. For example, the compounds preserve kidney function upon acute kidney injury. In certain aspects, the compositions and methods described herein preserved kidney function upon glomerular nephritis or nephrosis. In certain aspects, the compositions and methods described herein modulate the function of inflammatory cells, such as lymphocytes and leukocytes. For example, the compositions and methods described herein induce graft tolerance in the recipient animal. Similarly, the compositions and methods described herein reduce graft-vs-host disease in the recipient animal. Thus, in certain aspects, the compositions and methods described herein improve transplantation outcomes.

In one aspect, the compounds and methods of this invention are useful in inducing graft tolerance in patients. In one related aspect, the grafts include bone marrow, bone marrow cells, stem cells, immune cells, engineered cells, organs, tissues or other cells. In another related aspect, the grafts include one or more of bone marrow, bone marrow cells, stem cells, immune cells, engineered cells, organs, tissues or other cells.

In certain embodiments, the invention relates to a method of preventing or treating beta2 integrin (such as CD11b/CD18) mediated condition or disease in a patient comprising administering to said patient a therapeutically effective amount of a substantially pure and pharmaceutically acceptable compound of the invention.

In certain embodiments, the invention relates to a method of preventing or treating beta2 integrin (such as CD11b/CD18) expressing cell mediated condition or disease in a patient comprising administering to said patient a therapeutically effective amount of a substantially pure and pharmaceutically acceptable compound of the invention.

In certain embodiments, the invention relates to a method of detecting or diagnosing a beta2 integrin (such as CD11b/CD18) mediated condition or disease in a patient comprising administering to said patient a therapeutically effective amount of a substantially pure and pharmaceutically acceptable compound of the invention.

In certain embodiments, the invention relates to a method of detecting or diagnosing a beta2 integrin (such as CD11b/CD18) expressing cell mediated condition or disease in a patient comprising administering to said patient a therapeutically effective amount of a substantially pure and pharmaceutically acceptable compound of the invention.

In certain embodiments, the invention relates to the use of one or more compounds of the invention in an assay for the identification of modulators of beta2 integrins, especially CD11b/CD18.

In certain embodiments, the invention relates to the use of the described compounds in identification of sites and domains in beta2 integrins, especially integrin CD11b/CD18, CD11c/CD18, CD11d/CD18 and CD11a/CD18, that modulate activity of the said integrin. In certain other embodiments, the invention relates to the use of the described compounds in identification of related compounds that show selective binding for one or more of the beta2 integrins over other integrins.

In certain embodiments, the invention relates to the use of the described compounds in determining exact three-dimensional structure of the binding pocket in the target proteins, which can be used to derive more selective and/or potent binders. For example, a complex of CD11b/CD18 with a compound can be prepared and analyzed, e.g., by x-ray crystallography, nuclear magnetic resonance, or other suitable means, to identify the binding site of CD11b/CD18 that interacts with the compound.

In certain embodiments, computer-based modeling algorithms can be used to analyze the structures and conformations of compounds that bind beta2 integrins, especially CD11b/CD18, to identify structural features that contribute to successful binding. In certain embodiments, such information is analyzed in conjunction with information about the structure or conformation of CD11b/CD18 or a binding pocket thereof, such as structural information obtained by analysis of CD11b/CD18 using analytical techniques such as x-ray crystallography or nuclear magnetic resonance, to analyze interactions between binding compounds and the binding pocket they interact with. Such analysis can be used to predict the portion of, for example, CD11b/CD18 that interacts with the compound, to select compounds that possess structural features correlated with desired binding activity from a library of test compounds, or to design structures that are expected to exhibit binding with, for example, CD11b/CD18 for testing in vivo or in vitro using assays as described herein.

In certain embodiments, computer-based modeling algorithms can be used to identify novel compounds that bind beta2 integrins, especially CD11b/CD18, using structural features of the compounds of this invention. In certain embodiments, the methods used include scaffold hopping. In certain embodiments, the methods used include atom replacement, residue replacement and/or molecule replacement. In certain embodiments, such information is analyzed in conjunction with information about the structure or conformation of CD11b/CD18 or a binding pocket thereof, such as structural information obtained by analysis of CD11b/CD18 using analytical techniques such as x-ray crystallography or nuclear magnetic resonance, to analyze interactions between binding compounds and the binding pocket they interact with. Such analysis can be used to predict the portion of CD11b/CD18 that interacts with the compound, to select compounds that possess structural features correlated with desired binding activity from a library of test compounds, or to design structures that are expected to exhibit binding with CD11b/CD18 for testing in vivo or in vitro using assays as described herein.

One aspect relates to polarity of the compounds of the invention, wherein the compounds have an inherent end-to-end polarity such that compounds are more polar on one end of the molecule, for example on the top-end (N-substituted side of the thiazolidine ring) or the bottom-end (substituted furanyl side of the thiazolidine ring) as drawn, as compared to the other end of the molecule. In certain such embodiments, the compound of the invention is a compound of any one of Formulae I to III. In certain other embodiments, the compounds of the invention are selected from compounds 1-30 as designated above. In certain embodiments, compounds with two polar ends are dis-favored. In certain other embodiments, compounds 15-30 are less favored.

In certain embodiments, the compounds of the invention are in a pure or substantially pure single configuration. In certain such embodiments, the compounds have Z configuration. In certain such embodiments, the compound of the invention is a compound of any one of Formulae I to III. In certain other embodiments, the compounds of the invention are selected from compounds 1-30 as designated above. In certain other embodiments, compounds 15-30 are less favored.

In certain embodiments, the compounds of the invention occupy a binding pocket in αA-domain. In certain such embodiments, the αA-domain is from CD11b/CD18. In certain other embodiments, the αA-domain is from CD11aCD18. In yet other embodiments, the αA-domain is from CD11c/CD18. In yet another embodiment, the αA-domain is from CD11d/CD18. In certain embodiments, the compounds of the invention occupy a binding pocket in αA-domain in a manner similar to as described in FIGS. 8 and 12. In certain such embodiments, the compounds of the invention interact with polar residues of the amino acids of αA-domain. In certain other embodiments, the compounds of the invention interact with polar side-chains of the amino acids of αA-domain. In certain embodiments, the compounds of the invention interact with residue lysine 166 of αA-domain. In certain such embodiments, the more polar end of the compounds of the invention interacts with residue lysine 166 of αA-domain. In certain embodiments, the compounds of the invention interact with residue lysine 168 of αA-domain. In certain such embodiments, the more polar end of the compounds of the invention interacts with residue lysine 168 of αA-domain. In certain embodiments, the more non-polar end of the compounds of this invention occupies a hydrophobic pocket in the binding site in αA-domain. In certain embodiments, the more polar end of the compounds of this invention occupies a pocket in the binding site in αA-domain, such that the polar end is more exposed to the solvent.

In certain embodiments, compounds of the invention are useful in enhancing the function of beta2 integrins, especially integrin CD11b/CD18. In certain embodiments, compounds of the invention are useful in promoting activation of beta2 integrins, especially CD11b/CD18, by binding to the αA-domain of the protein. In certain embodiments, compounds of the invention are useful in modulating the function of beta2 integrin expressing cells, especially leukocytes. In certain embodiments, compounds of the invention are useful in treating a disease or condition, wherein the composition modulates the function of beta2 integrins, especially CD11b/CD18. In certain embodiments, compounds of the invention are useful in detecting or diagnosing a disease or condition, wherein the compound modulates the function of beta2 integrins, especially CD11b/CD18. In certain embodiments, compounds of the invention are useful on an article for a patient, comprising administering an effective amount of any compound of this invention, or a derivative thereof, to the article.

In certain embodiments, the invention relates to methods for modulating an immune response in a patient, comprising administering to the patient, in vivo or ex vivo, an effective amount of a compound of this invention, or a derivative thereof. In certain embodiments, the invention relates to methods for improving health of a patient, comprising administering to the patient, in vivo or ex vivo, an effective amount of a compound of this invention, or a derivative thereof. In certain embodiments, the invention relates to methods for modulating function of beta2 integrins, especially CD11b/CD18, comprising administering to the integrin expressing cell an effective amount of any compound of the invention, or a derivative thereof. In certain embodiments, the invention relates to methods for modulating function or activity of beta2 expressing cells, especially leukocytes, in vitro or in vivo, comprising administering to the integrin expressing cell an effective amount of any compound of the invention, or a derivative thereof. In certain embodiments, the invention relates to methods for modulating levels of secreted factors, in vitro or in vivo, comprising administering an effective amount of any compound of the invention, or a derivative thereof. In certain embodiments, the invention relates to methods for modulating organ function in a patient, comprising administering an effective amount of any compound of the invention, or a derivative thereof, in vivo or ex vivo. In certain embodiments, the invention relates to methods for improving health of a patient, comprising administering an article comprising an effective amount of any compound of the invention, or a derivative thereof. In certain embodiments, the invention relates to methods for detecting or diagnosing a disease or condition of a patient, comprising administering to the patient an effective amount of any compound of the invention, or a derivative thereof.

In certain such embodiments, the compound of the invention is a compound of any one of Formulae I to III. In certain such embodiments, the compound is selected from compounds 1-30 as designated above. In certain other embodiments, compounds 15-30 are less favored.

In certain embodiments, compounds of the invention are beta2 integrin, especially CD11b/CD18, agonists. In certain such embodiments, the compound of the invention is a compound of any one of Formulae I to III. In certain such embodiments, the compound is selected from compounds 1-30 as designated above. In certain other embodiments, compounds 15-30 are less favored.

In certain embodiments, the invention relates to methods for the modulation of integrin beta2, especially CD11b/CD18, comprising administering a compound of the invention. In certain such embodiments, the compound of the invention is a compound of any one of Formulae I to III. In certain embodiments, the invention relates to a method for modulating integrin CD11b/CD18 comprising administering a compound selected from compounds 1-30 as designated above. In certain other embodiments, compounds 15-30 are less favored.

In certain embodiments, the invention relates to methods for agonizing beta2 integrins, especially integrin CD11b/CD18, comprising administering a compound of the invention. In certain such embodiments, the compound of the invention is a compound of any one of Formulae I to III. In certain such embodiments, the compound of the invention is selected from compounds 1-30 as designated above. In certain other embodiments, compounds 15-30 are less favored.

Certain compounds of the present invention may exist in particular geometric or stereoisomeric forms. The present invention contemplates all such compounds, including cis- and trans-isomers, R- and S-enantiomers, diastereomers, (d)-isomers, (l)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers.

The present invention includes radiolabeled forms of compounds of the invention, for example, compounds of the invention labeled by incorporation within the structure $^3$H or $^{14}$C or a radioactive halogen such as $^{125}$I.

The present invention also includes labeled forms of compounds of the invention, for example, compounds of the invention labeled by linking the compound structure with biotin, with the help of a linker In certain embodiments, compounds of the invention, or derivatives thereof, can be used to detect or diagnose a condition or disease in a patient. In certain such embodiments, the compound of the invention is a compound of any one of Formulae I to III. In certain such embodiments, the compound is selected from compounds 1-30 as designated above.

In certain embodiments, compounds and compositions of the invention, or derivatives thereof, can be used in detecting or diagnosing an inflammatory disease or condition or an autoimmune disease or condition, comprising administering a compound of the invention or a derivative thereof, where the compound binds beta2 integrins, especially CD11b/CD18. In certain such embodiments, compounds and compositions of the invention, or derivatives thereof, preferably bind to active form of beta2 integrins, especially CD11b/CD18.

In certain embodiments, the invention relates to methods for detecting or diagnosing a condition or disease in a patient comprising of administering a compound of the invention, or a derivative thereof, to the patient.

In certain embodiments, the invention relates to methods for the identification of compounds or agents that modulate beta2 integrins, especially integrin CD11b/CD18. In certain embodiments, the invention relates to methods for the identification of biological function of compounds or agents that modulate integrin CD11b/CD18. In certain embodiments, the method includes a cell-adhesion-based high-throughput screening assay. In certain embodiments, the methods include in vitro and in vivo assays as described herein. While such methods and assays are demonstrated herein for identifying agonists of integrin CD11b/CD18, such methods and assays can be employed to identify compounds that inhibit or enhance cell adhesion mediated by other mechanisms as well, as will be recognized by those of skill in the art.

DEFINITIONS

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "$C_{x-y}$" when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The terms "amine" and "amino" are art-recognized and refer to both unsubstituted and substituted amines and salts thereof, e.g., a moiety that can be represented by

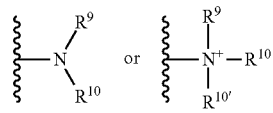

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The terms "carbocycle", "carbocyclyl", and "carbocyclic", as used herein, refers to a non-aromatic saturated or unsaturated ring in which each atom of the ring is carbon. Preferably a carbocycle ring contains from 3 to 10 atoms, more preferably from 5 to 7 atoms.

The term "carbocycloalkyl", as used herein, refers to an alkyl group substituted with a carbocycle group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The term "heteroaralkyl", as used herein, refers to an alkyl group substituted with a hetaryl group.

The term "heteroaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocycloalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "a cell" as used herein includes a plurality of cells. Administering a compound to a cell includes in vivo, ex vivo, and in vitro administration.

To "enhance" or "promote" a function or activity, such as binding of integrin to its ligand or adhesion of cell to matrix or cell proliferation, is to increase the function or activity when compared to otherwise same conditions except for a condition or parameter of interest, or alternatively, as compared to another condition(s).

The term "modulate" as used herein includes the inhibition or suppression of a function or activity (such as cell proliferation) as well as the enhancement of a function or activity.

The term "agonist" is art-recognized. In certain embodiments, the term includes compounds and compositions that enhance or promote a function or activity (such as integrin binding to its ligand or conversion of integrin from inactive state to active state or phosphorylation of an intracellular protein).

The term "secreted factor" is art-recognized. In certain embodiments, the term includes proteins, peptides, small molecules, ions, lipids and microparticles that are released by a cell. In certain related embodiments, the term includes cytokines, chemokines, small molecules (such as cyclic AMP) and ions that are released by a cell.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use. Each carrier must be "acceptable" in the sense of being compatible with other ingredients of the formulation and not injurious to the patient.

Some examples of materials which can serve as pharmaceutically acceptable carriers include (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salt" means an acid addition salt or a basic addition salt which is suitable for or compatible with the treatment of patients.

The term "pharmaceutically acceptable acid addition salt" as used herein means any non-toxic organic or inorganic salt of any base compounds represented by Formula I or II. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of Formula I or II are more soluble in water and various hydrophilic organic solvents, and generally demonstrate higher melting points in comparison to their free base forms. The selection of the appropriate salt will be known to one skilled in the art. Other non-pharmaceutically acceptable salts, e.g. oxalates, may be used, for example, in the isolation of compounds of Formula I or II for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by Formula I or II or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "solvate" as used herein means a compound of Formula I or II, or a pharmaceutically acceptable salt of a compound of Formula I or II, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate".

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The compositions containing the compounds of the invention can be prepared by known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

The compounds of this invention may be used in the form of the free base, in the form of salts, solvates and as hydrates. All forms are within the scope of the invention. Acid addition salts may be formed and provide a more convenient form for use; in practice, use of the salt form inherently amounts to use of the base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial properties inherent in the free base are not vitiated by side effects ascribable to the anions. Although pharmaceutically acceptable salts of the basic compounds are preferred, all acid addition salts are useful as sources of the free base form even if the particular salt per se is desired only as an intermediate product as, for example, when the salt is formed only for the purposes of purification and identification, or when it is used as an intermediate in preparing a pharmaceutically acceptable salt by ion exchange procedures.

Pharmaceutically acceptable salts within the scope of the invention include those derived from the following acids; mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like.

In accordance with the methods of the invention, the described compounds or salts or solvates thereof may be administered to a patient in a variety of forms depending on the selected route of administration, as will be understood by those skilled in the art. The compositions of the invention may be administered orally or parenterally. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

A compound of the invention or a salt or solvate thereof may be orally administered, for example, with an inert diluent or with an assimilable edible carder, or it may be enclosed in hard or soft shell gelatin capsules, or it may be compressed into tablets, or it may be incorporated directly with the food of the diet. For oral therapeutic administration, the compound of the invention may be incorporated with excipient and used in the form of ingestible tablets, buccal tablets, troches, capsules, elixirs, suspensions, syrups, wafers, and the like.

A compound of the invention may also be administered parenterally or intraperitoneally. Solutions of a compound of the invention as a free base or pharmacologically acceptable salt or solvate can be prepared in water suitably mixed with a surfactant such as hydroxypropylcellulose. Dispersions can also be prepared in glycerol, liquid polyethylene glycols, DMSO, and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (1990—18th edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringeability exists.

The compounds of the invention may be administered to an animal alone or in combination with pharmaceutically acceptable carriers, as noted above, the proportion of which is determined by the solubility and chemical nature of the compound, chosen route of administration and standard pharmaceutical practice.

The dosage of the compounds and/or compositions of the invention can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the animal to be treated. One of skill in the art can determine the appropriate dosage based on the above factors. The compounds of the invention may be administered initially in a suitable dosage that may be adjusted as required, depending on the clinical response.

EXEMPLIFICATION

Methods of Synthesis

Compounds of the present invention may be readily synthesized using techniques known to those skilled in the art, such described, for example, in Advanced Organic Chemistry. March, 4th Ed., John Wiley and Sons, New York, N.Y., 1992; Advanced Organic Chemistry, Carey and Sundberg, Vol. A and B, 3rd Ed., Plenum Press, Inc., New York, N.Y., 1990; Protective groups in Organic Synthesis, Green and Wuts, 2"d Ed., John Wiley and Sons, New York, N.Y., 1991; Comprehensive Organic Transformations, Larock, VCH Publishers, Inc., New York, N.Y., 1988 and references cited therein. The starting materials for the compounds described in this invention may be prepared using standard synthetic transformations of chemical precursors that are readily available from commercial sources, such as, Aldrich Chemical Co. (Milwaukee, Wis.); Sigma Chemical Co. (St. Louis, Mo.); Lancaster Synthesis (Windham, N.H.); Ryan Scientific (Columbia, S.C.); Maybridge (Cornwall, UK); Matrix Scientific (Columbia, S.C.); Arcos, (Pittsburgh, Pa.) and Trans World Chemicals (Rockville, Md.).

Results

Reagents and Antibodies.

The anti-CD11b monoclonal antibody (mAb) 44a (IgG2a) [41] and the heterodimer-specific anti-CD18 mAb IB4 (IgG2a) [42, 43] were from ATCC. The mAb 24 (IgG1) [44] was from Abcam and the isotype control antibodies MOPC-21 (IgG1) and MOPC-173 (IgG2a), FITC-conjugated mAbs A85-1 (rat anti-mouse IgG1), R19-15 (rat anti-mouse IgG2a) and FITC-conjugated goat anti-mouse immunoglobulin were from BD Pharmingen (San Diego, Calif.). Rat anti-mouse GR1-FITC and Mac-1-PE were from BD Pharmingen (San Diego, Calif.). Human Fibrinogen (Plasminogen, vonWillebrand Factor and Fibronectin depleted) was from EnzymeResearch Laboratories (SouthBend, Ind.), bovine serum albumin (BSA) was from Sigma (St. Louis, Mich.), recombinant human ICAM1-Fc was from R&D Systems (Minneapolis, Minn.) and iC3b was from Calbiochem (San Diego, Calif.). 384-well plates were from commercial sources (MaxiSorp from Nalgene (Rochester, N.Y.) and Highbind from Corning (Corning, N.Y.)). Non-fat milk was obtained from BioRad (Hercules, Calif.). Cell quantitation reagent MTS was from Promega (Madison, Wis.) and ATPLite was from PerkinElmer (Boston, Mass.). PCR reagents, and restriction and modification enzymes were obtained from New England Biolabs Inc. (Beverly, Mass.). Glutathione-beads were purchased from Sigma (St. Louis, Mich.). All cell culture reagents were from Invitrogen Corp. (San Diego, Calif.) and Mediatech (Manassas, Va.). Fetal bovine serum was purchased from Atlanta Biologicals, Inc (Lawrenceville, Ga.). G418 antibiotic was purchased from Invivogen (San Diego, Calif.).

Mice.

The C57BL/6J (B6) wild type and the B6 CD11b$^{-/-}$ (Jax 3991) [45] mice were purchased from The Jackson Laboratory (Bar Harbour, Me.). The wild type Fischer 344 rats were purchased from Harlan Laboratories (Indianapolis, Ind.). Animal care and procedures were approved by the University of Miami Institutional Animal Care and Use Committee (IACUC) and were performed in accordance with the institutional guidelines.

Cell Lines.

K562 cells (ATCC) stably transfected with wild-type integrin CD11b/CD18 (K562 CD11b/CD18) have been described previously [33, 46]. Mutant CD11bE320A has been described previously [47]. K562 cells stably transfected with mutant integrin CD11bE320A/CD18 (K562 E320A) were generated according to literature protocols [33, 46]. All cell lines were maintained in Iscove's Modified Dulbecco's Medium (IMDM) supplemented with 10% heat-inactivated fetal bovine serum, 50 IU/ml penicillin and streptomycin and 0.5 mg/ml G418.

K562 Cell Adhesion Assay.

Cell adhesion assays with immobilized ligands were performed as previously described [33]. Assays with all different K562 cell lines (K562, K562 CD11b/CD18 and K562 E320A) were performed in an identical fashion. Briefly, 384-well Highbind microtiter plates were coated with a 30 µL solution of ligand in Phosphate Buffered Saline, pH 7.4 containing 1 mM each of $Ca^{2+}$ and $Mg^{2+}$ ions ($PBS^{++}$) overnight at 4° C. Ligand Fg was coated at a concentration of 5-15 mg/mL and iC3b at 1-5 mg/mL. Heterodimer specific mAb IB4 (ascites) was coated at a 1:100 dilution. Subsequently, the non-specific sites in the wells were blocked by incubation with 1% non-fat milk in Tris Buffered Saline (TBS), pH 7.4, at room temperature for 1 h, except for the neutrophil assay, where the wells were blocked with TBS containing 1% gelatin. Next, the wells were washed three times with TBS. K562 cells were suspended in the assay buffer (TBS containing 1 mM each of $Ca^{2+}$ and $Mg^{2+}$ ions ($TBS^{++}$)) and were transferred to the ligand-coated wells (30,000 cells/well). Stock solution of the leukadherin family of small molecule agonists was prepared by dissolving the compounds in DMSO at a concentration of 2-10 mM. Final concentration of DMSO in the assay was approximately 1%. K562 cells were incubated in the presence of increasing concentration of leukadherins for 30 min at 37° C. To dislodge non-adherent cells, the assay plates were gently inverted and kept in the inverted position for 30 min at room temperature. Cells remaining adherent were fixed using formaldehyde and were quantitated using imaging microscopy, as previously described [33]. For the blocking assays, cells were incubated with mAbs 44a and IB4 for 30 min at RT prior to adding them to the assay wells. Assays were performed in 3-6 replicate wells. Data reported is from one of at least three independent experiments. The high throughput screening (HTS) assay to identify novel agonists using a library of >100,000 small molecules was performed as previously described [33, 48].

Neutrophil Adhesion Assay.

Neutrophils from 8- to 10-week old WT and CD11b$^{-/-}$ B6 mice were isolated from thioglycollate-stimulated peritonea according to literature protocols [49]. Cells were suspended in serum free medium (IMDM) and incubated with leukadherins in the ligand-coated wells for 10 min at 37° C. Next, the assay plates were gently inverted and kept in the inverted position for 30 min at room temperature to dislodge the non-adherent cells. Cells remaining adherent were quantitated using imaging microscopy, as previously described [33, 50]. Assays were performed in triplicate wells. Data reported is from one of at least three independent experiments.

Chemotaxis Assay and Time-Lapse Video Microscopy.

Neutrophil chemotaxis on 2D surfaces was performed using Zigmond chamber (Neuro Probe) as described [51, 52] on acid cleaned glass or Fg coated glass coverslips. Cell migration was allowed in a gradient of 10 mM bacterial peptide formyl-methionyl-leucyl-phenylalanine (fMLP, Sigma), in the absence or presence of leukadherins (15 mM). Cell migration was recorded at every 30 sec interval for a period of 25 min using a Nikon Eclipse 90i inverted microscope. Images were acquired with a Nikon DS camera using a PLAN APO 20X differential interference contrast (DIC) microscopy objective and captured into Nikon Imaging software. Analysis of neutrophil migration was performed with the motile population that had moved more than 10 μm [51] using ImageJ software (NIH, USA) with manual cell tracking using the Ibidi chemotaxis and migration tool plugin for ImageJ. Migration velocity and the total displacement (distance from origin) were also analyzed. Quantitation was performed using at least 50 independent cells per condition from at least three independent experiments.

Immunofluorescence.

To examine localization of integrin CD11b/CD18 and F-actin in migrating neutrophils, cells ($10^4$) were stimulated with 10 μM fMLP in serum free medium (RPMI 1640) on glass cover slips for 15 min at 37° C., in the absence or presence of leukadherins (15 mM). The cells were fixed, permeabilized with 0.1% Triton X-100, and stained with anti-mouse CD11b antibody (clone M/170, BD Biosciences) followed by goat anti-rat Alexa488 (Invitrogen) and rhodamine-labeled phalloidin (Invitrogen). A z-series of fluorescence images were recorded with a Leica TCS SP5 confocal microscope and an HCX PL APO 63x/1.4 NA objective and using Leica LAS-AF software. The z-series were analyzed with the Leica LAS-AF software suite. The images presented are from a z-stack projection of 15 confocal sections from the basal to the apical cell side (stack z-spacing, 0.29 μm). Images presented are representative of at least 20 cells analyzed per condition from at least two independent experiments.

To examine clustering of CD11b/CD18 on cell surface, K562 CD11b/CD18 cells ($10^4$) were suspended in serum free medium (IMDM) and incubated without or with the ligand Fg (100 mg) for 3 h at 37° C. as described [53], in the absence or presence of leukadherins (15 mM). The cells were fixed in suspension and stained with anti-CD11b/CD18 mAb IB4 followed by goat anti-mouse Alexa488 (SIGMA). Fluorescence images were recorded with a Leica DMI16000 deconvolution microscope and HCX PL APO 63x/1.3 NA objective and using Leica LAS-AF software, with DCF360FX camera driven by LAS-AF software. The CD11b/CD18 clusters were analyzed in ImageJ and a 3-dimensional representation of fluorescence intensity was also generated in ImageJ. The images presented are representative of at least 20 cells analyzed per condition from at least 3 independent experiments.

Purification of recombinant CD11b A-Domain (.Alpha.A-Domain). Recombinant human aA-domains were constructed and purified according to published protocols [54]. Briefly, the aA-domain in its inactive conformation was generated by cloning and expressing protein fragments spanning residues Gly.sup.111-Gly.sup.321 (321WT) using forward primer 5'-ggttccgcgtggatccgagaacctgtactttcaaggaggat ccaacctacggcag-3' (SEQ ID NO: 1) and reverse primer 5'-gaattc ccggggatccaccctcgatcgcaaagat-3' (SEQ ID NO: 2) and using the Infusion Cloning Kit (Clontech, Mountain View, Calif.) into the BamHI site in vector pGEX-2T according to manufacturer's protocol. The aA-domain in its active conformation was generated by replacing Ile.sup.316 with Gly (1316G [55]) using forward primer 5'-ggttccgcgtggatccgagaacctg-tactttcaaggaggttttcaggaatgt-3' (SEQ ID NO: 3) and reverse primer 5'-atatccccgggattaaccctcgatcgcaaagcccttctc-3' (SEQ ID NO: 4). The insert was digested with BamHI and SmaI and ligated into pGEX-2T vector also digested with BamHI and SmaI. All constructs were confirmed by direct DNA sequencing. All recombinant proteins were expressed as glutathione S-transferase (GST) fusion proteins in *Escherichia coli* and purified by affinity chromatography (Glutathione-beads, Sigma) following manufacturer's instructions. Purified protein preparations were dialyzed against 20 mm Tris-HCl, pH 7.5, 150 mm NaCl (Tris-buffered saline) and subsequently concentrated using Amicon-10 columns (Millipore) and stored at −80.degree. C. Purity was confirmed by 1D SDS-polyacrylamide gel electrophoresis analysis.

αA-Domain Ligand-Binding Assay.

Maxisorp 96-well plates were coated with Fg (1 μg/well) in 10 mM PBS, pH 7.4 overnight and blocked with 1% bovine serum albumin in PBS. Binding of purified, GST-tagged aA-domain (50 mL/well of 5 mg/mL solution) to immobilized Fg was performed in the TBS assay buffer (TBS containing 0.1% BSA, 1 mM $Mg^{2+}$, 1 mM $Ca^{2+}$, and 0.05% Tween 20) for 1 h at room temperature. Unbound aA-domain was removed by washing the assay wells twice with $TBS^{++}$. Subsequently, the amount of bound protein was determined by incubating with anti-GST antibody conjugated to horseradish peroxidase (GE, Piscataway, N.J.) (1:2000 dilution) for 1 hr. Unbound anti-GST-HRP was removed by washing the assay wells twice with $TBS^{++}$. Detection of bound protein was done using TMB substrate kit (Vector Labs, Burlingame, Calif.) according to manufacturer's protocol. Absorbance was read using Spectromax M5 spectrophotometer (Molecular Devices, Sunnyvale, Calif.). Assays were performed in triplicate wells and the data shown is from one of at least three independent experiments.

Flow Cytometry.

Flow cytometric analysis of K562 cells for integrin CD11b/CD18 cell surface expression was performed using published protocols [56, 57]. Briefly, cells were suspended in the assay buffer (TBS containing 1 mM each of $Ca^{2+}$ and $Mg^{2+}$ ions ($TBS^{++}$) and 0.1% BSA). Cells ($5 \times 10^5$) were incubated with primary mAb (1:100 dilution of IB4 or 44a ascites) in the absence or presence of 15 mM leukadherin in 100 ml $TBS^{++}$ at 37° C. for 30 minutes. Subsequently, the cells were washed three times with the assay buffer and incubated with goat anti-mouse-APC (1 mg/ml, Invitrogen) for 20 min at 4° C. Cells were washed twice with the assay buffer and analyzed using FACSCaliber flow cytometer (BD Biosciences, CA), counting at least 10,000 events. Data was analyzed using the CellQuest software (BD Biosciences). Assays were performed in triplicate and the data shown is from one of at least three independent experiments.

Cell Viability Assay.

Cell viability assay was performed as described. Briefly, K562 CD11b/CD18 cells (10,000/well) were incubated in 96 well plates (Corning, Corning, N.Y.) with increasing amounts of indicated compound for 24 h. The number of viable cells after 24 h was determined by using MTS reagent according to manufacturers protocol (Promega, Madison, Wis.) and using Spectramax M5 spectrophotometer (Molecular Devices) for reading of the assay plates. Data presented is representative of at least two independent experiments.

Western Blot.

K562 CD11b/CD18 cells were incubated with LA1, LA2, LA3 (15 mM) or FG (200 mg) in serum free media containing for 1 hour at 37° C. Cell lysates were run on a 10% SDS-PAGE gel and transferred to PVDF membrane (ThermoScientific, Waltham, Mass.) using established protocols. Membranes were probed with 1:1000 dilution of anti-phospho ERK1/2 antibody (Thr202/Tyr204, Cell Signaling, Danvers, Mass.), stripped with Reblot mild stripping solution (Millipore, Billerica, Mass.), and reprobed first with anti-ERK1/2 antibody (Cell Signal) and next with anti-GAPDH antibody (Cell Signaling) and developed according to manufacturer's protocols (ThermoScientific, Waltham, Mass.). Data presented is representative of at least three independent experiments.

Blood Cell Count.

Complete peripheral blood leukocyte counts from the different mice were quantified at the mouse pathology core using standard assays.

In Vivo Peritonitis Model.

Thioglycollate-induced peritonitis was performed as previously described [49], using 8-10 week old WT B6 and CD11b$^{-/-}$ B6 mice. Leukadherin agonists were administered thirty min prior to intra peritoneal (i.p.) thioglycollate (3%) injection. LA1 and LA2 (200 mL of 20 mM solution in saline) were administered intra venously (i.v.). LA3 was administered i.p. (1 mL of 20 mM solution in saline). To evaluate peritoneal neutrophil recruitment, mice were euthanized at 4 h following thioglycollate injection, the peritoneal lavage was collected and the number of emigrated neutrophils was quantified using double positive cells for GR-1 and Mac-1 staining as described [36].

Balloon Induced Arterial Injury in Rats.

All surgeries were under isoflurane anaesthesia (Baxter, Ill., USA). Balloon injury in the right iliac artery was inflicted with a 2F Fogarty catheter (Baxter Corp., Irvine, Calif., USA) adapted to a custom angiographic kit (Boston Scientific, Scimed) [58]. An aortotomy in the abdominal aorta was made to insert a 2F Fogarty embolectomy catheter to the level of the right iliac artery. The balloon was inflated to 1.5-1.6 atmospheres and retracted to the arteriotomy site three times. The aortic excision was repaired with 8.0 sutures. The abdominal cavity was closed by planes using interrupted suture pattern. Arterial specimens were collected 3-30 days after injury and fixed in 4% formalin-PBS (Sigma-Aldrich, St. Louis, Mo.) for 5 min and analyzed by histology and immunostaining.

Histology and Immunostaining.

Elastica van Gieson staining was used for histochemical analyses to evaluate neointima formation. Morphometric analyses was performed in a blinded fashion using NIH ImageJ. Immunostaining with anti-rat CD68 (1:50, AbD Serotec) for the detection of macrophages in the tissue.

Zebrafish Tailfin Injury Assays.

Transgenic Tg(mpx::eGFP) [59] were maintained according to standard protocols [60]. Tailfin injury in three days post fertilization (dpf) larvae was performed as described [59]. Larvae were anesthetized by immersion in E3 with 4.2% tricane, and tail was completely transected with a sterile microdissection scalpel in accordance with the approved protocols and were recovered for the indicated time points. Zebrafish larvae (3 dpf) were treated with compounds as described (Ref). Briefly, small molecule compounds were administered by immersing the larvae in a solution of the compounds in E3. The final concentration of DMSO was kept at <1%. For the assessment of the inflammatory response, injured larvae were analyzed at 4 h post-injury. For the post-wash assay, uninjured larvae incubated with the compounds in E3 for 4-8 h, washed into E3 and injured. Larvae were analyzed using a Leica DMI6000B microscope and an Hamamatsu Orca-3CCD camera using Volocity. Excitation was performed using the laser at 488 nm and the images were analyzed using Volocity. The number of fluorescent neutrophils at the site of inflammation were counted by eye in a blinded fashion.

Statistical Analysis.

Data were compared using one-way ANOVA with posthoc analysis, when comparing two or more groups. p values <0.05 were considered significant.

Computational Modeling.

To model binding of leukadherins to the active, open conformation of the αA-domain, we performed a series of computational studies as follows. First, we generated a model of the αA-domain in the open (active) conformation. The high-resolution three-dimensional structure of αA in both its closed (inactive) and open (active, ligand-competent) conformations is available from PDB [61, 62]. However, the α7 helix in αA (that creates part of a hydrophobic pocket known as Socket for Isoleucine (SILEN) in CD11b [62] or IDAS in CD11a [63] and that shows the highest conformational change upon αA-activation [64-66]) is shorter by three residues in the three-dimensional structure of the open form [62] as compared to that of the closed form of αA [61]. Because an αA agonist is predicted to bind in this region[11], we manually extended the α7 helix in the high resolution structure of αA-domain [62] by three additional residues from the domain of the closed (inactive) form of αA [61]. The model was refined by hydrogen bond optimization and constrained minimization.

To identify possible ligand binding modes, we applied an induced fit docking (IFD) procedure implemented in the Schrodinger software suite as previously described [39]. The αA poses were ranked using MM GB/SA; this approach was used to estimate the free energy of binding for compounds to αA using the Generalized Born solvation model augmented with the hydrophobic solvent accessible surface area term (GBSA). The optimized αA structure was then used for compound re-docking using a standard potential [67]. Several IFD runs were performed and they resulted in high-scoring poses for the most agonists [39]. The optimized receptor structures after IFD were then used to dock the novel agonists using Schrodinger Glide and the SP scoring function. Next, the best scoring poses for compounds in their Z configuration were further optimized in molecular dynamics simulations. Molecular dynamics simulations are performed as multi-step protocols with several minimization and simulation steps preceding the production molecular dynamics run. Simulations were performed with the molecular dynamics package Desmond by DEShaw Research [68] at 300K and 325K (NPT ensemble) using the SPC water model (cubic box of 10 Å around the receptor) on IBM E-server 1350 cluster (36 nodes of 8 Xeon 2.3 GHZ cores and 12 GB of memory). The final simulations times were 12 ns in which the reported poses remained stable. FIG. 8 shows poses of LA1, LA2 and LA3.

Results

We believe that integrin agonists have several advantages over antagonists. Research with antagonists over last several years has shown them to be suboptimal. First, it has been suggested that suppressing leukocyte recruitment with antagonists requires occupancy of >90% of active integrin receptors [31], usually requiring high levels of blocking antibodies in vivo. Second, complete blockade of cell surface-expressed CD11b/CD18 even with antibodies is difficult due to availability of a large mobilizable intracellular pool of CD11b/CD18 [29, 30]. Third, several other antagonists, such as ligand-mimetic neutrophil inhibitory factor (NIF) [69] and recombinant αA-domain [70], were effective in animal models but their large size and immunogenicity preclude their use as a therapeutic agent. Recombinant NIF (UK-279276) failed in clinical trials. Likewise, peptides derived from either anti-CD11b/CD18 antibodies or CD11b/CD18 ligands are not very efficacious in blocking ligand binding in vitro [71], perhaps owing to their improper conformation in solution or to their small size relative to the ligand binding region on CD11b/CD18. Finally, many antagonistic antibodies (such as rhuMAb CD18, anti-CD18 LeukArrest (Hu23F2G) and anti-ICAM1 mAb Enlimomab (R6.5)) failed in treating inflammatory/autoimmune diseases in several clinical trials [26, 28] and β2 integrin blockers have also shown unexpected side effects and have had to be withdrawn from the market [32].

Discovery of Novel CD11b/CD18 Agonists—Leukadherins.

We used an in-house developed cell-based high throughput screening (HTS) assay [33] to screen a chemical library of >100,000 molecules for compounds against K562 CD11b/CD18 cells. As a unique strategy, we focused on compounds that increase cell adhesion (agonists), rather than those that inhibit it. We identified a series of compounds containing a core furanyl thiazolidinone motif that increased adhesion (agonists) of K562 CD11b/CD18 to its physiologic ligand fibrinogen (Fg) [33, 48]. K562 CD11b/CD18 cells showed virtually no binding to immobilized Fibrinogen (Fg) when incubated in the assay buffer (1 mM each of physiologic ions $Ca^{2+}$ and $Mg^{2+}$ in Tris buffered saline ($TBS^{++}$)) alone. Surprisingly, we found that a large subset of the hits contained a central five-membered 2,4-di-oxo-thiazolidine[33] and 2,4-di-oxo-thiazolidine motif containing compounds as hits [48]. We confirmed targeting of the αA-domain by the 2,4-di-oxo-thiazolidine motif containing compounds using binding assays with purified recombinant αA-domain, where these compounds increased binding of αA-domain to immobilized Fg [72]. Additionally, binding was selective as cells not expressing CD11b/CD18 did not show any appreciable binding and the binding of CD11b/CD18 expressing cells could be blocked with known blocking monoclonal antibodies (mAbs) 44a [41] (anti-CD11b) and IB4 [42, 43] (anti-CD18).

We explored the structure-activity relationship (SAR) of various substitutions on the central core [39] and identified several compounds, that we have termed leukadherins. This includes leukadherin-1 (LA1), leukadherin-2 (LA2) and leukadherin-3 (LA3) that increased CD11b/CD18 dependent cell adhesion to Fg with $EC_{50}$ (effective concentration for 50% increase in adhesion) values of 4 μM, 12 μM and 14 μM respectively. Several other compounds provided similar level of activity. We also identified a structurally related compound, leukadherin-control (LA-C), which showed no affect on CD11b/CD18 dependent cell adhesion. This allows us, for the first time, to test whether CD11b/CD18 activation is anti-inflammatory and whether small molecule agonists of integrins can activate integrins in vivo and lead to outcomes as anticipated by the animals knocked-in for activating mutants of other integrins.

We also performed in silico examination of a number of analogs. In silico docking studies using high-resolution three-dimensional structures of the αA-domain in its low-affinity and its high-affinity conformations [61, 62, 64] suggested that the LA1-3 preferentially bind to the open, high-affinity conformation of αA-domain, near the activation-sensitive α7-helix region, allosterically stabilizing the αA-domain in its high affinity conformation [39] (FIG. 8).

For certain compounds of Formula (II), we found that substitutions at the C-5 position of the furan ring ($R^3$ substituents) had the largest effect on agonist potency (such as, compounds 1-30) [39]. Non-aromatic or non-conjugated substituents that disrupted the pi-conjugation with the planar furanyl ring were strongly dis-favored. In certain orientations, planar aromatic rings were preferred and non-substituted phenyl ring was also preferred over aliphatic groups at ortho or the para positions of the phenyl ring. For the substituents at the N-3 position of the thaizolidine ring, shortening the length of the substituted ester (from ethyl to methyl), and shortening the aliphatic chain length was highly dis-favored. Similarly, substitution of the aliphatic chain with a phenyl ring was dis-favored. Long-chain, bulky residues were also dis-favored at the N-3 position. However, a compound containing methylene substituted small aromatic ring bound to a level similar to LA3. Conversely, a co-substitution of benzyl at the N-3 position with a highly electron-withdrawing and bulky para-substituted aromatic at $R^3$ was highly dis-favored. Certain compound also showed selective binding to the purified recombinant αA-domain by increasing its binding to immobilized Fg [72] as well as a high selectivity for integrin CD11b/CD18 over CD11a/CD18.

To further evaluate the compounds we also calculated various physicochemical descriptors using Schrodinger QikProp program. Our most favored compounds in that series (compounds 1-14) have good predicted Caco-2 cell permeability and human oral absorption. Among them LA1-3 have a slightly better clogP and better predicted solubility and among the highest ligand efficiency (BEI=14) [73].

Next, in order to gain insights into potential binding pockets for this subset of small molecules in the αA-domain, we conducted in-silico docking experiments. The high-resolution three-dimensional structure of CD11b A-domain in both its closed (inactive) and open (active, ligand-competent) conformations is available from PDB [61, 62, 64]. However, the α7 helix in αA (that creates part of a hydrophobic pocket known as Socket for Isoleucine (SILEN) in CD11b[62] or IDAS in CD11a [63] and that shows the highest conformational change upon αA-activation [64-66]) is shorter by three residues in the three-dimensional structures of the open form [61, 62] as compared to that of the closed form of αA [61, 64]. As the newly discovered agonists are predicted to bind in this region and stabilize this conformation of αA,[11] we constructed a model of the open (active, ligand-competent) conformation of the CD11b A-domain by manually extending the α7 helix in the high resolution structure of CD11b A-domain [61, 62] by three additional residues from the structure of the closed form followed by hydrogen bond optimization and constrained (Impref) minimization as implemented in the Maestro protein preparation facility (Schrodinger Inc, Portland).

Conformational repositioning of the α7 helix upon activation, which appears to be stabilized upon agonist binding suggests that the agonists bind in the region between helix α7 and a1 and the central β sheet [64]. Therefore we utilized the above optimized structure of the αA-domain in the open conformation to initiate compound docking. In the apo structure this activation sensitive α7 helix region is spatially crowded by many hydrophobic residues lining the pocket. We applied an induced fit docking procedure implemented in the Schrodinger software suite in which initial docking with a softened potential to generate an ensemble of possible poses is followed by receptor optimization and ligand re-docking [67]. This protocol resulted in a high scoring pose of LA1-3

(Z configuration) in which the carbonyl oxygens of the 2,4-di-oxo-thiazolidine core and its analogs are fixed by Ser133 and Thr169 and, for example, the hydrophobic 2,4-dichlorophenyl moiety of LA3 is interacting in the hydrophobic pocket. In a stable 6 ns all-atom explicit solvent molecular dynamics simulation at increased temperature (using Desmond by DEShaw Research)[68] the α7 helix adjusts only very slightly. The induced-fit docking receptor was used to dock additional structures using Schrodinger Glide Program. [74] The obtained poses were then rescored using MM-GB/SA methodology[75] allowing receptor flexibility to obtain more accurate estimates of relative binding free energies. The resulting binding hypothesis of the best compounds are shown in FIGS. 8 and 12. As we expected, the hydrophobic phenyl furanyl moiety (the C5-substituent on the thiazolidine ring) is buried in a hydrophobic pocket lined by residues L312, I308, L305 (α7 helix), L164, V160, F156 (α1 helix), and Y267, I269, I236, V238, I236, I135 (central beta sheet). This structural model also explains why compound LA-C (structurally related to LA1-3) is inactive, as in this binding mode the αC carbon of the ethylcarboxylate moiety at N-3 position of the central thiazolidine ring of LA-C is in close proximity to Ser133, Thr169, and Asp132 (less than 2.5 Å), which creates a tight fit and does not tolerate the larger methyl group at αC that is present in some compounds but is absent in LA1-3. In general, we found that, for the most comparable compounds, the lower activity of the sterically more demanding compound can (at least partially) be attributed to increased receptor and/or ligand strain.

The SAR and the binding hypothesis suggest that one hydrophobic interaction is critical. Compounds with two polar ends are generally found to be inactive. The interaction in the hydrophobic pocket appears quite sensitive to sterical demand and the overall size of the molecule. For example, in case of the smaller ethyl acetate N-3 substituent, larger as well as smaller phenyl furanyl substituents are tolerated (although the smallest is the most active) while for structures with larger N-3 substituents only the unsubstituted phenyl furanyl is active. Thus, the in silico docking studies suggest a reasonable hypothesis for the binding of these novel allosteric agonists of integrin CD11b/CD18. Additionally, during the various induced fit docking studies we obtained other poses. For example, one model showed the compounds "flipped" along its long, vertical axis. However in all cases the hydrophobic moiety interacts in the same region described and illustrated in FIG. 8.

Next, we determined the selectivity of compounds for integrin CD11b/CD18 over highly homologous integrin CD11a/CD18 (also known as LFA-1). We also generated K562 cells stably transfected with wild type integrin CD11a/CD18 (K562 CD11a/CD18). Next, we measured the ability of LA3 to increase cell adhesion to immobilized ICAM-1, a physiologic ligand of integrin CD11a/CD18. It showed two-fold higher selectivity for integrin CD11b/CD18 over CD11a/CD18, with $EC_{50}$ values of 13.6±5 μM with K562 CD11b/CD18 cells. This is in contrast with the previously described compounds,[76] which showed equal binding to both integrins in our assays.

To identify binding site of LA1-3, which are predicted to bind the ligand-binding αA (or α1) domain in CD11b/CD18 [33, 39, 76], we generated K562 cells stably expressing mutant integrin CD11bE320A/CD18 (K562 E320A). The highly conserved residue E320 in the linker following the activation-sensitive α7-helix in the CD11b A-domain (αA-domain) acts as an endogenous ligand of the CD18 vWFA-domain (βA- or I-domain) [47]. The E320A mutation abolishes agonist $Mn^{2+}$-ion mediated increase in ligand-binding by CD11b/CD18. However, stabilization of αA in a high-affinity conformation by additional activating mutations overcomes this deficit and induces ligand binding in the E320A mutant [65]. LA1, LA2 and LA3 (but not $Mn^{2+}$) selectively increased binding of K562 E320A to Fg (FIG. 1H), suggesting that these compounds also bind to and stabilize the αA-domain in a high-affinity conformation. To confirm, we used purified recombinant αA [72] and found, as expected [33, 76], that LA1 and LA2 increased binding of the WT αA to the immobilized ligand (FIG. 1I) to a level of binding observed with a mutant αA-domain containing a constitutionally activating mutation (I316G) [55]. This suggests that leukadherin binding stabilizes αA in its open, high-affinity conformation. Flow cytometry analysis showed an increase in the binding of activation sensitive mAb24 to K562 CD11b/CD18 cells in the presence of LA1, confirming that LA1 activates full-length integrin expressed on live cells. Björklund et al. described a CD11b/CD18 agonist (IMB-10) that also targets the CD11b/CD18 αA [76]. We compared the relative affinities of LA1 and IMB-10 for CD11b/CD18 using our cell-based adhesion assay and found that LA1 showed higher affinity, perhaps owing to its more rotationally constrained furanyl-thiazolidinone central scaffold.

Leukadherins LA1-3 increased adhesion of monocytic cell line THP-1 to immobilized Fg (not shown). We also examined the effect of LA1-3 on binding of K562 CD11b/CD18 to iC3b (covalently bound to the surface of erythrocytes using fresh serum, EiC3b, as in the physiologic state) using rosette formation assay [46] and found that they significantly increased EiC3b binding by CD11b/CD18 expressing cells (not shown).

Leukocyte chemotaxis on 2D surfaces involves integrin-mediated sequential adhesion and de-adhesion steps [77]. Cells expressing constitutively active integrin mutants show increased adhesion and dramatically reduced cell migration in chemotactic gradients, by freezing integrins in a ligand-bound state [78, 79]. To test if increased cell-adhesion by leukaderins affects cell migration, we used murine neutrophils chemotaxing in response to a gradient of chemokine peptide formyl-Met-Leu-Phe (fMLP) [52]. Live cell imaging showed smooth migration of neutrophils in physiologic buffer (FIG. 2A). However, treatment with LA1, LA2 or LA3 lead to a significant decrease in the lateral migration and the migration velocity of these cells (FIG. 2A-C). Although the LA1-3 treated cells showed some movement towards the chemokine, they displayed reduced directional persistence and reduced mean squared displacement (MSD), suggesting constrained motility, as compared to a more directed motility for control (DMSO) cells. Unlike the neutrophils chemotaxing in the absence of leukadherins, where they displayed a typical flattened leading edge and short narrow tail, cells migrating in the presence of LA1-3 showed elongated uropods, suggesting defects in cell de-adhesion as the key mechanism behind decreased cell migration, as has been seen with activating integrin mutations [36, 38]. To investigate, we used confocal microscopy that showed clustered CD11b/CD18 in the extended uropods of LA1-3 treated cells (FIG. 2D), suggesting that the failure to release integrin-substrate interactions in the uropod was responsible for the defective migration. Leukadherin treatment showed no change in neutrophil migration in 3D collagen gels, supporting recent findings that leukocyte migration in 3D is integrin independent. Yet, leukadherins reduced the efficiency of trans-endothelial migration (TEM) by THP-1 cells across a TNFα-activated HUVEC layer in vitro by increasing cell adhesion to the HUVEC layer. In all, these data suggest that leukadherins increase cell adhesivity and reduce their lateral motility, thereby affecting TEM.

Integrin activation and ligand binding leads to clustering of integrins on the cell surface and initiates outside-in signaling, including the activation of p38 mitogen activated protein kinase/extracellular signal-regulated kinase (MAPK/ERK1/2) pathways [16, 21], thereby mimicking the anchorage-dependent pro-survival signals in most cells [53]. As LA1-3 bind to and activate CD11b/CD18, it is conceivable that such binding alone may trigger integrin-mediated outside-in signaling, thus mimicking a ligand bound integrin state for the cell, which may have profound consequences on leukocyte lifetime and function. To test, we used confocal microscopy for imaging CD11b/CD18 clustering on cell surface [16]. Cells displayed no detectable CD11b/CD18 macro clustering in the absence of ligand (FIG. 2E, DMSO), but showed high-degree of clustering upon addition of exogenous Fg (FIG. 2F, DMSO). Similarly, treatment with LA1-3 exhibited integrin macro-clustering only upon addition of external Fg (FIGS. 2E-F), suggesting that LA1-3 are not integrin ligand mimics. Additionally, since known CD11b/CD18 agonists $Mn^{2+}$ [80] and activating mAbs [81] and its ligands [16] induce ERK1/2 phosphorylation, we examined ERK1/2 phosphorylation in cells and found that LA1-3 treatment did not induce it (pERK, FIG. 2G) as opposed to incubation with ligand Fg (FIG. 2G) or phorbol ester PMA (not shown). Thus, we conclude that leukadherins do not mimic ligands and do not induce outside-in signaling in cells.

We also found that leukadherins reduced the pro-inflammatory behaviour of leukocytes by locking CD11b/CD18 in an active conformation. Surprisingly, LA1-3 treatment resulted in robust Akt phosphorylation, like with ligand Fg, as compared to treatment with DMSO alone (not shown). We surmised that leukadherins may also suppress pro-inflammatory cytokine express-ion in leukocytes. Indeed, we found that leukadherins decrease secretion of soluble factors by neutrophils and macrophages. In an experiment to test the effect of leukadherin treatment on secretion of pro-inflammatory cytokines by leukocytes, we stimulated WT mouse macrophages and neutrophils with LPS, TNFalpha or ILbeta in the absence or presence of two different concentrations of agonist LA1 and measured levels of pro-inflammatory cytokine in the cell supernatant. We found that cell stimulation significantly increased secretion of inflammatory factors (such as IL-6, TNFa, IL-1b, IFNg, MMP-9 soluble uPAR) in both cell types, as compared to unstimulated cells, and that addition of LA1 significantly decreased it in the supernatant, suggesting that leukadherins have additional anti-inflammatory effects. Leukadherins decrease secretion of pro-inflammatory factors, including microparticles, by beta2-integrin expressing cells. Additionally, they increase secretion of anti-inflammatory factors, such as IL-10.

To determine the effects of LA1-3 on inflammatory responses in vivo, we monitored their effects on neutrophil recruitment upon acute thioglycollate-induced peritonitis in mice [45]. LA1-3 showed no in vitro cytotoxicity to K562 cells (FIG. 9) or to murine neutrophils at concentrations as high as 50 μM. Intraperitoneal injection of thioglycollate resulted in significant peritoneal accumulation of neutrophils, as compared with saline alone (p<0.001) (FIG. 3A). Administration of LA1 30 min prior to thioglycollate injection significantly reduced neutrophil accumulation (by 40%, p<0.05), LA2 reduced it by 65% (p<0.0001) and LA3 reduced it by 55% (p<0.05) as compared to administration of the vehicle alone. Determination of the leukocytes in circulation from mice treated with leukadherins showed no reduction in their cell number as compared to the vehicle treated animals (Table S1). This suggests that leukadherins do not cause leukocyte cytotoxicity in vivo, thus ruling it out as a reason for the observed reduction in marginated neutrophils in leukadherin treated animals. We also found that LA1-3 administration did not significantly reduce the number of recruited neutrophils in the peritoneum of $CD11\beta^{-/-}$ mice (FIG. 3B), which showed increased neutrophil accumulation compared to WT, as published before [45]. This further suggests that LA1-3 selectively target integrin CD11b/CD18 in vivo.

We found that in TGC-induced peritonitis, the number of peritoneal neutrophil increased after 4 h in vehicle-treated animals, peaked after 12 h and declined thereafter. In LA1 treated animals, neutrophil accumulation was significantly reduced at 4 h and stayed reduced after 12 h. We observed comparable numbers of peritoneal neutrophils after 24 h among both groups of animals, suggesting that leukadherins significantly delayed neutrophil recruitment. Compounds were also dosed i.v. and orally using a solution of 30% 2-hydroxypropyl-β-cyclodextrin (w:v) in PBS, which showed good bioavailability and efficacy.

We used tissue histology from TGC-induced peritonitis animals to determine if leukadherin-treatment led to sequestration of neutrophils in any particular organ. We found no sequestration of neutrophils in leaukadherin-treated animals confirming that leukadherins do not lead to sequestration of neutrophils in any particular organ in mice and that the effects of leukadherins are indeed mediated through its increase in neutrophil adhesivity near sites of inflammation and decreased neutrophil motility.

Leukocyte recruitment precedes neointimal thickening and restenosis following percutaneous transluminal coronary angioplasty (PTCA) [5]. Denudation of the endothelial cell lining at the site of mechanical vascular injury leads to the deposition of fibrin and platelets, where selective binding between the platelet cell surface receptor GP Ibα and the integrin CD11b/CD18 expressed on the surface of leukocytes mediates the recruitment of leukocytes [40]. Indeed, in the experimental models of mechanical vascular injury, antibody-mediated CD11b/CD18 blockade or its absence ($CD11b^{-/-}$) decreases intimal thickening after angioplasty or stent implantation [23]. To investigate the effects of pharmacologically activating CD11b/CD18 in vivo on this injury, we tested our agonists in an arterial balloon injury model in rats [58]. We administered leukadherins LA1, LA3 or vehicle (DMSO) to Fisher male rats 30 min prior to injury and continued injections every other day for three weeks. LA2 showed no effect, perhaps due to differences in the binding pocket between the rat and human αA (only ~70% homology [70]). Injured arteries of the LA1 and LA3 treated animals developed significantly reduced neointimal thickening (neointima to media ratio of 0.16±0.02 and 0.14±0.01 respectively, p<0.05) as compared to vehicle treated animals (ratio of 0.23±0.01) (FIGS. 3C-D). Control compound LA-C showed no effect (FIG. 10). To determine if leukadherin treatment leads to reduced leukocyte accumulation, which precedes vascular remodeling, we performed immunohistochemical analyses of arteries three days post-injury using macrophage specific anti-CD68 antibody. We observed a significant reduction in the number of medial macrophages in the arteries of LA1 and LA3 treated animals (17.7±3.1 and 6.9±1.3, respectively, p<0.0001) over the vehicle controls (42.2±6.7) (FIGS. 3D-E). Together, these results suggest that leukadherin treatment leads to reduced accumulation of leukocytes at the site of vascular injury and subsequent decrease in neointimal thickening.

To determine whether CD11b/CD18 agonists have any therapeutic advantages over antagonists, we performed a head-to-head comparison between a well-characterized CD11b/CD18 antagonist (anti-CD11b antibody M1/70, [82]) and LA1 using an established mouse model of kidney disease, the anti-glomerular basement membrane (anti-GBM) nephritis [7]. This model is characterized by neutrophil infiltration that mediates urinary protein loss, including albumin. In line with an important role for CD11b in this disease, CD11b$^{-/-}$ mice [7] and anti-CD11b mAb treated rats [83] show decreased leukocyte infiltration and a protection from proteinuria. Here, induction of disease in mice led to peak influx of neutrophils and maximal proteinuria at day 3. M1/70 significantly decreased neutrophil influx and reduced proteinuria (not shown). However, LA1 produced significant and maximal decrease in both the number of infiltrated neutrophils and the proteinuria in treated mice, demonstrating a clear therapeutic advantage of agonists over antagonists.

To visualize effects of leukadherin treatment on leukocyte accumulation in live animals, we used transgenic Tg(mpx:: eGFP) zebrafish that express GFP under a myeloid-specific peroxidase gene (mpx) promoter to specifically fluorescently tag neutrophils for live imaging of leukocyte recruitment [59]. Tailfin transection in zebrafish larvae at 3 days postfertilization (dpf) lead to a rapid and robust recruitment of neutrophils to the site of tissue injury (FIG. 4A-C) [59]. Administration of LA1 and LA2 to uninjured larvae showed no observable effects (FIG. 4B) (lower solubility of LA3 precluded its use in this experiment). However, both LA1 and LA2 significantly reduced the neutrophil accumulation in the zebrafish tailfin 4 h post injury (15.6±1.7 and 13.3±2.1, respectively, p<0.0001) as compared to the treatment with vehicle alone (34.6±4.5). Fluorescence imaging of the injured whole zebrafish larvae showed no difference in the total number of neutrophils in the leakadherin treated and untreated animals (FIG. 11), suggesting that the leukadherin-mediated reduction in neutrophil accumulation at the site of injury was not due to an overall diminished neutrophil cell number, further confirming the results from our experiments in mice which showed that leukadherins do not cause cytotoxicity in vivo (Table S1). Finally, to determine if the in vivo effects of leukadherin treatment were reversible, we administered LA1 and LA2 to uninjured zebrafish for 4-8 h, rinsed the zebrafish, induced tailfin injury and quantitated neutrophil accumulation 4 h post-wash. We found that removal of compounds lead to a similar level of neutrophil accumulation at the injured tailfins as in untreated zebrafish larvae. Collectively, these data demonstrate that leukadherins down-regulate neutrophil accumulation at the site of tissue injury and that their in vivo effects can be reversed by the removal of these compounds.

Leukadherins reduce renal I/R injury. To evaluate use of leukadherins in the I/R injury induced changes in the kidney function of WT mice, we performed another experiment. B6 male mice (8-12 weeks of age) were anesthetized and kept on a heating pad to keep them at a constant 37° C. temperature. Next, an abdominal incision was made and the renal pedicles were occluded bilaterally with a nontraumatic vascular clamp for 30 minutes, the clamp then removed and the surgical incision was closed. Sham surgery was performed with an identical procedure but without application of the clamps. Renal I/R injury was assessed at 24 h post-ischemia by measuring the serum creatinine levels. Mouse sera from the tail incision was used for the analyses of sCr (and BUN levels (not shown)) using manual kits (Stanbio Laboratory). Administration of leukadherins LA1 and LA2 30 min prior to I/R injury lead to a significant reduction in sCr levels as compared to vehicle DMSO treated animals (not shown), suggesting that these compounds have a reno-protective effect. Leukadherin treatment also showed reduced wound-healing in a mouse model (not shown). Additionally, leukadherin treatment led to reduced T-cell proliferation in a mixed lymphocyte reaction (MLR), suggesting additional use in treating various inflammatory and autoimmune diseases.

Leukadherins increase neutrophil adhesion and decrease 2D chemotaxis in vitro. To determine if leukadherins have a similar effect on neutrophils in vivo, we used intravital microscopy on mouse cremaster muscle and found that leukadherins increased neutrophil adhesion in the postcapillary venules and decreased their rolling velocity (not shown), suggesting that these agonists behave similarly in vivo. More importantly, we found that blocking anti-CD11b mAb M1/70 reversed the effects of leukadherins, confirming that the effects of leukadherins are via its agonism of CD11b/CD18.

We believe that the leukadherin activated CD11b/CD18 increases leukocyte adhesion, which decreases leukocyte crawling and transendothelial migration and, thus, reduced recruitment into the inflamed/injured tissue [37]. The data presented here suggests that integrin-specific small molecule mediated increase in leukocyte adhesion in the vasculature reduces leukocyte infiltration and inflammation and can be an effective pharmacologically targetable methodology to treat a variety of inflammatory and autoimmune diseases.

All publications, patents and patent applications are herein incorporated by reference in their entirety to the same extent as if each individual publication, patent or patent application was specifically and individually indicated to be incorporated by reference in its entirety.

EQUIVALENTS

Those skilled in the art will recognize, or be able to ascertain using no more than routine experimentation, many equivalents to the specific embodiments of the invention described herein. Such equivalents are intended to be encompassed by the following claims.

REFERENCES

1. Mayadas, T. N. and X. Cullere, *Neutrophil beta2 integrins: moderators of life or death decisions.* Trends Immunol, 2005. 26(7): p. 388-95.
2. Ley, K., et al., *Getting to the site of inflammation: the leukocyte adhesion cascade updated.* Nat Rev Immunol, 2007. 7(9): p. 678-89.
3. Hynes, R. O., *Integrins: bidirectional, allosteric signaling machines.* Cell, 2002. 110(6): p. 673-87.
4. Arnaout, M. A., *Leukocyte adhesion molecules deficiency: its structural basis, pathophysiology and implications for modulating the inflammatory response.* Immunol Rev, 1990. 114: p. 145-80.
5. Simon, D. I., et al., *Decreased neointimal formation in Mac-1 (−/−) mice reveals a role for inflammation in vascular repair after angioplasty.* J Clin Invest, 2000. 105(3): p. 293-300.
6. Cao, C., et al., *A specific role of integrin Mac-1 in accelerated macrophage efflux to the lymphatics.* Blood, 2005. 106(9): p. 3234-41.
7. Tang, T., et al., *A role for Mac-1 (CD11b/CD18) in immune complex-stimulated neutrophil function in vivo: Mac-1 deficiency abrogates sustained Fcgamma receptor-dependent neutrophil adhesion and complement-dependent proteinuria in acute glomerulonephritis.* J Exp Med, 1997. 186(11): p. 1853-63.

8. Plow, E. F., et al., *Ligand binding to integrins.* J Biol Chem, 2000. 275(29): p. 21785-8.
9. Soriano, S. G., et al., *Mice deficient in Mac-1 (CD11b/CD18) are less susceptible to cerebral ischemia/reperfusion injury.* Stroke, 1999. 30(1): p. 134-9.
10. Kubota, Y., et al., *M-CSF inhibition selectively targets pathological angiogenesis and lymphangiogenesis.* J Exp Med, 2009. 206(5): p. 1089-102.
11. Ahn, G. O., et al., *Inhibition of Mac-1 (CD11b/CD18) enhances tumor response to radiation by reducing myeloid cell recruitment.* Proc Natl Acad Sci USA. 107(18): p. 8363-8.
12. Ophascharoensuk, V., et al., *Role of intrinsic renal cells versus infiltrating cells in glomerular crescent formation.* Kidney Int, 1998. 54(2): p. 416-25.
13. Le Hir, M., et al., *Podocyte bridges between the tuft and Bowman's capsule: an early event in experimental crescentic glomerulonephritis.* J Am Soc Nephrol, 2001. 12(10): p. 2060-71.
14. Tang, T., et al., *A role for Mac-1 (CDIIb/CD18) in immune complex-stimulated neutrophil function in vivo: Mac-1 deficiency abrogates sustained Fcgamma receptor-dependent neutrophil adhesion and complement-dependent proteinuria in acute glomerulonephritis.* J Exp Med, 1997. 186(11): p. 1853-63.
15. Fan, S. T. and T. S. Edgington, *Coupling of the adhesive receptor CD11b/CD18 to functional enhancement of effector macrophage tissue factor response.* J Clin Invest, 1991. 87(1): p. 50-7.
16. Whitlock, B. B., et al., *Differential roles for alpha(M)beta(2) integrin clustering or activation in the control of apoptosis via regulation of akt and ERK survival mechanisms.* Cell Biol, 2000. 151(6): p. 1305-20.
17. Rezzonico, R., et al., *Ligation of CD11b and CD11c beta(2) integrins by antibodies or soluble CD23 induces macrophage inflammatory protein 1 alpha (MIP-1 alpha) and MIP-1beta production in primary human monocytes through a pathway dependent on nuclear factor-kappaB.* Blood, 2001. 97(10): p. 2932-40.
18. Guha, M. and N. Mackman, *The phosphatidylinositol 3-kinase-Akt pathway limits lipopolysaccharide activation of signaling pathways and expression of inflammatory mediators in human monocytic cells.* J Biol Chem, 2002. 277(35): p. 32124-32.
19. Rubel, C., et al., *Fibrinogen-CD11b/CD18 interaction activates the NF-kappa B pathway and delays apoptosis in human neutrophils.* Eur J Immunol, 2003. 33(5): p. 1429-38.
20. Kettritz, R., et al., *Integrins and cytokines activate nuclear transcription factor-kappaB in human neutrophils.* J Biol Chem, 2004. 279(4): p. 2657-65.
21. Giancotti, F. G. and E. Ruoslahti, *Integrin signaling.* Science, 1999. 285(5430): p. 1028-32.
22. Jaeschke, H., et al., *Functional inactivation of neutrophils with a Mac-1 (CD11b/CD18) monoclonal antibody protects against ischemia-reperfusion injury in rat liver.* Hepatology, 1993. 17(5): p. 915-23.
23. Rogers, C., E. R. Edelman, and D. I. Simon, *A mAb to the beta2-leukocyte integrin Mac-1 (CD11b/CD18) reduces intimal thickening after angioplasty or stent implantation in rabbits.* Proc Natl Acad Sci USA, 1998. 95(17): p. 10134-9.
24. Wilson, I., et al., *Inhibition of neutrophil adherence improves postischemic ventricular performance of the neonatal heart.* Circulation, 1993. 88(5 Pt 2): p. 11372-9.
25. Plow, E. F. and L. Zhang, *A MAC-1 attack: integrin functions directly challenged in knockout mice.* J Clin Invest, 1997. 99(6): p. 1145-6.
26. Yonekawa, K. and J. M. Harlan, *Targeting leukocyte integrins in human diseases.* J Leukoc Biol, 2005. 77(2): p. 129-40.
27. Hu, X., et al., *beta2-integrins in demyelinating disease: not adhering to the paradigm.* J Leukoc Biol, 2010. 87(3): p. 397-403.
28. Dove, A., *CD18 trials disappoint again.* Nat Biotechnol, 2000. 18(8): p. 817-8.
29. Shimizu, K., et al., *Leukocyte integrin Mac-1 promotes acute cardiac allograft rejection.* Circulation, 2008. 117 (15): p. 1997-2008.
30. Ramamoorthy, C., et al., *CD18 adhesion blockade decreases bacterial clearance and neutrophil recruitment after intrapulmonary E. coli, but not after S. aureus.* J Leukoc Biol, 1997. 61(2): p. 167-72.
31. Lum, A. F., et al., *Dynamic regulation of LFA-1 activation and neutrophil arrest on intercellular adhesion molecule 1 (ICAM-1) in shear flow.* J Biol Chem, 2002. 277(23): p. 20660-70.
32. Allison, M., *PML problems loom for Rituxan.* Nat. Biotechnol, 2010. 28(2): p. 105-6.
33. Park, J. Y., M. A. Arnaout, and V. Gupta, *A simple, no-wash cell adhesion-based high-throughput assay for the discovery of small-molecule regulators of the integrin CD11b/CD18.* J Biomol Screen, 2007. 12(3): p. 406-17.
34. Faridi, M. H., et al., *Identification of novel agonists of the integrin CD11b/CD18.* Bioorg Med Chem Lett, 2009. 19(24): p. 6902-6.
35. Kuijpers, T. W., et al., *Freezing adhesion molecules in a state of high-avidity binding blocks eosinophil migration.* J Exp Med, 1993. 178(1): p. 279-84.
36. Semmrich, M., et al., *Importance of integrin LFA-1 deactivation for the generation of immune responses.* J Exp Med, 2005. 201(12): p. 1987-98.
37. Park, E. J., et al., *Distinct roles for LFA-1 affinity regulation during T-cell adhesion, diapedesis, and interstitial migration in lymph nodes.* Blood, 2010. 115(8): p. 1572-81.
38. Park, E. J., et al., *Aberrant activation of integrin alpha4beta7 suppresses lymphocyte migration to the gut.* J Clin Invest, 2007. 117(9): p. 2526-38.
39. Faridi, M. H., et al., *Identification of novel agonists of the integrin CD11b/CD18.* Bioorg Med Chem Lett, 2009.
40. Wang, Y., et al., *Leukocyte engagement of platelet glycoprotein Ibalpha via the integrin Mac-1 is critical for the biological response to vascular injury.* Circulation, 2005. 112(19): p. 2993-3000.
41. Arnaout, M. A., et al., *Inhibition of phagocytosis of complement C3- or immunoglobulin G-coated particles and of C3bi binding by monoclonal antibodies to a monocyte-granulocyte membrane glycoprotein (Mol).* J Clin Invest, 1983. 72(1): p. 171-9.
42. Wright, S. D., et al., *Identification of the C3bi receptor of human monocytes and macrophages by using monoclonal antibodies.* Proc Natl Acad Sci USA, 1983. 80(18): p. 5699-703.
43. Hogg, N., et al., *A novel leukocyte adhesion deficiency caused by expressed but nonfunctional beta2 integrins Mac-1 and LFA-1.* J Clin Invest, 1999. 103(1): p. 97-106.
44. Dransfield, I. and N. Hogg, *Regulated expression of Mg2+ binding epitope on leukocyte integrin alpha subunits.* EMBO J, 1989. 8(12): p. 3759-65.

45. Coxon, A., et al., *A novel role for the beta 2 integrin CD11b/CD18 in neutrophil apoptosis: a homeostatic mechanism in inflammation.* Immunity, 1996. 5(6): p. 653-66.

46. Gupta, V., et al., *The beta-tail domain (betaTD) regulates physiologic ligand binding to integrin CD11b/CD18.* Blood, 2007. 109(8): p. 3513-20.

47. Alonso, J. L., et al., *Does the integrin alphaA domain act as a ligand for its betaA domain?* Curr Biol, 2002. 12(10): p. R340-2.

48. Gupta, V., *HTS identification of compounds that enhance the binding of CD11b/CD18 to fibrinogen via a luminescence assay.* Pubchem Assay ID 1499, 2009.

49. Chen, L. Y., et al., *Impaired glucose homeostasis, neutrophil trafficking and function in mice lacking the glucose-6-phosphate transporter.* Hum Mol Genet, 2003. 12(19): p. 2547-58.

50. Bergmeier, W., et al., *Mice lacking the signaling molecule CalDAG-GEFI represent a model for leukocyte adhesion deficiency type III.* J Clin Invest, 2007. 117(6): p. 1699-707.

51. Szczur, K., et al., *Rho GTPase CDC42 regulates directionality and random movement via distinct MAPK pathways in neutrophils.* Blood, 2006. 108(13): p. 4205-13.

52. Zigmond, S. H., *Orientation chamber in chemotaxis.* Methods Enzymol, 1988. 162: p. 65-72.

53. Pluskota, E., et al., *Neutrophil apoptosis: selective regulation by different ligands of integrin alphaMbeta2.* J Immunol, 2008. 181(5): p. 3609-19.

54. Li, R. and M. A. Amaout, *Functional analysis of the beta 2 integrins.* Methods Mol Biol, 1999. 129: p. 105-24.

55. Xiong, J. P., et al., *An isoleucine-based allosteric switch controls affinity and shape shifting in integrin CD11b A-domain.* J Biol Chem, 2000. 275(49): p. 38762-7.

56. Lu, C., et al., *Epitope mapping of antibodies to the C-terminal region of the integrin beta 2 subunit reveals regions that become exposed upon receptor activation.* J Immunol, 2001. 166(9): p. 5629-37.

57. Xiong, J. P., et al., *New insights into the structural basis of integrin activation.* Blood, 2003. 102(4): p. 1155-9.

58. Gabeler, E. E., et al., *A comparison of balloon injury models of endovascular lesions in rat arteries.* BMC Cardiovasc Disord, 2002. 2: p. 16.

59. Renshaw, S. A., et al., *A transgenic zebrafish model of neutrophilic inflammation.* Blood, 2006. 108(13): p. 3976-8.

60. Nüsslein-Volhard, C., *Zebrafish—A Practical Approach.* Practical Approach Series. 2002: Oxford University Press.

61. Lee, J. O., et al., *Crystal structure of the A domain from the alpha subunit of integrin CR3 (CD11b/CD18).* Cell, 1995. 80(4): p. 631-8.

62. Xiong, J. P., et al., *An isoleucine-based allosteric switch controls affinity and shape shifting in integrin CD11b A-domain.* J Biol Chem, 2000. 275(49): p. 38762-7.

63. Weitz-Schmidt, G., et al., *Statins selectively inhibit leukocyte function antigen-1 by binding to a novel regulatory integrin site.* Nat Med, 2001. 7(6): p. 687-92.

64. Lee, J. O., et al., *Two conformations of the integrin A-domain (I-domain): a pathway for activation?* Structure, 1995. 3(12): p. 1333-40.

65. Shimaoka, M., et al., *Stabilizing the integrin alpha M inserted domain in alternative conformations with a range of engineered disulfide bonds.* Proc Natl Acad Sci USA, 2002. 99(26): p. 16737-41.

66. McCleverty, C. J. and R. C. Liddington, *Engineered allosteric mutants of the integrin alphaMbeta2 I domain: structural and functional studies.* Biochem J, 2003. 372(Pt 1): p. 121-7.

67. Sherman, W., et al., *Novel procedure for modeling ligand/receptor induced fit effects.* J Med Chem, 2006. 49(2): p. 534-53.

68. Kevin, J. B., et al., *Scalable Algorithms for Molecular Dynamics Simulations on Commodity Clusters.* Proceedings of the ACM/IEEE Conference on Supercomputing (SC06), Tampa, Fla., Nov. 11-17, 2006.

69. Barnard, J. W., et al., *Neutrophil inhibitory factor prevents neutrophil-dependent lung injury.* J Immunol, 1995. 155(10): p. 4876-81.

70. Zerria, K., et al., *Recombinant integrin CD11b A-domain blocks polymorphonuclear cells recruitment and protects against skeletal muscle inflammatory injury in the rat.* Immunology, 2006. 119(4): p. 431-40.

71. Feng, Y., et al., *Peptides derived from the complementarity-determining regions of anti-Mac-1 antibodies block intercellular adhesion molecule-1 interaction with Mac-1.* J Biol Chem, 1998. 273(10): p. 5625-30.

72. Li, R., et al., *Two functional states of the CD11b A-domain: correlations with key features of two Mn2+-complexed crystal structures.* J Cell Biol, 1998. 143(6): p. 1523-34.

73. Abad-Zapatero, C. and J. T. Metz, *Ligand efficiency indices as guideposts for drug discovery.* Drug Discov Today, 2005. 10(7): p. 464-9.

74. Friesner, R. A., et al., *Glide: a new approach for rapid, accurate docking and scoring. 1. Method and assessment of docking accuracy.* J Med Chem, 2004. 47(7): p. 1739-49.

75. Guimaraes, C. R. and M. Cardozo, *MM-GB/SA rescoring of docking poses in structure-based lead optimization.* J Chem Inf Model, 2008. 48(5): p. 958-70.

76. Bjorklund, M., et al., *Stabilization of the activated alphaMbeta2 integrin by a small molecule inhibits leukocyte migration and recruitment.* Biochemistry, 2006. 45(9): p. 2862-71.

77. Liu, L., et al., *Requirement for RhoA kinase activation in leukocyte de-adhesion.* J Immunol, 2002. 169(5): p. 2330-6.

78. Huttenlocher, A., M. H. Ginsberg, and A. F. Horwitz, *Modulation of cell migration by integrin-mediated cytoskeletal linkages and ligand-binding affinity.* J Cell Biol, 1996. 134(6): p. 1551-62.

79. Palecek, S. P., et al., *Integrin-ligand binding properties govern cell migration speed through cell-substratum adhesiveness.* Nature, 1997. 385(6616): p. 537-40.

80. de Bruyn, K. M., et al., *The small GTPase Rap1 is required for Mn(2+)- and antibody-induced LEA-1- and VLA-4-mediated cell adhesion.* J Biol Chem, 2002. 277(33): p. 29468-76.

81. Lefort, C. T., et al., *Outside-in signal transmission by conformational changes in integrin Mac-1.* J Immunol, 2009. 183(10): p. 6460-8.

82. Springer, T., et al., *Mac-1: a macrophage differentiation antigen identified by monoclonal antibody.* Eur J Immunol, 1979. 9(4): p. 301-6.

83. De Vriese, A. S., et al., *The role of selectins in glomerular leukocyte recruitment in rat anti-glomerular basement membrane glomerulonephritis.* J Am Soc Nephrol, 1999. 10(12): p. 2510-7.

I claim:

1. A method of treating an inflammatory disease associated with the activity of beta2 integrins in a patient comprising administering to the patient an effective amount of a compound having the formula:

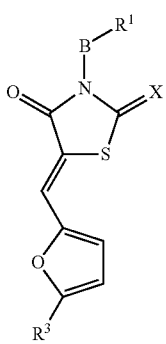

or a pharmaceutically acceptable salt thereof, wherein

B is absent and $R^1$ is phenyl, or

B is methylene and $R^1$ is phenyl or phenyl substituted with one fluoro;

N is nitrogen;

X is selected from the group consisting of O and S;

$R^3$ is selected from the group consisting 4-carboxyphenyl and 3-carboxy-4-chlorophenyl;

and the compound is a substantially pure single Z conformer.

2. The method of claim 1, wherein the inflammatory disease is selected from the group consisting of acute inflammation, chronic inflammation, chronic kidney disease, neointimal thickening associated with vascular injury, tissue injury, and peritonitis.

3. The method of claim 1, wherein the inflammatory disease is associated with tumor infiltration of leukocytes.

4. The method of claim 1, wherein the compound is selected from the group consisting of

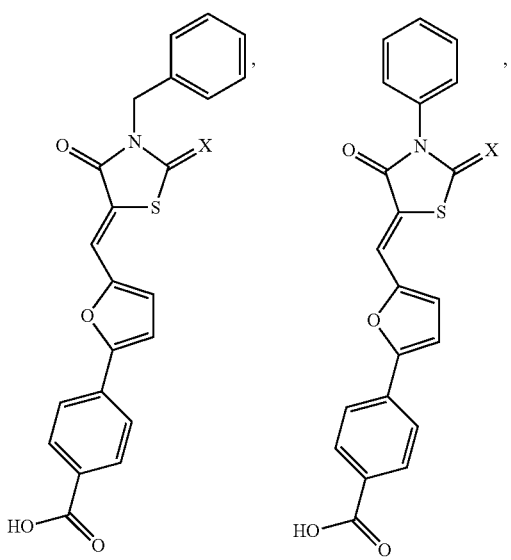
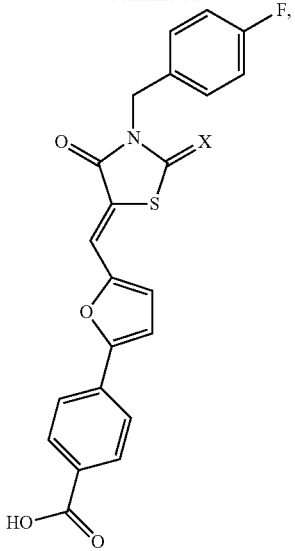
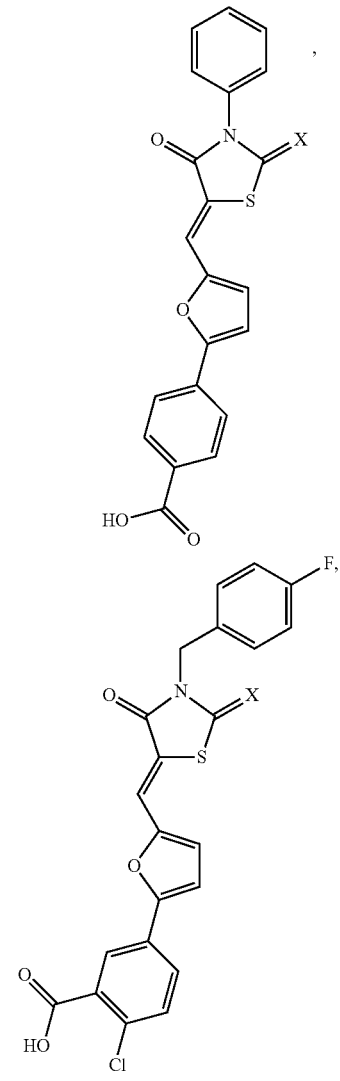
-continued
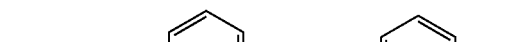
and pharmaceutically acceptable salts thereof, wherein the compound is a substantially pure single Z conformer.
5. The method of claim 1, wherein the compound is selected from the group consisting of
and -continued
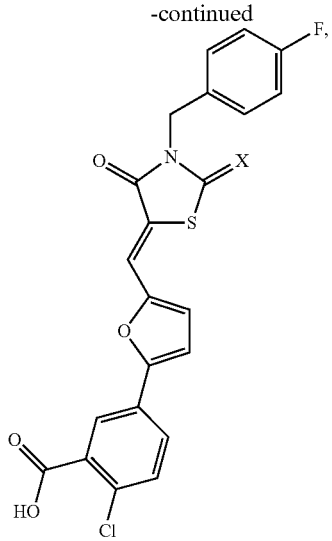
and
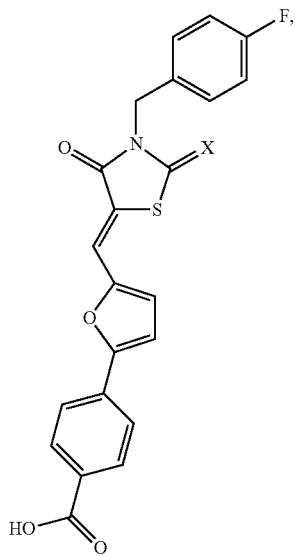
and pharmaceutically acceptable salts thereof wherein the compound is a substantially pure single Z conformer.
6. The method of claim 1, wherein the compound is
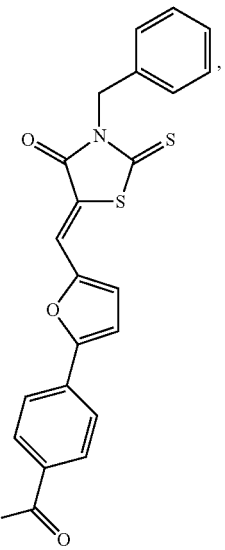
or a pharmaceutically acceptable salt thereof.
7. The method of claim 1, wherein the compound is
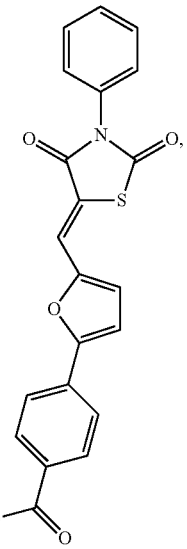
or a pharmaceutically acceptable salt thereof.

8. The method of claim 1, wherein the compound is

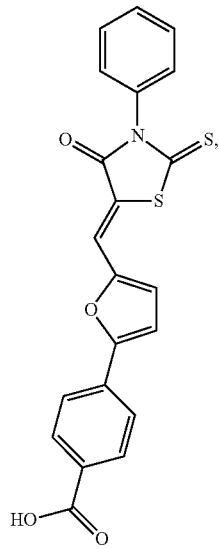 [SMILES: O=C(O)c1ccc(-c2ccc(/C=C3\SC(=O)N(c4ccccc4)C3=O)o2)cc1]

or a pharmaceutically acceptable salt thereof.

9. The method of claim 1, wherein the compound is

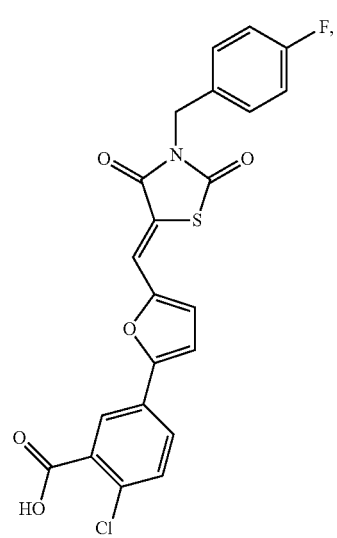 [SMILES: O=C(O)c1cc(-c2ccc(/C=C3\SC(=O)N(Cc4ccc(F)cc4)C3=O)o2)ccc1Cl]

or a pharmaceutically acceptable salt thereof.

10. The method of claim 1, wherein the compound is

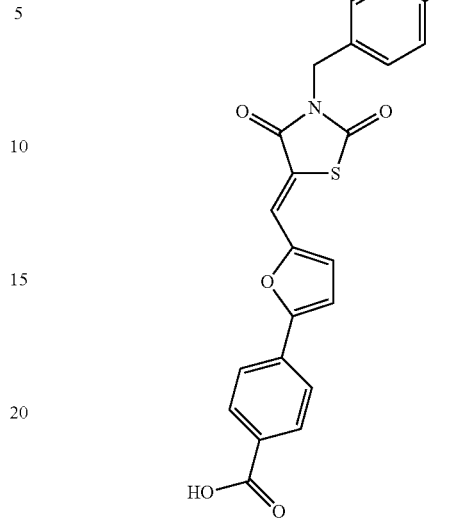

or a pharmaceutically acceptable salt thereof.

11. A method of treating an inflammatory disease associated with the activity of beta2 integrins in is patient comprising administering to the patient an effective amount of a compound having the formula:

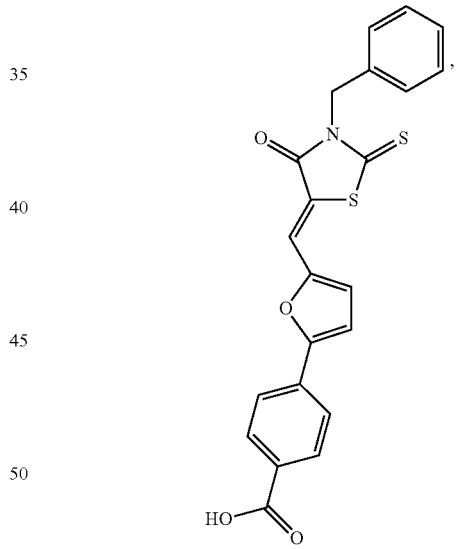

or a pharmaceutically acceptable salt thereof wherein the compound is a substantially pure single Z conformer.

* * * * *

UNITED STATES PATENT AND TRADEMARK OFFICE
CERTIFICATE OF CORRECTION

PATENT NO. : 9,023,876 B2  Page 1 of 1
APPLICATION NO. : 12/904273
DATED : May 5, 2015
INVENTOR(S) : Vineet Gupta It is certified that error appears in the above-identified patent and that said Letters Patent is hereby corrected as shown below:

In the claims

Column 64, line 28, the part of the text "integrins in is patient", should read --integrins in a patient--.

Signed and Sealed this
Third Day of May, 2016

Michelle K. Lee
*Director of the United States Patent and Trademark Office*

SEQUENCE LISTING

```
<160> NUMBER OF SEQ ID NOS: 4

<210> SEQ ID NO 1
<211> LENGTH: 55
<212> TYPE: DNA
<213> ORGANISM: Artificial Sequence
<220> FEATURE:
<223> OTHER INFORMATION: Forward PCR primer

<400> SEQUENCE: 1
ggttccgcgt ggatccgaga acctgtactt tcaaggagga tccaacctac ggcag      55

<210> SEQ ID NO 2
<211> LENGTH: 34
<212> TYPE: DNA
<213> ORGANISM: Artificial Sequence
<220> FEATURE:
<223> OTHER INFORMATION: Reverse PCR primer

<400> SEQUENCE: 2
gaattcccgg ggatccaccc tcgatcgcaa agat                             34

<210> SEQ ID NO 3
<211> LENGTH: 52
<212> TYPE: DNA
<213> ORGANISM: Artificial Sequence
<220> FEATURE:
<223> OTHER INFORMATION: Forward PCR primer

<400> SEQUENCE: 3
ggttccgcgt ggatccgaga acctgtactt tcaaggaggt tttcaggaat gt          52

<210> SEQ ID NO 4
<211> LENGTH: 39
<212> TYPE: DNA
<213> ORGANISM: Artificial Sequence
<220> FEATURE:
<223> OTHER INFORMATION: Reverse PCR primer

<400> SEQUENCE: 4
atatccccgg gattaaccct cgatcgcaaa gcccttctc                         39
```